(12) United States Patent
Zhang

(10) Patent No.: US 12,221,406 B2
(45) Date of Patent: Feb. 11, 2025

(54) COMPOUNDS AS NLRP3 INFLAMMASOME INHIBITORS AND COMPOSITIONS AND USES THEREOF

(71) Applicant: VIRGINIA COMMONWEALTH UNIVERSITY, Richmond, VA (US)

(72) Inventor: Shijun Zhang, Glen Allen, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 17/627,214

(22) PCT Filed: Jul. 15, 2020

(86) PCT No.: PCT/US2020/042036
§ 371 (c)(1),
(2) Date: Jan. 14, 2022

(87) PCT Pub. No.: WO2021/011592
PCT Pub. Date: Jan. 21, 2021

(65) Prior Publication Data
US 2022/0259144 A1    Aug. 18, 2022

Related U.S. Application Data

(60) Provisional application No. 62/874,570, filed on Jul. 16, 2019.

(51) Int. Cl.
| | | |
|---|---|---|
| C07D 333/24 | (2006.01) |
| A61P 37/02 | (2006.01) |
| C07C 311/37 | (2006.01) |
| C07C 311/46 | (2006.01) |
| C07D 207/20 | (2006.01) |
| C07D 209/14 | (2006.01) |
| C07D 233/26 | (2006.01) |
| C07D 241/12 | (2006.01) |
| C07D 249/04 | (2006.01) |
| C07D 277/56 | (2006.01) |
| C07D 277/593 | (2006.01) |
| C07D 285/06 | (2006.01) |
| C07D 307/64 | (2006.01) |
| C07D 317/62 | (2006.01) |
| C07D 409/12 | (2006.01) |
| C07D 413/12 | (2006.01) |

(52) U.S. Cl.
CPC ............ *C07C 311/37* (2013.01); *A61P 37/02* (2018.01); *C07C 311/46* (2013.01); *C07D 207/20* (2013.01); *C07D 209/14* (2013.01); *C07D 233/26* (2013.01); *C07D 241/12* (2013.01); *C07D 249/04* (2013.01); *C07D 277/56* (2013.01); *C07D 277/593* (2013.01); *C07D 285/06* (2013.01); *C07D 307/64* (2013.01); *C07D 317/62* (2013.01); *C07D 333/24* (2013.01); *C07D 409/12* (2013.01); *C07D 413/12* (2013.01)

(58) Field of Classification Search
None
See application file for complete search history.

(56) References Cited

PUBLICATIONS

Database Registry Chemical Abstracts Service, Columbus, Ohio, Accession No. RN 880814-50-6, Entered STN: Apr. 18, 2006.*
Database Registry Chemical Abstracts Service, Columbus, Ohio, Accession No. RN 260245-44-1, Entered STN: Mar. 28, 2000.*

* cited by examiner

*Primary Examiner* — Samantha L Shterengarts

(57) ABSTRACT

Scaffold compounds are used to design small molecule compounds and structure-activity relationship studies identify inhibitors of inflammation. Methods include pharmaceutical compositions of the small molecule compounds to inhibit, prevent and treat diseases and conditions associated with inflammation, including multiple sclerosis, Alzheimer's disease, acute myocardial infarction, traumatic brain injury and autoinflammatory diseases.

1 Claim, 6 Drawing Sheets

1A

1B

1C

3A

3B

3C

3D

3E

4A

4B

4C

COMPOUNDS AS NLRP3 INFLAMMASOME INHIBITORS AND COMPOSITIONS AND USES THEREOF

FEDERALLY SPONSORED RESEARCH OR DEVELOPMENT

This invention was made with government support under Grant Number R01 AG058673 awarded by the National Institutes of Health (NIH). The government has certain rights in the invention.

BACKGROUND OF THE INVENTION

Field of the Invention

The invention generally relates to small molecule compounds that modulate the innate immune responses and methods of their use to inhibit pathological responses associated with innate immune dysregulation or over-activation. In particular, the invention provides small molecule compounds that inhibit the NLRP3 inflammasome activation, and methods of using the small molecule compounds to prevent or treat NRLP3 inflammasome associated diseases and conditions, such as inflammation and autoimmune/autoinflammatory diseases.

Background of the Invention

Inflammasomes are intracellular multiprotein complexes that tightly regulate the innate immune response and the production of pro-inflammatory cytokines such as interleukin (IL)-1β and IL-18. The inflammasomes share a similar structure and are typically formed by a cytosolic pattern-recognition receptor, an adaptor protein, and an effector component (caspase-1). Upon assembly and activation, inflammasomes provide the platform to activate caspase 1 by autoproteolytic cleavage. The NOD-like receptor family pyrin domain-containing 3 (NLRP3) inflammasome is composed of NLRP3, the apoptosis-associated speck-like protein containing a caspase recruitment domain (ASC), caspase-1, and a recently identified NIMA-related kinase 7 (NEK7). The NLRP3 inflammasome is crucial for maturation of IL-1β and IL-18 with biological activity. The assembly of the NLRP3 inflammasome requires the interaction of NLRP3 protein and the adaptor component ASC. This interaction leads to the recruitment of pro-caspase-1 and subsequently to maturation and secretion of pro-inflammatory cytokines IL-β and IL-18. Through this complex interaction between the sensors, adaptors, and effectors, the inflammasome serves as a "guardian" for external or internal stress and a key "amplifier" of the inflammatory response.

Alzheimer's disease (AD) is a neurodegenerative disorder and the most common cause of dementia. Current AD treatments provide only symptomatic relief and there are no agents available to delay or cure this disease. Therefore, there is a desperate need to develop safe and effective AD treatments. Among the indicated AD risk factors, neuroinflammation has been recognized as an essential player. Recently the NLRP3 inflammasome has been identified as a critical multiprotein platform that tightly regulates the innate immune response and the production of pro-inflammatory cytokines such as interleukin (IL)-1β and IL-18. Notably, emerging evidence have suggested a link between NLRP3 inflammasome and AD development. Among the known inflammasomes, the NLRP3 inflammasome is the most extensively studied regulator of the production of IL-1β and IL-18. Notably, numerous studies have provided evidence to link NLRP3 inflammasome and IL-1β to AD development. For example, NLRP3, ASC, caspase-1 and down-stream effectors including IL-1β and IL-18 were found to be upregulated both at mRNA and protein levels in AD mouse models and AD patients. Both in vitro and in vivo studies demonstrated that the NLRP3 inflammasome can sense both exogenous and endogenous molecules including AP aggregates and mediates the recruitment of microglia to AP. Furthermore, both IL-1β and IL-18 have shown essential roles in AD pathology such as synaptic plasticity, amyloidogenesis, and tauopathy. However, beneficial effects of IL-1β in reducing AP burden have also been reported in transgenic AD mice, thus illustrating the complicated network of innate immunity in AD development. Collectively, the results clearly suggested the essential roles of the NLRP3 inflammasome axis in the observed inflammatory responses of aging process and AD development.

Multiple sclerosis (MS) is an immune-mediated and neurodegenerative disorder characterized by neuroinflammation and demyelination. Currently there is no cure for MS and current medications mainly speed up recovery, reduced relapse rates, or manage symptoms. Although the exact etiology and pathogenesis of MS remain unknown, emerging evidence supports a critical role for NLRP3 inflammasome and IL-1β in the pathogenesis of MS. Clinical studies showed that expression of caspase-1, IL-1β, and IL-18 was elevated in MS plaques and peripheral mononuclear cells of MS patients. Absence of the inflammasome products caspase-1, IL-1β and IL-18 rendered mice resistance to experimental autoimmune encephalomyelitis (EAE), a mouse model that mimics human MS. Animal studies have shown that NLRP3 deficiency substantially delayed onset and reduced severity of EAE symptoms, decreased neuroinflammation, demyelination and oligodendrocyte loss progression. Recently, the effectiveness of IFN-β, a drug that has been used for more than 15 years as a first-line treatment for human MS, was found to depend on NLRP3 inflammasome, suggesting that IFN-β may therapeutically target the NLRP3 inflammasome-IL-1β axis in MS. Given the fact that many MS patients fail to respond to currently available MS treatments, including IFN-β, development of novel small molecule inhibitors targeting the NLRP3 inflammasome pathway will provide new opportunities to disease intervention for therapeutic benefits in the clinic.

The NLRP3 inflammasome also plays critical roles in the inflammatory responses to myocardial injury during acute myocardial infarction (AMI). In the early phases of AMI, the acute ischemic injury induces the expression of NLRP3 inflammasome components (priming), which concomitantly provides the stimuli leading to NLRP3 activation and formation of the macromolecular aggregate (trigger), leading to an active inflammasome. Reperfusion, while it effectively reduces infarct size, does not prevent activation of the NLRP3 inflammasome and leads to further injury through caspase-1-dependent inflammatory cell death.

NLRP3 inflammasome has attracted extensive interests as a promising target of drug development for pathological conditions in which the dysregulation or overactivation of this inflammasome is evident in many human diseases beyond AD, MS and AMI, including traumatic brain injury (TBI), arthritis, rheumatoid arthritis (RA), gout, diabetes, nonalcoholic steatohepatitis (NASH), chemotherapy-induced peripheral neuropathy (CIPN), acute respiratory distress syndrome (ARDS), acute lung injury (ALI), chimeric antigen receptor (CAR) T cell-induced cytokine release syndrome (CRS), and autoinflammatory diseases. Several small molecule inhibitors have recently been reported to block the NLRP3 inflammasome pathways. This includes MCC950, Bay 11-7082, CY-09, oridonin, tranilast, INF39, glyburide and JC124, among which MCC950 has been used in many studies as a pharmacological tool to demonstrate NLRP3 inflammasome as a viable drug target to development therapeutics for human diseases. However, in view of the involvement of the NLRP3 inflammasome in these and other disease processes, there is still a need for development of novel small molecule inhibitors targeting the NLRP3 inflammasome pathway and providing therapeutic benefits for the treatment of diseases.

SUMMARY OF THE INVENTION

The compounds of the invention are effective therapeutic agents with broad indications for human diseases. Compounds have been developed and tested in preclinical and/or clinical experiments, wherein novel chemical entities have shown desired in vivo activities.

In one embodiment of the invention, N-(5-chloro-2-methoxybenzyl)-N-(4-(N-(prop-2-yn-1-yl)sulfamoyl)phenethyl) acrylamide small molecule compounds are NLRP3 inflammasome inhibitors. The NLRP3 inflammasome inhibitors of the invention are useful for treating inflammation arising from disease or injury and for treating diseases involving inflammation.

In some embodiments, the invention comprises one or more compounds, depicted in generic Formula I or II. Formula I and/or Formula II comprises NLRP3 inflammasome inhibitors and is also a scaffold for synthesizing other NLRP3 inflammasome inhibitors.

In other embodiments, the small molecule compounds are Formula III, IV, V and/or VI, which are NLRP3 inflammasome inhibitors and novel therapeutic agents. The small molecule compounds having the chemical structures of Formula III-VI were synthesized from the base scaffolds of Formula I and Formula II.

In other embodiments, the invention is a method of treatment using one or more NLRP3 inflammasome inhibitor small molecule compounds disclosed herein. A pharmaceutical composition comprising at least one small molecule compound is administered to a subject in need thereof. The pharmaceutical composition of the invention is useful as a therapeutic agent for inhibiting, preventing or treating AD, MS, AMI, TBI, ALS, CIPN, ARDS/ALI, NASH, RA, arthritis, CRS and gout in patients in need thereof, as well as patients suffering from other autoinflammatory disease.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

Thus, it is an object of this invention to provide a compound of Formula I, or its pharmaceutically acceptable salts, solvates or hydrates:

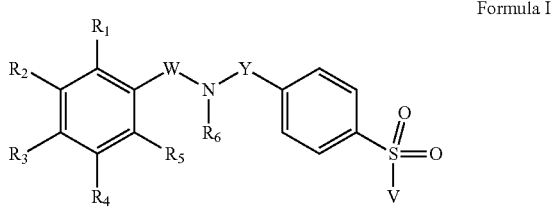

Formula I wherein
R1 is unbranched, branched, saturated, unsaturated, cyclic or acyclic, substituted or unsubstituted C1-C8 alkyl or is unbranched, branched, saturated, unsaturated, cyclic or acyclic, substituted or unsubstituted C1-C8 alkoxyl, or nitro, or cyano;

R4 is H, halogen, amino, nitro or cyano;

R2, R3 and R5 may be the same or different and are independently selected from H, C1-C8 unbranched, branched, saturated, unsaturated, cyclic or acyclic, substituted or unsubstituted alkyl, C1-C8 unbranched, branched, saturated, unsaturated, cyclic or acyclic, substituted or unsubstituted alkoxyl, C1-C8 unbranched, branched, saturated, unsaturated, cyclic or acyclic, substituted or unsubstituted alkylcarbonyl, halogen, hydroxyl, amino, nitro and cyano;

W is unbranched, branched, saturated, unsaturated, substituted or unsubstituted C1-C4 alkyl and may be present or absent;

R6 is unbranched, branched, saturated, unsaturated, cyclic or acyclic, substituted or unsubstituted C1-C8 alkylcarbonyl; substituted or unsubstituted aryl or heteroarylcarbonyl; C1-C8 unbranched, branched, saturated, unsaturated, cyclic or acyclic, substituted or unsubstituted alkyl, or H;

Y is C1-C5 unbranched, branched, saturated, unsaturated, cyclic or acyclic, substituted or unsubstituted alkyl;

V is i) $NR^1R^2$ where $R^1$ and $R^2$ are H or C1-C8 alkyl and may be the same or different; or ii) a saturated heterocycle comprising N bonded directly to S; and pharmaceutically acceptable salts thereof.

In another aspect, the compound is

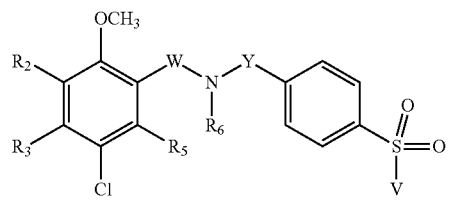

Formula II or pharmaceutically acceptable salts, solvates or hydrates thereof. The compound of Formula II comprises the structure of Formula I, and has fixed substituents of $OCH_3$ at R1 and Cl at R4 positions. The other moieties in the Compound of Formula II are the same as those specified above for Formula 1. That is, the other moieties are:

R2, R3 and R5 may be the same or different and are independently selected from H, C1-C8 unbranched, branched, saturated, unsaturated, cyclic or acyclic, substituted or unsubstituted alkyl, C1-C8 unbranched, branched, saturated, unsaturated, cyclic or acyclic, substituted or unsubstituted alkoxyl, C1-C8 unbranched, branched, saturated, unsaturated, cyclic or acyclic, substituted or unsubstituted alkylcarbonyl, halogen, hydroxyl, amino, nitro and cyano;

W is unbranched, branched, saturated, unsaturated, substituted or unsubstituted C1-C4 alkyl and may be present or absent;

R6 is unbranched, branched, saturated, unsaturated, cyclic or acyclic, substituted or unsubstituted C1-C8 alkylcarbonyl; substituted or unsubstituted aryl or heteroarylcarbonyl; C1-C8 unbranched, branched, saturated, unsaturated, cyclic or acyclic, substituted or unsubstituted alkyl.

Y is C1-C5 unbranched, branched, saturated, unsaturated, cyclic or acyclic, substituted or unsubstituted alkyl, V is i) NR1R2 where R1 and R2 are H or C1-C8 alkyl and may be the same or different; or ii) a saturated heterocycle comprising N bonded directly to S.

In another aspect, the compound is

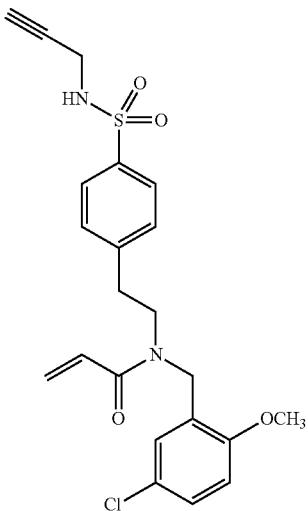

Formula III and pharmaceutically acceptable salts, solvates, or hydrates thereof.

Formula III comprises the base scaffold chemical structure of Formula II, having a further substituent of vinylcarbonyl at R6, H at R2, R3, and R5, and propargylamine at V positions, a methylene at W and an ethylene at Y.

In one preferred aspect, the compound is

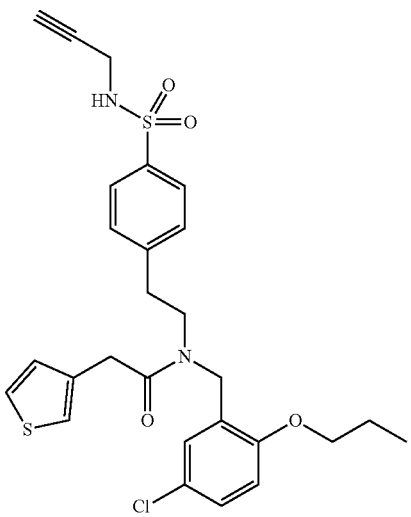

Formula IV or a pharmaceutically acceptable salt, solvate, or hydrate thereof.

Formula IV comprises the base scaffold chemical structure of Formula I, having a further substituent of $CH_3CH_2CH_2O$ at R1, 2-(thiophen-2-yl)acetyl at R6, Cl at R4, H at R2, R3, and R5, Cl at R4, and propargylamine at V positions, a methylene at W and an ethylene at Y.

In another preferred aspect, the compound is Formula V (SZ-N3I-88), having a chemical structure of:

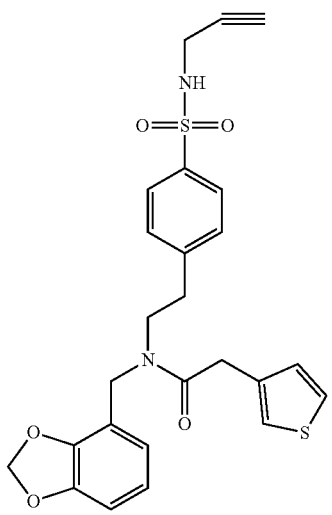

Formula V or a pharmaceutically acceptable salt, solvate, or hydrate thereof. Formula V comprises the base scaffold chemical structure of Formula I, having substituents of [1,3]-dioxole at R1 and R2, H at R3, R4 and R5, 2-(thiophen-2-yl)acetyl at R6, and propargylamine at V positions, a methylene at W and an ethylene at Y.

In another preferred aspect, the compound is Formula VI (SZ-N3I-89), having a chemical structure of:

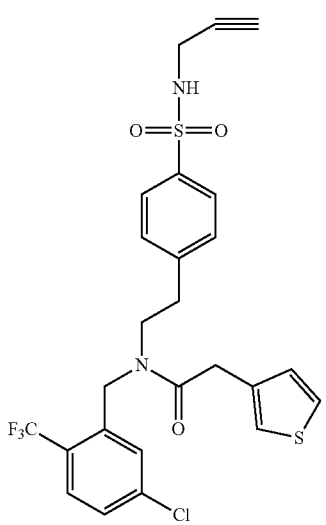

Formula VI or a pharmaceutically acceptable salt, solvate, or hydrate thereof. Formula VI comprises the base scaffold chemical structure of Formula I having substituents of $CF_3$ at R1, 2-(thiophen-2-yl)acetyl at R6, H at R2, R3, and R5, Cl at R4, and propargylamine at V positions, a methylene at W and an ethylene at Y.

The invention also provides pharmaceutical compositions comprising each of these compounds, and variants thereof as described herein, combined with a physiologically acceptable carrier (solid or liquid).

The invention also provides methods of inhibiting, preventing or treating NRLP3 inflammasome-associated inflammation or disease in a subject in need thereof, comprising a step of administering to said subject a therapeutically effective amount of the compound of Formula I:

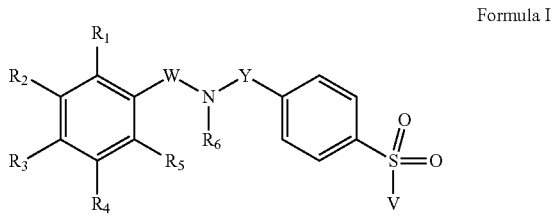

Formula I and pharmaceutically acceptable salts, solvates, or hydrates thereof, wherein
- R1 is unbranched, branched, saturated, unsaturated, cyclic or acyclic, substituted or unsubstituted C1-C8 alkyl or is unbranched, branched, saturated, unsaturated, cyclic or acyclic, substituted or unsubstituted C1-C8 alkoxyl, or nitro, or cyano;
- R4 is H, halogen, amino, nitro or cyano;
- R2, R3 and R5 may be the same or different and are independently selected from H, C1-C8 unbranched, branched, saturated, unsaturated, cyclic or acyclic, substituted or unsubstituted alkyl, C1-C8 unbranched, branched, saturated, unsaturated, cyclic or acyclic, substituted or unsubstituted alkoxyl, C1-C8 unbranched, branched, saturated, unsaturated, cyclic or acyclic, substituted or unsubstituted alkylcarbonyl, halogen, hydroxyl, amino, nitro and cyano;
- W is unbranched, branched, saturated, unsaturated, substituted or unsubstituted C1-C4 alkyl and may be present or absent;
- R6 is unbranched, branched, saturated, unsaturated, cyclic or acyclic, substituted or unsubstituted C1-C8 alkylcarbonyl; substituted or unsubstituted aryl or heteroarylcarbonyl; C1-C8 unbranched, branched, saturated, unsaturated, cyclic or acyclic, substituted or unsubstituted alkyl;
- Y is C1-C5 unbranched, branched, saturated, unsaturated, cyclic or acyclic, substituted or unsubstituted alkyl;
- V is i) NR$^1$R$^2$ where R$^1$ and R$^2$ are H or C1-C8 alkyl and may be the same or different; or ii) a saturated heterocycle comprising N bonded directly to S.

In exemplary methods of inhibiting, preventing or treating NRLP3 inflammasome-associated inflammation or disease in a subject in need thereof, the compound is

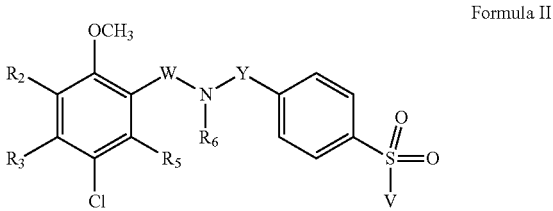

Formula II or pharmaceutically acceptable salts, solvates, or hydrates thereof,
wherein
- R2, R3 and R5 may be the same or different and are independently selected from H, C1-C8 unbranched, branched, saturated, unsaturated, cyclic or acyclic, substituted or unsubstituted alkyl, C1-C8 unbranched, branched, saturated, unsaturated, cyclic or acyclic, substituted or unsubstituted alkoxyl, C1-C8 unbranched, branched, saturated, unsaturated, cyclic or acyclic, substituted or unsubstituted alkylcarbonyl, halogen, hydroxyl, amino, nitro and cyano;
- W is unbranched, branched, saturated, unsaturated, substituted or unsubstituted C1-C4 alkyl and may be present or absent;
- R6 is unbranched, branched, saturated, unsaturated, cyclic or acyclic, substituted or unsubstituted C1-C8 alkylcarbonyl; substituted or unsubstituted aryl or heteroarylcarbonyl; C1-C8 unbranched, branched, saturated, unsaturated, cyclic or acyclic, substituted or unsubstituted alkyl.
- Y is C1-C5 unbranched, branched, saturated, unsaturated, cyclic or acyclic, substituted or unsubstituted alkyl,
- V is i) NR1R2 where R1 and R2 are H or C1-C8 alkyl and may be the same or different; or ii) a saturated heterocycle comprising N bonded directly to S.

In other exemplary methods of inhibiting, preventing or treating NRLP3 inflammasome-associated inflammation or disease in a subject in need thereof, the compound is at least one small molecule compound selected from the group consisting of:

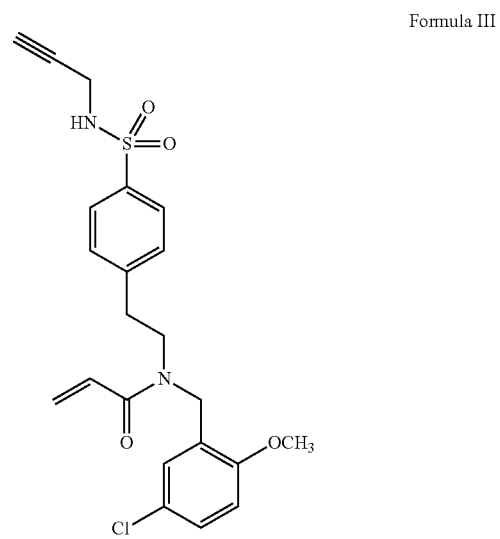 [SMILES: C#CCNS(=O)(=O)c1ccc(CCN(Cc2cc(Cl)ccc2OC)C(=O)C=C)cc1]

Formula III

-continued

Formula IV

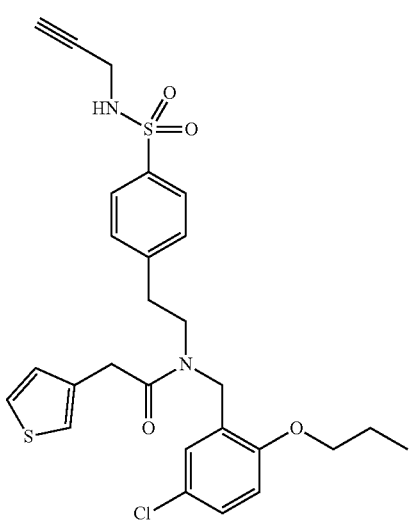

Formula V and

Formula VI or pharmaceutically acceptable salts, solvates, or hydrates thereof.

In one embodiment the invention is a pharmaceutical composition comprising a small molecule compound synthesized from the base scaffold of Formula I and/or Formula II, and variants thereof as described herein, combined with a physiologically acceptable carrier. The small molecule compound synthesized from the base scaffold of Formula I and/or Formula II may be selected from the compounds disclosed in Table 1 of Example 15.

In another embodiment, the invention is a pharmaceutical composition comprising at least one small molecule compound selected from the group consisting of Formula III, Formula IV, Formula V and Formula VI, combined with a physiologically acceptable carrier.

The invention is also a method of inhibiting, preventing or treating NRLP3 inflammasome-associated inflammation or disease in a subject in need thereof, comprising a step of administering to said subject a therapeutically effective amount of a pharmaceutical composition comprising a small molecule compound synthesized from the base scaffold of Formula I and/or Formula II, and variants thereof as described herein, combined with a physiologically acceptable carrier. The small molecule compound synthesized from the base scaffold of Formula I and/or Formula II may be selected from the compounds disclosed in Table 1 of Example 15.

In another embodiment, the invention is a method of inhibiting, preventing or treating NRLP3 inflammasome-associated inflammation or disease in a subject in need thereof, comprising a step of administering to said subject a therapeutically effective amount of a pharmaceutical composition comprising at least one small molecule compound selected from the group consisting of Formula III, Formula IV, Formula V and Formula VI, combined with a physiologically acceptable carrier.

In exemplary methods, the NRLP3 inflammasome-associated inflammation or disease is one or more selected from the group consisting of AD, MS, AMI, TBI, ALS, CIPN, ARDS/ALI, NASH, arthritis, RA, gout, CRS, and an auto-inflammatory condition.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

(FIG. 3A) Mouse peritoneal macrophages were primed with LPS (1 μg/mL) for 4.5 h and then treated with indicated compounds at indicated concentrations when adding ATP (5 mM) stimulation for 30 min. IL-β in the culture media was assayed by ELISA. (FIG. 3B) J774A.1 cells were treated with LPS (1 μg/mL) and compound 17 (Formula IV) (10 μM) for 1 h. Flagellin (1 μg/mL) was added and allowed to incubate for 6 hr or (Poly(dA:dT)) (4 μg/ml) for 8 hr. The supernatants were collected and levels of IL-1β were measured by ELISA. Serum levels of IL-1β (FIG. 3C) and TNF-α (FIG. 3D) from C57BL/6 (n=4 per group) mice pretreated compound 17 (Formula IV) (10 mg/kg) or MCC950 (10 mg/kg) were measured by ELISA 2.5 h after i.p. injection of LPS (50 mg/kg). (FIG. 3E) Serum levels of IL-1β and TNF-α under indicated treatment conditions (both compound 17 (Formula IV) and MCC950 were tested at 10 mg/kg) of nlrp3−/− mice (n=3 per group) were measured by ELISA 2.5 h after i.p. injection of LPS (25 mg/kg). Data are expressed as mean±SD. Statistical analysis by student t-test.

(FIG. 4A) hCMEC/D3 cells were treated with compound 17 (20 μM) for 2 h, then cell viability was measured using the Live/Dead™ kit. (FIG. 4B) hCMEC/D3 cells were plated on transwell filters. Compound 17 (Formula IV) (20 μM) was added to either the apical or basolateral side, then samples were analyzed by HPLC to determine flux (A-B: apical-to-basolateral; B-A: basolateral-to-apical) at indicated time points. (FIG. 4C) Spraque-Dawley rats were treated with compound 17 (Formula IV) (20 mg/kg) via IV and PO (n=3 per rout). Plasma samples were collected at indicated time points and analyzed by LC-MS/MS. Data are expressed as mean±SEM for studies in hCMEC/D3 cells, as mean±SD for studies in rats.

DETAILED DESCRIPTION

Figure 1A:
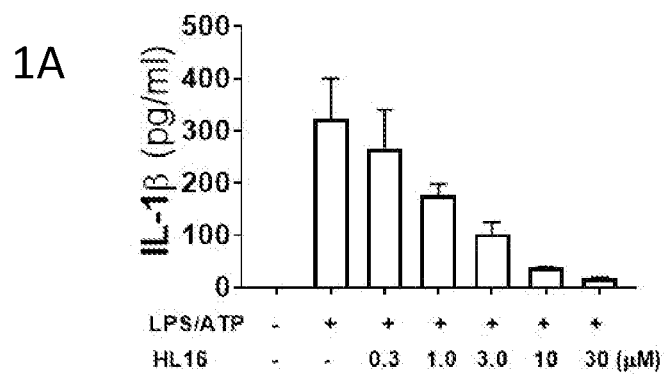
FIGS. 1A, 1B and 1C show that HL16 (Formula III) inhibits NLRP3 inflammasome. J774A.1 cells (1A) or mouse peritoneal macrophages (1B) were primed with LPS (1 µg/mL) for 4.5 h and then treated with indicated concentrations of HL16 when adding ATP (5 mM) stimulation for 30 min IL-β in the culture media was assayed by ELISA. (1C) J774A.1 cells were treated with LPS (1 µg/mL) and HL16 (10 µM) for 1 h. Flagellin (1 µg/mL) was added and allowed to incubate for 6 hr or (Poly(dA:dT)) (4 µg/ml) for 8 hr. The supernatants were collected and levels of IL-1β were measured by ELISA. Data are expressed as mean±SEM. Statistical analysis by student t-test.

The following descriptions and examples illustrate some exemplary embodiments of the disclosed invention in detail. Those of the skill in the art will recognize that there are numerous variations and modifications of this invention that are encompassed by its scope. Accordingly, the description of a certain exemplary embodiment should not be deemed to limit the scope the present invention.

As described herein, the invention comprises chemical compounds that are analogs, sulfonamide analogs, and small molecule compounds, and all such terms may be used interchangeably. The small molecule compounds disclosed herein are NLRP3 inflammasome inhibitors and are useful as therapeutics for AD, MS and TBI and other diseases having an inflammatory or autoinflammatory component.

As used herein, the small molecule compound of HL16 is Formula III, and the names may be used interchangeably.

As used herein, the small molecule compound 17 refers to Formula IV, and has also been identified as SZ-N3I-45 and YQ128, all of which may be used interchangeably.

As used herein, the small molecule compound of SZ-N31-88 refers to Formula V, and the names may be used interchangeably.

As used herein, the small molecule compound of SZ-N3I-89 refers to Formula VI, and the names may be used interchangeably.

As used herein, any "R" group(s) such as, without limitation, R, R1, R2, R3, R4, R5, R6 and so on represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. R groups at different locations may be the same or different.

As used herein, any "W", Y or V group(s) represent substituents that can be attached to the indicated atom. A W, Y or V group may be substituted or unsubstituted. W, Y or V groups at different locations may be the same or different.

As used herein, "alkyl" refers to a straight or branched hydrocarbon chain that includes a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "C1-C6 alkyl" or similar designations. By way of example only, "C1-C6 alkyl" indicates that there are one to four carbon atoms in the alkyl chain, i.e., the alkyl chain is selected from methyl, ethyl, propyl, isopropyl, n-butyl, isobutyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkylcarbonyl" refers to carbonyl attached to the above alkyl.

As used herein, "alkoxy" refers to the formula —OR wherein R is an alkyl, an alkenyl, an alkynyl, a cycloalkyl, a cycloalkenyl or a cycloalkynyl is defined as above. A non-limiting list of alkoxys is methoxy, ethoxy, n-propoxy, 1-methylethoxy (isopropoxy), n-butoxy, iso-butoxy, sec-butoxy and tert-butoxy. An alkoxy may be substituted or unsubstituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" is a heterocyclyl group derived from a heteroarene by removal of a hydrogen atom from any ring atom. Examples of heteroaryls include pyrrolidine, piperidine and pyridine.

As used herein, "vinylcarbonyl" is an alkene conjugated to a carbonyl group.

The term "halogen atom" or "halogen" as used herein, means any one of the radio-stable atoms of column 7 of the Periodic Table of the Elements, such as, fluorine, chlorine, bromine and iodine.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvates forms with pharmaceutically acceptable solvents such as water, ethanol, or the like. In other embodiments, the compounds described herein exist in unsolvated form. Solvates contain either stoichiometric or non-stoichiometric amounts of a solvents and may be formed during the process of crystallization with pharmaceutically acceptable solvent such as water, ethanol, or the like. Hydrates are formed when the solvent is water, or alcoholates are formed when the solvent is alcohol. In addition, the compound provided herein can exist in unsolvated as well as solvated forms. In general, the solvated forms are considered equivalent to the unsolvated form for the purpose of the compounds and methods provided herein.

Where a range of values is provided, it is understood that the upper and lower limit, and each intervening value between the upper and lower limit of the range is encompassed within the embodiments.

In one embodiment, the invention comprises new chemical scaffolds and the design and development of a series of compounds from the new chemical scaffolds.

In another embodiment, the invention comprises small molecule compounds that are sulfonamide analogs developed using the chemical scaffolds of the invention. The small molecule compounds inhibit NLRP3 inflammasome by directly interfering with the formation of the NLRP3 inflammasome complex and thus inhibit NLRP3 inflammasome mediated activity. Method of use for small molecule compounds that inhibit the NLRP3 inflammasome activity are provided, as are methods to treat various NLRP3-inflammasome related diseases and conditions. Examples of the invention demonstrate the direct binding interactions of the inhibitors of the invention with the NLRP3 protein, thus interfering with formation of the NLRP3 inflammasome.

In one embodiment of the method of the invention, the small molecule compounds demonstrate both in vitro and in vivo activities in animal models of AD and TBI. In other embodiments, analogs based on the chemical scaffolds of Formula I and Formula II demonstrate potency as inhibitors of NLRP3 inflammasome.

The analogs have the generic structures of Formula I:
wherein
R1 is unbranched, branched, saturated, unsaturated, cyclic or acyclic, substituted or

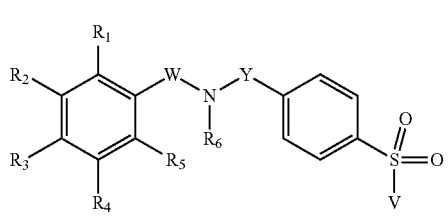

Formula I unsubstituted C1-C8 alkyl or is unbranched, branched, saturated, unsaturated, cyclic or acyclic, substituted or unsubstituted C1-C8 alkoxyl, or nitro, or cyano;

R4 is H, halogen, nitro or cyano;

R2, R3 and R5 may be the same or different and are independently selected from H, C1-C8 unbranched, branched, saturated, unsaturated, cyclic or acyclic, substituted or unsubstituted alkyl, C1-C8 unbranched, branched, saturated, unsaturated, cyclic or acyclic, substituted or unsubstituted alkoxyl, halogen, hydroxyl, amino, nitro and cyano;

W is unbranched, branched, saturated, unsaturated, substituted or unsubstituted C1-C4 alkyl and may be present or absent;

R6 is unbranched, branched, saturated, unsaturated, cyclic or acyclic, substituted or unsubstituted C1-C8 alkylcarbonyl; substituted or unsubstituted aryl or heteroarylcarbonyl; C1-C8 unbranched, branched, saturated, unsaturated, cyclic or acyclic, substituted or unsubstituted alkyl;

Y is C1-C5 unbranched, branched, saturated, unsaturated, cyclic or acyclic, substituted or unsubstituted alkyl;

V is i) $NR^1R^2$ where $R^1$ and $R^2$ are H or C1-C6 alkyl and may be the same or different; or ii) a saturated heterocycle comprising N bonded directly to S.

The compound may be present in crystalline or amorphous form. It may be dispersed or solubilized in a liquid carrier. The compound may be present as a salt, solvate, or hydrate.

In some aspects, the compound of Formula I has a methoxy group at the R1 position and Cl at the R4 position, and is identified as Formula II:

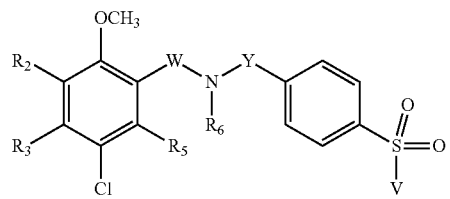

Formula II wherein
R2, R3 and R5 may be the same or different and are independently selected from H, C1-C8 unbranched, branched, saturated, unsaturated, cyclic or acyclic, substituted or unsubstituted alkyl, C1-C8 unbranched, branched, saturated, unsaturated, cyclic or acyclic, substituted or unsubstituted alkoxyl, halogen, hydroxyl, amino, nitro and cyano;

W is unbranched, branched, saturated, unsaturated, substituted or unsubstituted C1-C4 alkyl and may be present or absent;

R6 is unbranched, branched, saturated, unsaturated, cyclic or acyclic, substituted or unsubstituted C1-C8 alkylcarbonyl; substituted or unsubstituted aryl or heteroarylcarbonyl; C1-C8 unbranched, branched, saturated, unsaturated, cyclic or acyclic, substituted or unsubstituted alkyl;

Z is C1-C5 unbranched, branched, saturated, unsaturated, cyclic or acyclic, substituted or unsubstituted alkyl;

V is i) NR1R2 where R1 and R2 are H or C1-C6 alkyl and may be the same or different; or ii) a saturated heterocycle comprising N bonded directly to S.

For the compounds disclosed herein:

Exemplary halogens include but are not limited to: F, Cl, Br and I.

Exemplary alkyl groups include but are not limited to: CH3-, CH3CH2-, CH3(CH2)2-CH3(CH2)3-, CH3(CH2)4-, CH3(CH2)5-, CH3(CH2)6-, CH3(CH2)7-, which may be substituted or unsubstituted, or propargyl.

Exemplary alkoxyl groups include but are not limited to: CH3O—, CH3CH2O—, CH3(CH2)2O— CH3(CH2)3O—, CH3(CH2)4O—, CH3(CH2)5O—, CH3(CH2)6O—, CH3(CH2)7O—, which may be substituted or unsubstituted, or ethynyloxy.

"Substituted" refers to the inclusion of alkyl or a heteroatom or heteroatoms such as S, N, O, NO, OH, etc., within or attached to an alkyl chain or cyclic hydrocarbon.

Formula I is a base scaffold from which a library of small molecule compounds was synthesized and tested to determine inhibitory properties against NLRP3 inflammasome complex formation and activity. Formula II is a secondary base scaffold that is a product of Formula I with fixed substituents at R1 and R4. The synthetic methods disclosed herein were used to produce the library of small molecule compounds disclosed in Example 15 and elsewhere in this specification, including the small molecule compounds, as follows:

An exemplary compound is HL-16, having the chemical structure of Formula III:

Formula III

[structure]

Another exemplary compound is compound 17, having the chemical structure of Formula IV:

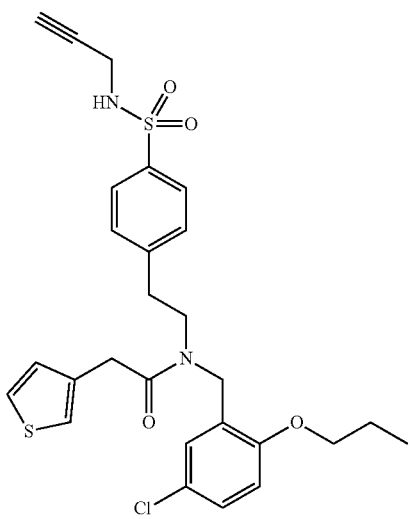

Formula IV

Another exemplary compound is SZ-N3I-88, having the chemical structure of:

Formula V

[structure]

Still another exemplary compound is SZ-N31-89, having the chemical structure of:

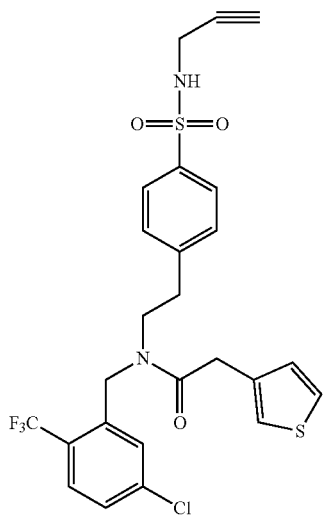

Formula VI

In one embodiment the invention is a pharmaceutical composition comprising a small molecule compound synthesized from the base scaffold of Formula I and/or Formula II, and variants thereof as described herein, combined with a physiologically acceptable carrier. The small molecule compound synthesized from the base scaffold of Formula I and/or Formula II may be selected from the compounds disclosed in Table 1 of Example 15.

In another embodiment, the invention is a pharmaceutical composition comprising at least one small molecule compound selected from the group consisting of Formula III, Formula IV, Formula V and Formula VI, combined with a physiologically acceptable carrier.

The invention is also a method of inhibiting, preventing or treating NRLP3 inflammasome-associated inflammation or disease in a subject in need thereof, comprising a step of administering to said subject a therapeutically effective amount of a pharmaceutical composition comprising a small molecule compound synthesized from the base scaffold of Formula I and/or Formula II, and variants thereof as described herein, combined with a physiologically acceptable carrier. The small molecule compound synthesized from the base scaffold of Formula I and/or Formula II may be selected from the compounds disclosed in Table 1 of Example 15.

In another embodiment, the invention is a method of inhibiting, preventing or treating NRLP3 inflammasome-associated inflammation or disease in a subject in need thereof, comprising a step of administering to said subject a therapeutically effective amount of a pharmaceutical composition comprising at least one small molecule compound selected from the group consisting of Formula III, Formula IV, Formula V and Formula VI, combined with a physiologically acceptable carrier.

The small molecule compounds disclosed herein are used to treat any disorder or condition associated with (e.g., caused by or related to or which exacerbates) unwanted or pathophysiological NLRP3 inflammasome activation and/or consequences of such activation, e.g., unwanted or pathological production of pro-inflammatory cytokines pro-IL-1β and pro-IL-18. Such diseases/conditions may be caused by so-called sterile inflammation (e.g., various inflammatory diseases, second wave inflammation after heart attack, stroke or other ischemic or traumatic injury to the brain or any other tissue or organ), or by inflammation that is caused by an infection (e.g., by an infectious organism such as a bacterium or virus). Such diseases and conditions result from a wide array of stimuli. For example, numerous microbes including various bacteria, viruses, fungi, and protozoan parasites can activate the NLRP3 inflammasome, e.g., the bacterial toxin nigericin has also been reported to induce the activation of NLRP3 by causing potassium efflux in a pannexin-1-dependent manner. In addition to microbial activators, endogenous "danger" signals such as ATP, monosodium urate (MSU) activate the NLRP3 inflammasome, as do various other types of cellular damage resulting, e.g., from metabolic stress, ischemia and trauma. For example, the NLRP3 inflammasome is implicated in metabolic disorders and sterile inflammatory responses including multiple sclerosis, arthritis, type II diabetes mellitus, gout and ischemia.

A number of endogenous and exogenous crystalline molecules activate the NLRP3 inflammasome, e.g. uric acid crystals and calcium pyrophosphate dihydrate, the causative agents of gout and pseudogout respectively. Silica and asbestos particles, which cause the fibrotic lung disorders silicosis and asbestosis respectively, also activate the NLRP3 inflammasome. Release of ATP from necrotic cells is a danger signal that activates the innate or sterile inflammatory immune response. Inhibiting NLRP3 inflammasome activation has beneficial effects in preventing the damage mediated by the sterile inflammatory response in diseases such as renal-, cardiac-, and cerebral-ischemia. In addition, necrosis-induced sterile inflammation in trauma and secondary to infections and sepsis are modulated by the inhibitors of the NLRP3 pathway described herein.

The NLRP3 inflammasome can also be activated by molecules associated with stress or danger, including crystalline and of particular auto-inflammatory diseases which may be inhibited, prevented or treated by the agents described herein include but are not limited to: joint, bone and muscle diseases such as rheumatoid arthritis, psoriatic arthritis, osteoarthritis, ankylosing spondylitis, erosive osteoarthritis of the hand, recurrent multifocal osteomyelitis, traumatic knee injury; relapsing polychondritis, hereditary systemic autoinflammatory diseases such as familial Mediterranean fever (FMF), cryopyrin-associated periodic syndrome (CAPS); Muckle-Wells Syndrome, TNF receptor-associated periodic syndrome (TRAPS), hyper-IgD syndrome (HIDS), periodic fever, aphthous stomatitis, pharyngitis and adenitis (PFAPA), deficiency of interleukin-1 (IL-1) receptor antagonist (DIRA), etc; systemic inflammatory diseases such as systemic juvenile idiopathic arthritis, adult-onset Still's disease, Schnitzler syndrome, Behçet's disease, PFAPA (periodic fever, apthous stomatitis, pharyngitis, adenitis), SAPHO (synovitis, acne, pustulosis, hyperostosis, osteitis) syndrome, macrophage activation syndrome, etc; and common inflammatory diseases such as gout, type 1 diabetes, type 2 diabetes, metabolic syndrome, insulin resistance, stroke, heart attack, myocarditis, cardiac toxicity due to drug or radiation, ischemic heart disease, cardiomyopathy on a familial or genetic basis, heart failure, cardiac arrest and anoxic brain injury, acute and chronic lung injury due to infection, ischemia, toxin, trauma; dry eye syndrome, pustular psoriasis; neutrophilic dermatoses; acute or chronic hepatitis due a virus, toxin, ischemia or drug; acute or chronic renal injury due to ischemia, hypertension, diabetes, toxin or drugs and sepsis, septic shock.

In a preferred embodiment, the small molecule compounds are used to treat MS. MS refers to all types of MS, including relapse-remitting, secondary progressive, and primary progressive MS. The compounds are also used to treat all types of AD and other age-related neurodegenerative disorders.

The present invention provides compositions comprising the compounds described herein, and/or pharmaceutically acceptable salts of the compounds. The compositions are generally for use in preventing or treating inflammation, e.g., inflammation caused by formation and activity of NLRP3 inflammasomes. The compositions include one or more substantially purified compounds as described herein, and a pharmacologically suitable (compatible) carrier. The preparation of such compositions is known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. In addition, the compositions may contain other agents with different but complementary activities, e.g., other anti-inflammatory agents, analgesics, blood thinners, antihistamines, etc. If it is desired to administer an oral form of the compositions, various thickeners, flavorings, diluents, emulsifiers, dispersing aids or binders and the like may be added. The compositions of the present invention may contain any such additional ingredients so as to provide the composition in a form suitable for administration. The final amount of compound in the formulations may vary. However, in general, the amount in the formulations will be from about 1-99%. Still other suitable formulations for use in the present invention can be found, for example, in Remington's Pharmaceutical Sciences, Philadelphia, Pa., 19th ed. (1995).

As used herein, "pharmaceutically acceptable salts" refers to the relatively non-toxic, inorganic and organic acid addition salts, and base addition salts, of compounds of the present invention. These: salts can be prepared in situ during the final isolation and purification of the compounds. In particular, acid-addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

Precursors (generally inactive precursors) of the compounds which are metabolized after administration to yield the compounds/active agents described herein in an active form are also encompassed.

The therapeutic agents described herein are used alone or in combination with other suitable agents, e.g. other agents that prevent or treat inflammation (for example, by another mechanism), including but not limited to: IL-1R antagonists such as anakinra; monoclonal antibodies against interleukin 1β such as canakinumab (Ilaris®); various interleukin 1 binding proteins such as rilonacept (Arcalyst®); and the like. Accordingly, the compositions provided herein may include one or more of these additional agents.

The compositions (preparations) of the present disclosure may be administered by any of the many suitable means which are well known to those of skill in the art, including but not limited to: by injection (e.g. intravenous, intraperitoneal, intramuscular, subcutaneous, intra-aural, intraarticular, intramammary, and the like), by absorption through epithelial or mucocutaneous linings (e.g., nasal, oral, vaginal, rectal, gastrointestinal mucosal linings, and the like), by inhalation, orally, intranasally, by ingestion of a food or probiotic product, topically (e.g. on areas such as eyes, skin, in ears or on inflamed areas), as eye drops, via sprays, incorporated into dressings or bandages (e.g., lyophilized forms may be included directly in the dressing), etc. Generally, the mode of administration is by injection so as to effect systemic distribution of the agent, or locally by direct application, via an appropriate means, at or near a site of inflammation or a site where inflammation is likely to occur.

The amount of a compound that is administered varies depending on several factors, including the disease or condition being treated, the stage of the disease, the overall health of the subject, the subject's age, gender and weight, etc. In general, the amount is in the range of from about 0.01 to about 100 mg/kg of body weight, and usually is in the range of from about 1 to about 20 mg/kg of body weight. The IC50 of small molecule compounds is provided in Example 15 and may be used as guidance for formulation of a pharmaceutical composition of the invention. The subjects (patients) that are treated as described herein are generally mammals, e.g. humans, but veterinary applications of this technology are also encompassed, e.g. for companion pets such as cats and dogs.

The compounds of the disclosure are utilized to inhibit, prevent and/or to treat conditions and/or diseases associated with or caused by NRLP3 inflammasome activity. The compounds of the invention are used to prevent or treat NRLP3 inflammasome-associated inflammation. By "inhibit" we mean that the small molecule compounds are administered to reduce or block NRLP3 inflammasome activity, thereby lessening or preventing the deleterious effects of NRLP3 inflammasome-associated inflammation. By "prevent" we mean that the compounds are administered prophylactically to a subject who is likely to develop the disease or condition, but before symptoms or indications of disease develop, or early in development. For example, subjects who have experienced MS may be treated as described herein in order to prevent subsequent adverse cardiac remodeling during the "second wave" of inflammation.

Alternatively, or in addition, the compounds may be administered in order to treat conditions/diseases that have already developed (e.g. when symptoms are already being exhibited, or when symptoms are observable or measurable). In this case, administration of the compounds ameliorates and may reverse the symptoms, or at least arrest the disease (e.g. prevent further disease development or progress). Those of skill in the art will recognize that while a goal of prevention or treatment may be to completely prevent or alleviate disease symptoms, much benefit can also accrue if symptoms not fully eradicated but are lessened, decreased or their onset is slowed, even though a full-blown cure is not effected.

Methods of treating NRLP3 inflammasome-related diseases are provided. Such methods may include a step of identifying a subject in need of such treatment (e.g. a subject with one or more symptoms of an NRLP3 inflammasome-related disorder, or a subject who is likely to develop such a disorder). For example, patients who have had MS may be treated as patients for whom there is reason to suspect the relapse of MS is likely to occur. The same is true for other conditions that are treated by the agents disclosed herein, i.e. a subject suitable for undergoing treatment may have one or more readily observable symptoms, or early symptoms, or a predisposition to development of the disease (e.g., genetically, due to life style, due to exposure to a substance that is known to cause inflammation, acquired due to environmental exposure to a toxin, or a combination of these factors) that is being treated.

As indicated above, the present invention inter alia provides the specified compounds for use in a method of inhibiting, preventing or treating NRLP3 inflammasome-associated inflammation, including neuroinflammations associated with MS or other inflammation-related diseases, as well as acute inflammation, or acute inflammatory response, which may occur in variety of illness in which an injury induces inflammation. For instance, TBI is known to induce an inflammatory cascade that compounds the initial injury to the head and brain tissue. Further, the present invention may provide the specified compound as an active therapeutic ingredient in the specified method. Further, the present invention may provide the specified compound for use in a method of treatment of the human or animal body by therapy, the method comprising the specified method.

Before exemplary embodiments of the present invention are described in greater detail, it is to be understood that this invention is not limited to any particular embodiments described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both limits, ranges excluding either or both of those included limits are also included in the invention. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES OF THE INVENTION

These Examples describe the materials and methods for using embodiments illustrated in FIGS. 1-5. Additional details of the Examples can be found in the section entitled "Brief Description of the Drawings". Structure-activity relationship (SAR) studies were conducted to understand the contributions of different structural features of the lead structure and to provide guidance for further structural optimization/refinement of this chemical scaffold.

Experimental Methods and Materials

Chemistry for Synthetic Methods.

Reagents and solvents were obtained from commercial suppliers and used as received unless otherwise indicated. All reactions were carried out under inert atmosphere (N2) unless otherwise noted. Reactions were monitored by thin-layer chromatography (TLC) (precoated silica gel 60 F254 plates, EMD Chemicals) and visualized with UV light or by treatment with Phosphomolybdic acid (PMA). Flash chromatography was performed on silica gel (200-300 mesh, Fisher Scientific) using solvents as indicated. $^1$HNMR and $^{13}$CNMR spectra were routinely recorded on Bruker ARX 400 spectrometer. The NMR solvent used was $CDCl_3$ or DMSO-$d_6$ as indicated. Tetramethylsilane (TMS) was used as internal standard. The purity of target compounds was determined by HPLC using Varian 100-5 C18 250×4.6 mm column with UV detection (230 nm) (60% acetonitrile/40% H2O/0.1% trifluoroacetic acid (TFA) and 80% methanol/19.9% H2O/0.1% TFA, two solvent systems) to be >95%.

Biological Assays

J774A.1 murine macrophage cells and hCMEC/D3 cells were purchased from American Type Cell Culture (ATCC, Manassas, VA). J774A.1 cells were cultured in Dulbecco's Modified Eagle Medium (DMEM) with 10% fetal bovine serum (FBS), 1% penicillin/streptomycin. hCMEC/D3 cells were cultured using Endothelial Growth medium-2 (EGM-2) supplemented with a Bullet Kit™. The medium was supplemented with 10 mM HEPES (5 mL), 1× penicillin-streptomycin (5 mL), and 1 ng/mL of bFGF (2.5 mL) at 5% CO2, 37° C. and 95% relative humidity. This media was termed as growth media. EGM-2 media supplemented with 10 mM HEPES (5 mL), 1x penicillin-streptomycin (5 mL), 2.5% FBS, and 1 ng/mL of bFGF (1.25 mL) was termed as maintenance media Animals All animal experiments were conducted under the guidelines of the "Guide for the care and use of laboratory animals" published by National Institutes of Health (revised 2011). C57BL/6 male mice were purchased from the National Cancer Institute (Bethesda, MD). Nlrp3−/− male mice on C57BL/6 background and male Sprague-Dawley rats were purchased from the Jackson Laboratory (Bar Harbor, ME).

Example 1. Synthesis of 4-(2-(1,3-dioxoisoindolin-2-yl)ethyl)-N-(prop-2-yn-1-yl)benzenesulfonamide (30)

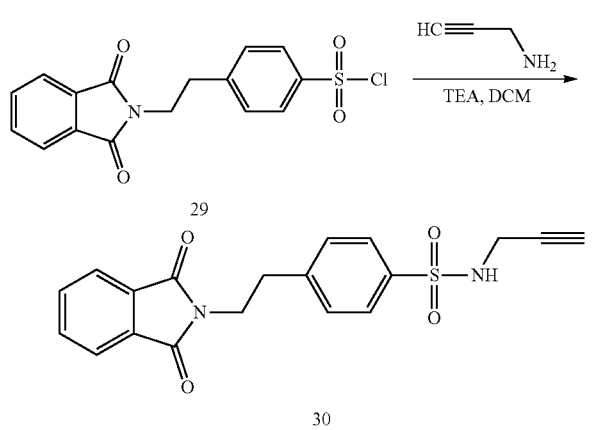

Propargylamine (1.1 g, 20.0 mmol) and TEA (2.8 mL, 20.0 mmol) were dissolved in anhydrous acetonitrile (100 mL) under ice bath followed by the addition of 29, synthetized following previously reported procedures (3.5 g, 10.0 mmol). The mixture was stirred for 4 h at room temperature (rt). The solvent was evaporated and the residue was dissolved in dichloromethane (DCM, 20 mL). The DCM solution was washed with water for 3 times, dried over anhydrous $Na_2SO_4$ and evaporated under vacuum. The crude product was purified by chromatography using DCM-Methanol (100:1) as the mobile phase, to obtain 30 as a white solid (2.9 g, yield: 78%). $^1$H NMR (400 MHz CDCl3): δ 3.04 (t, J=7.44 Hz, 2H), 3.74-3.76 (m, 2H), 3.91 (t, J=7.32 Hz, 2H), 4.67 (s, 1H), 7.31-7.39 (m, 2H), 7.63-7.77 (m, 6H).

Example 2. Synthesis of 4-(2-aminoethyl)-N-(prop-2-yn-1-yl)benzenesulfonamide (31)

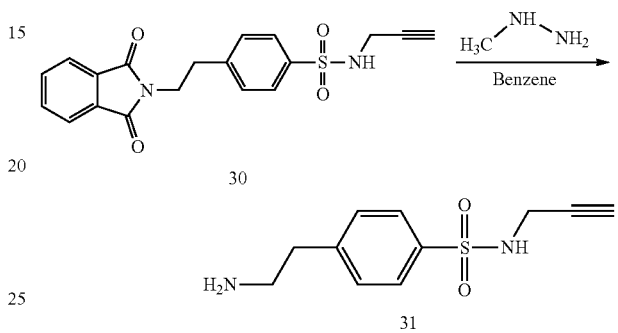

30 (1.3 g, 3.5 mmol) was dissolved in anhydrous benzene (15 mL) and then methylhydrazine (1.8 mL) was added. The reaction was stirred at r.t. for 12 h. After removing the benzene, the crude product was purified by chromatography using DCM-Methanol (100:5) to get 31 as an oil (0.41 g, yield: 49%). 1H-NMR (400 MHz MeOD): δ 2.47 (d, J=2.56 Hz, 1H), 2.84-2.95 (m, 4H), 3.76 (d, J=2.52 Hz, 2H), 7.44 (d, J=8.32 Hz, 2H), 7.83 (d, J=8.36 Hz, 2H).

Example 3. Synthesis of 5-chloro-2-methoxybenzaldehyde (33)

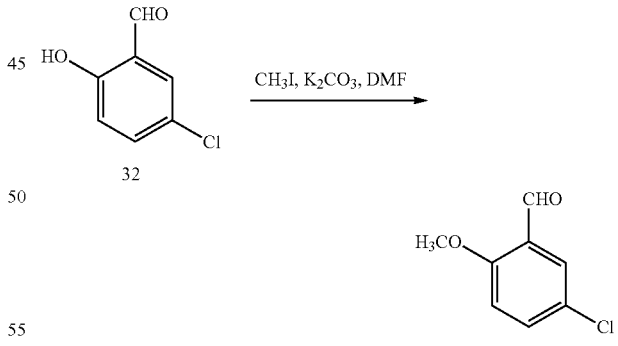

A mixture of 5-chloro-2-hydroxy benzaldehyde (0.63 g, 4.0 mmol), iodomethane (0.74 g, 5.2 mmol) and K2CO3 (1.1 g, 8.0 mmol) in dimethylformamide (DMF, 30 mL) was stirred at rt for 48 h. The DMF was evaporated under reduced pressure and the residue was taken up to DCM (30 mL). The DCM solution was washed with water for 3 times, dried over anhydrous Na2SO4, filtered and evaporated to obtain 33 as yellow solid and was used in the next step without any further purification. 1H-NMR (400 MHz DMSO-d6): δ 3.94 (s, 3H), 7.31 (d, J=8.96 Hz, 1H), 7.63 (d, J=2.80 Hz, 1H), 7.73 (dd, J1=2.84 Hz, J2=8.96 Hz, 1H), 10.29 (s, 1H).

Example 4. 4-(2-((5-chloro-2-methoxybenzyl)amino)ethyl)-N-(prop-2-yn-1-yl)benzenesulfonamide (34)

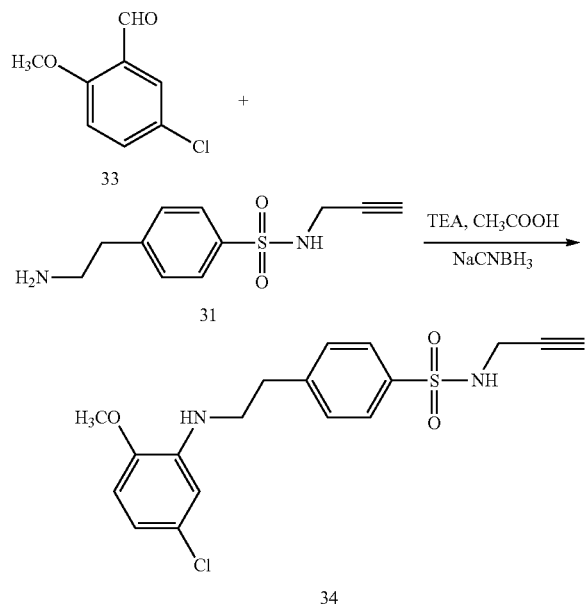

The solution of compound 33 (1.7 g, 10.0 mmol), 31 (2.6 g, 11.0 mmol) and TEA (1.5 mL, 11.0 mmol) in methanol (50 mL) was stirred at rt for 1 h at. Then acetic acid (0.6 mL) was added and the mixture was stirred at rt for another 1 h. NaCNBH3 (0.87 g, 13.0 mmol) in methanol was added portion wise under ice bath. Then, the reaction was stirred at rt for 12 h. After removing the solvents, the residue was taken up to DCM (50 mL). The DCM layer was washed with brine for 3 times, dried over anhydrous Na2SO4 and evaporated under vacuum. The crude produce was purified by chromatography using DCM-Methanol (100:1.5) to get 34 as oil (2.4 g, yield: 61%). 1H-NMR (400 MHz CDCl3): δ 2.03 (t, J=2.56 Hz, 1H), 2.85-2.89 (m, 4H), 3.68 (s, 3H), 3.75-3.77 (m, 4H), 6.70 (d, J=8.56 Hz, 1H), 7.11-7.15 (m, 2H), 7.28 (d, J=8.36 Hz, 2H), 7.75 (d, J=8.36 Hz, 2H).

Example 5. Synthesis of N-(5-chloro-2-methoxybenzyl)-N-(4-(N-(prop-2-yn-1-yl)sulfamoyl)phenethyl)acryl-amide (2)

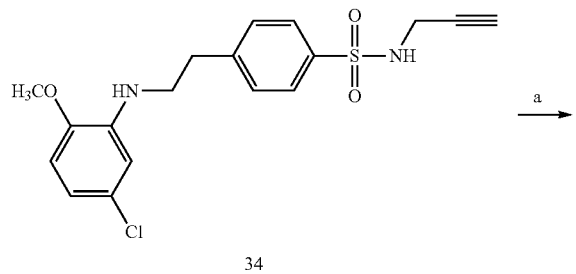

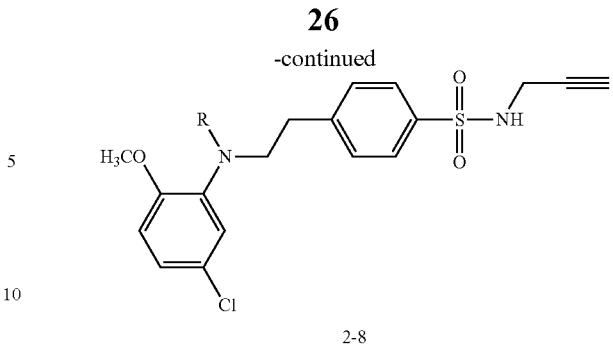

2-8 wherein R is unbranched, branched, saturated, unsaturated, cyclic or acyclic, substituted or unsubstituted C1-C8 alkyl-carbonyl; substituted or unsubstituted aryl or heteroarylcarbonyl; C1-C8 unbranched, branched, saturated, unsaturated, cyclic or acyclic, substituted or unsubstituted alkyl, or H;

Reagents and conditions: various acids, EDCI, HOBt, TEA, DCM; For 7 and 8: K2CO3, DMF.

Acrylic acid (0.03 g, 0.4 mmol) and HOBt (0.068 g, 0.5 mmol) were dissolved in anhydrous DCM (20 mL) under ice bath followed by the addition of EDCI (0.096 g, 0.5 mmol). The mixture was stirred at rt for 30 min. Compound 34 (0.20 g, 0.5 mmol) and TEA (0.07 mL) in DCM (30 mL) were added directly. The reaction was stirred at r.t. for 3 h. Then DCM solution was washed with 1N HCl, saturated NaHCO3 and brine for 3 times, dried over anhydrous Na2SO4 and evaporated under vacuum. The crude product was purified by chromatography using EtOAc-Hexane (1:1) as the mobile phase, to obtain 2 as a white solid (0.088 g, yield: 47%). 1H-NMR (400 MHz CDCl3): δ 2.03-2.04 (m, 1H), 2.84-2.91 (m, 2H), 3.51-3.58 (m, 2H), 3.74-3.76 (m, 5H), 4.37-4.55 (m, 2H), 4.89-4.91 (m, 1H), 5.60-5.64 (m, 1H), 6.31-6.45 (m, 2H), 6.74 (d, J=8.68 Hz, 1H), 6.92 (d, J=2.52 Hz, 1H), 7.09-7.22 (m, 2H), 7.27 (d, J=8.24 Hz, 1H), 7.72-7.77 (m, 2H). $^{13}$C NMR (100 MHz, CDCl$_3$): δ 167.1, 156.0, 144.8, 138.3, 129.5, 129.2, 128.7, 128.3, 127.8, 127.6, 127.3, 126.6, 125.9, 111.5, 77.9, 73.1, 55.8, 48.7, 33.8, 32.9, 29.7. HRMS (AP-ESI) m/z calcd for C22H23ClN2O4S [M+Na]$^+$ 469.0965, found 469.1003.

Examples of Compounds

N-(5-chloro-2-methoxybenzyl)-N-(4-(N-(prop-2-yn-1-yl)sulfamoyl)phenethyl)propion-amide (3)

Compound 3 was prepared from propanoic acid and 34 following the procedure of example 5 in 55% yield. 1H-NMR (400 MHz DMSO-d6): δ 0.93-0.98 (m, 3H), 2.24-2.36 (m, 2H), 2.82 (t, J=7.44 Hz, 1H), 2.95 (t, J=7.52 Hz, 1H), 3.03-3.05 (m, 1H), 3.49 (t, J=7.36 Hz, 1H), 3.54 (t, J=7.48 Hz, 1H), 3.64-3.66 (m, 2H), 3.82 (d, J=5.12 Hz, 3H), 4.44 (d, J=8.32 Hz, 2H), 6.98-7.07 (m, 2H), 7.27-7.36 (m, 1H), 7.39 (d, J=8.16 Hz, 1H), 7.47 (d, J=8.20 Hz, 1H), 7.70-7.74 (m, 2H), 8.05-8.10 (m, 1H). $^{13}$C NMR (100 MHz, DMSO-d6): δ 173.1, 155.7, 144.3, 138.3, 129.5, 129.3, 128.1, 127.5, 127.0, 126.8, 126.5, 124.2, 112.6, 79.3, 74.6, 55.7, 48.5, 46.9, 34.1, 31.9, 25.4, 9.4. HRMS (AP-ESI) m/z calcd for C22H25ClN2O4S [M+Na]$^+$ 471.1121, found 471.1156.

N-(5-chloro-2-methoxybenzyl)-N-(4-(N-(prop-2-yn-1-yl)sulfamoyl)phenethyl)hexanamide (4)

Compound 4 was prepared from hexanoic acid and 34 following the procedure of example 5 in 62% yield.

1H-NMR (400 MHz DMSO-d6): δ 0.82-0.88 (m, 3H), 1.18-1.29 (m, 4H), 1.43-1.48 (m, 2H), 2.26 (t, J=7.32 Hz, 2H), 2.83 (t, J=7.68 Hz, 1H), 2.94 (t, J=7.32 Hz, 1H), 3.03-3.05 (m, 1H), 3.50 (t, J=7.40 Hz, 1H), 3.56 (t, J=7.28 Hz, 1H), 3.64-3.66 (m, 2H), 3.82 (d, J=3.92 Hz, 3H), 4.44 (d, J=7.40 Hz, 2H), 6.99 (dd, J1=2.68 Hz, J2=9.48 Hz, 1H), 7.01-7.07 (m, 1H), 7.27-7.37 (m, 1H), 7.40 (d, J=8.32 Hz, 1H), 7.46 (d, J=8.36 Hz, 1H), 7.70-7.75 (m, 2H), 8.05-8.10 (m, 1H). $^{13}$C NMR (100 MHz, DMSO-d6): δ 172.4, 155.7, 144.3, 138.4, 129.6, 129.3, 128.1, 127.6, 126.9, 126.8, 124.2, 112.6, 79.3, 74.6, 55.7, 48.5, 46.9, 34.1, 31.9, 31.6, 30.9, 24.5, 22.0, 13.9. HRMS (AP-ESI) m/z calcd for C25H31ClN2O4S [M+Na]$^+$ 513.1591, found 513.1599.

N-(5-chloro-2-methoxybenzyl)-2-phenyl-N-(4-(N-(prop-2-yn-1-yl)sulfamoyl)phenethyl)aceamide (5)

Compound 5 was prepared from 2-phenyl acetic acid and 34 following the procedure of example 5 in 69% yield. 1H-NMR (400 MHz DMSO-d6): δ 2.83 (t, J=7.20 Hz, 1H), 2.89 (t, J=7.56 Hz, 1H), 3.02-3.03 (m, 1H), 3.49 (t, J=7.00 Hz, 1H), 3.58 (t, J=7.00 Hz, 1H), 3.64-3.69 (m, 4H), 3.82 (d, J=2.72 Hz, 3H), 4.47 (d, J=8.88 Hz, 2H), 6.99 (dd, J1=2.64 Hz, J2=16.64 Hz, 1H), 7.07 (dd, J1=8.80 Hz, J2=17.36 Hz, 1H), 7.13-7.36 (m, 7H), 7.45 (d, J=8.40 Hz, 1H), 7.69 (d, J=8.28 Hz, 1H), 7.76 (d, J=8.83 Hz, 1H), 8.05-8.11 (m, 1H). $^{13}$C NMR (100 MHz, DMSO-d6): δ 170.6, 155.8, 144.1, 138.5, 135.7, 129.6, 129.3, 129.0, 128.9, 128.3, 127.8, 127.6, 127.2, 126.9, 126.4, 124.3, 112.7, 79.3, 74.6, 55.8, 48.9, 46.7, 42.8, 34.1, 31.9. HRMS (AP-ESI) m/z calcd for C27H27ClN2O4S [M+Na]$^+$ 533.1278, found 533.1285.

N-(5-chloro-2-methoxybenzyl)-N-(4-(N-(prop-2-yn-1-yl)sulfamoyl)phenethyl)-2-(thiophen-3-yl)acetamide (6)

Compound 6 was prepared from thiophene-3-yl-acetic acid and 34 following the procedure of example 5 in 57% yield. 1H-NMR (400 MHz DMSO-d6): δ 2.79-2.89 (m, 2H), 3.02-3.04 (m, 1H), 3.47 (t, J=7.56 Hz, 1H), 3.59 (t, J=7.40 Hz, 1H), 3.64-3.69 (m, 4H), 3.81 (s, 3H), 4.46 (d, J=4.68 Hz, 2H), 6.93-7.07 (m, 3H), 7.25-7.29 (m, 3H), 7.44-7.50 (m, 2H), 7.70 (d, J=8.32 Hz, 1H), 7.75 (d, J=8.32 Hz, 1H), 8.05-8.10 (m, 1H). 13C NMR (100 MHz, DMSO-d6): δ 170.3, 155.7, 144.1, 138.5, 135.5, 129.6, 129.2, 128.6, 128.2, 127.7, 127.2, 127.0, 126.8, 125.9, 124.3, 122.4, 112.7, 79.3, 74.6, 55.8, 48.9, 46.7, 34.6, 34.3, 31.9. HRMS (AP-ESI) m/z calcd for C25H25ClN2O4S2 [M+Na]$^+$ 539.0842, found 539.0866.

Example 6. Synthesis of 4-(2-(allyl(5-chloro-2-methoxybenzyl)amino)ethyl)-N-(prop-2-yn-1-yl)benzenesulfonamide (7)

A mixture of 34 (0.2 g, 0.5 mmol) and K$_2$CO$_3$ (0.14 g, 1.0 mmol) in DMF was stirred at room temperature. Then allyl bromide (0.06 g, 0.5 mmol) was added and the mixture was stirred at room temperature for 6 h. After removing DMF under reduced pressure, the residue was taken up to DCM. The DCM solution was washed with water for 3 times, dried over anhydrous Na2SO4, filtered and evaporated. The crude product was purified by chromatography using EtOAc-Hexane (1:1) as the mobile phase, to obtain 7 as a white solid (0.058 g, yield: 27%). 1H-NMR (400 MHz DMSO-d6): δ 2.78-2.84 (m, 4H), 3.06 (t, J=2.48 Hz, 1H), 3.69 (s, 2H), 3.76-3.80 (m, 5H), 4.03 (d, J=2.52 Hz, 2H), 5.19-5.28 (m, 2H), 5.66-5.76 (m, 1H), 6.98 (d, J=8.76 Hz, 1H), 7.26 (dd, J1=2.72 Hz, J2=8.68 Hz, 1H), 7.31 (d, J=2.76 Hz, 1H), 7.46 (d, J=8.32 Hz, 2H), 7.76 (d, J=8.36 Hz, 2H). 13C NMR (100 MHz, DMSO-d6): δ 155.7, 146.3, 136.0, 132.2, 130.6, 129.4, 128.1, 127.3, 127.1, 123.9, 119.4, 112.1, 76.9, 76.2, 55.6, 49.7, 48.9, 46.6, 36.0, 35.4. HRMS (AP-ESI) m/z calcd for C22H25ClN2O3S [M+H]$^+$ 433.1347, found 433.1338.

Examples of Compounds 4-(2-((5-chloro-2-methoxybenzyl)(propyl)amino)ethyl)-N-(prop-2-yn-1-yl)benzenesulfonamide (8)

Compound 8 was prepared from 1-bromopropane and 34 following the procedure of example 6 in 21% yield. 21% yield. 1H-NMR (400 MHz DMSO-d6): δ 0.86 (t, J=7.36 Hz, 3H), 1.48-1.57 (m, 2H), 2.78-2.83 (m, 4H), 3.04-3.09 (m, 3H), 3.68 (s, 2H), 3.76 (s, 3H), 4.09 (d, J=2.48 Hz, 2H), 6.98 (d, J=8.72 Hz, 1H), 7.26 (dd, J1=2.76 Hz, J2=8.68 Hz, 1H), 7.31 (d, J=2.76 Hz, 1H), 7.45 (d, J=8.36 Hz, 2H), 7.73 (d, J=8.32 Hz, 2H). 13C NMR (100 MHz, DMSO-d6): δ 155.7, 146.1, 136.1, 130.6, 129.3, 128.1, 127.2, 127.1, 123.9, 112.1, 77.5, 75.9, 55.6, 49.7, 48.2, 46.6, 36.2, 35.4, 20.4, 10.9. HRMS (AP-ESI) m/z calcd for C22H27ClN2O3S [M+H]$^+$ 435.1503, found 435.1457.

5-chloro-2-propoxybenzaldehyde (35)

Compound 35 was synthetized from 1-Bromopropane (1.3 g, 11.0 mmol) and 5-chloro-2-hydroxy benzaldehyde (1.6 g, 10.0 mmol) following the procedure of example 3M 90% yield. 1H-NMR (400 MHz DMSO-d6): δ 1.03 (t, J=7.40 Hz, 3H), 1.75-1.84 (m, 2H), 4.12 (t, J=6.40 Hz, 2H), 7.29 (d, J=8.92 Hz, 1H), 7.62 (d, J=2.80 Hz, 1H), 7.69 (dd, J1=2.84 Hz, J2=8.96 Hz, 1H), 10.33 (s, 1H).

4-(2-((5-chloro-2-propoxybenzyl)amino)ethyl)-N-(prop-2-yn-1-yl)benzenesulfonamide (36)

Compound 36 was synthetized from compound 35 (2.0 g, 10.0 mmol) and compound 31 (2.6 g, 11.0 mmol) following the procedure to example 4 in 43% yield. 1H-NMR (400 MHz DMSO-d6): δ 0.97 (t, J=7.68 Hz, 3H), 1.64-1.73 (m, 2H), 2.81-2.84 (m, 4H), 3.05 (t, J=2.52 Hz, 1H), 3.65-3.66 (m, 2H), 3.72 (s, 2H), 3.92 (t, J=6.36 Hz, 2H), 6.97 (d, J=8.72 Hz, 1H), 7.25 (dd, J1=2.76 Hz, J2=8.68 Hz, 1H), 7.33 (d, J=2.72 Hz, 1H), 7.43 (d, J=8.36 Hz, 2H), 7.72 (d, J=8.36 Hz, 2H), 8.05 (s, 1H).

N-(5-chloro-2-propoxybenzyl)-N-(4-(N-(prop-2-yn-1-yl)sulfamoyl)phenethyl)acrylamide (9)

Compound 9 was synthetized from acrylic acid and compound 36 following the procedure of example 5 in 58% yield. 1H-NMR (400 MHz DMSO-d6): δ 0.95-1.00 (m, 3H), 1.70-1.76 (m, 2H), 2.86 (t, J=7.64 Hz, 1H), 2.93 (t, J=7.68 Hz, 1H), 3.02-3.04 (m, 1H), 3.54-3.69 (m, 4H), 3.98 (t, J=6.44 Hz, 2H), 4.44-4.53 (m, 2H), 5.63-5.69 (m, 1H), 6.09-6.20 (m, 1H), 6.65-6.76 (m, 1H), 6.99-7.10 (m, 2H), 7.26-7.46 (m, 3H), 7.73 (d, J=8.16 Hz, 2H), 8.04-8.06 (m, 1H). 13C NMR (100 MHz, DMSO-d6): δ 165.6, 155.2, 144.1, 138.4, 129.6, 129.2, 128.3, 127.9, 127.8, 127.3, 126.8, 123.9, 113.4, 79.3, 74.6, 69.6, 48.4, 47.2, 34.7, 31.9, 21.9, 10.5. HRMS (AP-ESI) m/z calcd for C24H27ClN2O4S [M+Na]$^+$ 497.1277, found 497.1248.

N-(5-chloro-2-propoxybenzyl)-2-phenyl-N-(4-(N-(prop-2-yn-1-yl)sulfamoyl)phenethyl)acetamide (10)

Compound 10 was prepared from 2-phenylacetic acid and 36 following the procedure of example 5 in 49% yield as a white solid. 1H-NMR. (400 MHz DMSO-d6): δ 0.93-0.99 (m, 3H), 1.70-1.73 (m, 2H), 2.80 (t, J=7.52 Hz, 1H), 2.87 (t, J=7.44 Hz, 1H), 3.01-3.02 (m, 1H), 3.45-3.49 (m, 1H), 3.60 (t, J=7.56 Hz, 1H), 3.64-3.68 (m, 4H), 3.92-3.98 (m, 2H), 4.46 (t, J=14.96 Hz, 2H), 6.98-7.05 (m, 2H), 7.13-7.33 (m, 7H), 7.42 (d, J=8.16 Hz, 1H), 7.68 (d, J=8.32 Hz, 1H), 7.74 (d, J=8.32 Hz, 1H), 8.05-8.08 (m, 1H). 13C NMR (100 MHz, DMSO-d6): δ 170.5, 155.2, 144.1, 138.5, 135.7, 129.5, 129.2, 129.1, 128.9, 128.3, 127.9, 127.6, 127.3, 126.8, 126.4, 124.1, 113.4, 79.3, 74.6, 69.5, 48.8, 46.6, 42.9, 34.1, 31.9, 21.9, 10.5. HRMS (AP-ESI) m/z calcd for C29H31ClN2O4S [M+Na]+ 561.1591, found 561.1595.

N-(5-chloro-2-propoxybenzyl)-2-(4-methoxyphenyl)-N-(4-(N-(prop-2-yn-1-yl)sulfamoyl)phenethyl) acetamide (11)

Compound 11 was prepared from 2-(4-methoxy)-phenylacetic acid and 36 following the procedure of example 5 in 51% yield as a white solid. 1H-NMR (400 MHz DMSO-d6): δ 0.95-1.00 (m, 3H), 1.71-1.76 (m, 2H), 2.85 (t, J=7.52 Hz, 1H), 2.97 (t, J=7.40 Hz, 1H), 3.02-3.03 (m, 1H), 3.51 (t, J=6.96 Hz, 1H), 3.57-3.67 (m, 5H), 3.72-3.77 (m, 3H), 3.94-3.99 (m, 2H), 4.45 (d, J=4.00 Hz, 2H), 6.87-7.10 (m, 5H), 7.20-7.31 (m, 2H), 7.37 (d, J=8.20 Hz, 1H), 7.45 (d, J=8.24 Hz, 1H), 7.71 (d, J=8.32 Hz, 1H), 7.77 (d, J=8.28 Hz, 1H), 8.03-8.09 (m, 1H). 13C NMR (100 MHz, DMSO-d6): δ 170.7, 156.7, 155.0, 144.2, 138.5, 130.6, 130.4, 129.5, 129.2, 128.1, 127.9, 127.5, 127.0, 126.8, 124.3, 123.9, 120.2, 113.3, 110.6, 79.3, 74.6, 69.6, 55.4, 49.0, 47.1, 43.2, 34.3, 31.9, 21.9, 10.5. HRMS (AP-ESI) m/z calcd for C30H33ClN2O5S [M+Na]+ 591.1696, found 591.1656.

N-(5-chloro-2-propoxybenzyl)-3-phenyl-N-(4-(N-(prop-2-yn-1-yl)sulfamoyl)phenethyl)propan-amide (12)

Compound 12 was prepared from 3-phenylpropanoic acid and 36 following the procedure of example 5 in 55% yield as a white solid. 1H-NMR (400 MHz DMSO-d6): δ 0.90-0.99 (m, 3H), 1.64-1.75 (m, 2H), 2.57-2.64 (m, 2H), 2.76-2.88 (m, 4H), 3.01-3.05 (m, 1H), 3.49 (t, J=7.40 Hz, 1H), 3.55 (t, J=7.32 Hz, 1H), 3.63-3.66 (m, 2H), 3.91-3.96 (m, 2H), 4.38-4.44 (m, 2H), 6.99-7.04 (m, 2H), 7.16-7.32 (m, 6H), 7.35 (d, J=8.36 Hz, 1H), 7.40 (d, J=8.32 Hz, 1H), 7.69-7.73 (m, 2H), 8.05-8.10 (m, 1H). 13C NMR (100 MHz, DMSO-d6): δ 171.6, 155.1, 144.2, 141.3, 138.4, 129.5, 129.2, 128.3, 128.2, 128.1, 127.7, 127.4, 127.3, 126.8, 125.8, 124.0, 113.4, 79.3, 74.6, 69.6, 48.3, 46.9, 34.1, 33.4, 31.9, 30.7, 21.9, 10.5. HRMS (AP-ESI) m/z calcd for C30H33ClN2O4S [M+Na]+ 575.1747, found 575.1750.

N-(5-chloro-2-propoxybenzyl)-N-(4-(N-(prop-2-yn-1-yl)sulfamoyl)phenethyl)-2-(pyridin-4-yl)acetamide (13)

Compound 13 was prepared from 2-(pyridine-4-yl)acetic acid and 36 following the procedure of example 5 in 41% yield as a white solid. 1H-NMR (400 MHz DMSO-d6): δ 0.99-1.05 (m, 3H), 1.75-1.81 (m, 2H), 2.88 (t, J=7.52 Hz, 1H), 3.02 (t, J=7.40 Hz, 1H), 3.08 (t, J=2.48 Hz, 1H), 3.52-3.56 (m, 1H), 3.66-3.71 (m, 3H), 3.78-3.83 (m, 2H), 3.99-4.05 (m, 2H), 4.53 (s, 2H), 7.05-7.15 (m, 2H), 7.20-7.23 (m, 2H), 7.29-7.33 (m, 1H), 7.40 (d, J=8.16 Hz, 1H), 7.53 (d, J=8.32 Hz, 1H), 7.76 (d, J=8.24 Hz, 1H), 7.82 (d, J=8.28 Hz, 1H), 8.11-8.14 (m, 1H), 8.51-8.54 (m, 2H). 13C NMR (100 MHz, DMSO-d6): δ 169.4, 156.6, 155.2, 149.3, 144.8, 144.0, 138.6, 129.6, 129.2, 128.4, 127.7, 127.0, 126.8, 124.9, 124.6, 124.1, 113.4, 79.3, 74.6, 69.6, 48.7, 47.5, 46.7, 34.3, 31.9, 21.9, 10.5. HRMS (AP-ESI) m/z calcd for C28H30ClN3O4S [M+Na]+ 562.1543, found 562.1579.

N-(5-chloro-2-propoxybenzyl)-N-(4-(N-(prop-2-yn-1-yl)sulfamoyl)phenethyl)-2-(pyri-din-2-yl)acetamide (14)

Compound 14 was prepared from 2-(pyridine-2-yl)acetic acid and 36 following the procedure of example 5 in 43% yield as a white solid. 1H-NMR (400 MHz DMSO-d6): δ 0.94-1.00 (m, 3H), 1.69-1.77 (m, 2H), 2.81 (t, J=7.48 Hz, 1H), 2.96 (t, J=7.40 Hz, 1H), 3.08 (t, J=2.52 Hz, 1H), 3.49 (t, J=7.40 Hz, 1H), 3.63-3.67 (m, 3H), 3.87 (d, J=9.08 Hz, 2H), 3.93-3.97 (m, 2H), 4.46-4.52 (m, 2H), 6.97-7.34 (m, 6H), 7.46 (d, J=8.40 Hz, 1H), 7.66-7.78 (m, 3H), 8.04-8.09 (m, 1H), 8.54-8.56 (m, 1H). 13C NMR (100 MHz, DMSO-d6): δ 169.9, 156.2, 155.1, 148.9, 144.1, 138.5, 136.6, 129.5, 129.2, 128.2, 127.8, 127.4, 127.3, 126.9, 124.1, 123.9, 121.9, 113.4, 79.3, 74.6, 69.6, 49.2, 46.7, 42.3, 34.3, 31.9, 21.9, 10.5. HRMS (AP-ESI) m/z calcd for C28H30ClN3O4S [M+Na]+ 562.1543, found 562.1566.

N-(5-chloro-2-propoxybenzyl)-2-(1H-indol-3-yl)-N-(4-(N-(prop-2-yn-1-yl)sulfamoyl)-phenethyl)acetamide (15)

Compound 15 was prepared from 2-(indole-3-yl)acetic acid and 36 following the procedure of example 5 in 25% yield as a white solid. 1H-NMR (400 MHz DMSO-d6): δ 0.92-0.99 (m, 3H), 1.69-1.73 (m, 2H), 2.74-2.80 (m, 2H), 2.99-3.02 (m, 1H), 3.48 (t, J=7.56 Hz, 1H), 3.61 (t, J=7.51 Hz, 1H), 3.63-3.66 (m, 2H), 3.71-3.76 (m, 2H), 3.92-3.97 (m, 2H), 4.46-4.48 (m, 2H), 6.96-7.32 (m, 8H), 7.37 (d, J=8.12 Hz, 1H), 7.52 (t, J=7.60 Hz, 1H), 7.65 (d, J=8.28 Hz, 1H), 7.72 (d, J=8.28 Hz, 1H), 7.96-8.08 (m, 1H), 10.90-10.95 (m, 1H). $^{13}$C NMR (100 MHz, DMSO-d6): δ 171.1, 155.2, 144.2, 138.4, 136.1, 129.4, 129.2, 128.1, 127.5, 127.4, 127.1, 127.0, 126.8, 124.1, 123.5, 121.1, 118.5, 113.4, 111.4, 108.1, 79.3, 74.5, 69.6, 49.1, 46.9, 34.2, 33.0, 31.9, 21.9, 10.4. HRMS (AP-ESI) m/z calcd for C31H32ClN3O4S [M+Na]+ 600.1699, found 600.1695.

N-(5-chloro-2-propoxybenzyl)-2-(1H-imidazol-4-yl)-N-(4-(N-(prop-2-yn-1-yl)sulfamoyl)phenethyl) acetamide (16)

Compound 16 was prepared from 2-(imidazole-4-yl)acetic acid and 36 following the procedure of example 5 in 35% yield as a white solid. 1H-NMR (400 MHz DMSO-d6): δ 0.94-1.00 (m, 3H), 1.70-1.78 (m, 2H), 2.75-2.79 (m, 2H), 3.02-3.04 (m, 1H), 3.38-3.45 (m, 1H), 3.56-3.72 (m, 5H), 3.93-3.98 (m, 2H), 4.43-4.53 (m, 2H), 6.83-6.87 (m, 1H), 7.03-7.11 (m, 2H), 7.24 (dd, J1=2.68 Hz, J2=8.72 Hz 1H), 7.30-7.32 (m, 1H), 7.45 (d, J=8.36 Hz, 1H), 7.54-7.57 (m, 1H), 7.68 (d, J=8.36 Hz, 1H), 7.74 (d, J=8.36 Hz, 1H), 8.05-8.08 (m, 1H), 11.09 (s, 1H). $^{13}$C NMR (100 MHz, DMSO-d6): δ 170.2, 155.0, 144.2, 138.4, 134.8, 129.5, 129.2, 128.2, 127.9, 127.4, 127.3, 126.8, 124.1, 113.4, 79.3, 74.6, 69.5, 49.2, 46.8, 34.2, 32.9, 31.9, 21.9, 10.5. HRMS (AP-ESI) m/z calcd for C26H29ClN4O4S [M+Na]+ 551.1495, found 551.1471.

N-(5-chloro-2-propoxybenzyl)-N-(4-(N-(prop-2-yn-1-yl)sulfamoyl)phenethyl)-2-(thio-phen-3-yl)acetamide (17)

Compound 17 was prepared from 2-(thiophene-3-yl)acetic acid and 36 following the procedure of example 5 in 61% yield as a white solid. 1H-NMR (400 MHz DMSO-d6): δ 0.93-0.99 (m, 3H), 1.69-1.74 (m, 2H), 2.80 (t, J=7.58 Hz, 1H), 2.88 (t, J=7.48 Hz, 1H), 3.01-3.03 (m, 1H), 3.46 (t, J=7.48 Hz, 1H), 3.60 (t, J=7.68 Hz, 1H), 3.63-3.71 (m, 4H), 3.92-3.97 (m, 2H), 4.48 (d, J=8.28 Hz, 2H), 6.93-7.04 (m, 3H), 7.18-7.33 (m, 3H), 7.43 (d, J=7.88 Hz, 1H), 7.46-7.49 (m, 1H), 7.68 (d, J=7.88 Hz, 1H), 7.74 (d, J=7.88 Hz, 1H), 8.04-8.09 (m, 1H). $^{13}$C NMR (100 MHz, DMSO-d6): δ 170.2, 155.2, 144.1, 138.5, 135.5, 129.5, 129.2, 128.6, 128.3, 127.9, 127.6, 127.4, 126.8, 125.9, 124.1, 122.4, 113.4, 79.3, 74.6, 69.5, 48.9, 46.6, 34.8, 34.3, 31.9, 21.9, 10.5. HRMS (AP-ESI) m/z calcd for C27H29ClN2O4S2 [M+Na]+ 567.1155, found 567.1177.

N-(5-chloro-2-propoxybenzyl)-N-(4-(N-(prop-2-yn-1-yl)sulfamoyl)phenethyl)furan-3-carboxamide (18)

Compound 18 was prepared from 2-(furan-3-yl)acetic acid and 36 following the procedure of example 5 in 53% yield as a white solid. 1H-NMR (400 MHz DMSO-d6): δ 0.91-0.98 (m, 3H), 1.67-1.72 (m, 2H), 2.86-2.92 (m, 2H), 3.03 (t, J=2.52 Hz, 1H), 3.58-3.66 (m, 4H), 3.95-4.04 (m, 2H), 4.59 (s, 2H), 6.53-6.62 (m, 1H), 7.05 (d, J=8.84 Hz, 1H), 7.12-7.18 (m, 1H), 7.32-7.40 (m, 3H), 7.69-7.72 (m, 3H), 7.89-7.99 (m, 1H), 8.08 (t, J=5.92 Hz, 1H). $^{13}$C NMR (100 MHz, DMSO-d6): δ 164.2, 155.2, 150.7, 145.9, 143.4, 138.4, 129.3, 128.4, 128.2, 127.9, 127.3, 126.8, 124.0, 120.9, 113.4, 110.2, 79.3, 74.5, 69.6, 50.0, 47.4, 34.2, 31.9, 21.9, 10.4. HRMS (AP-ESI) m/z calcd for C26H27ClN2O5S [M+Na]+ 537.1227, found 537.1219.

N-(5-chloro-2-propoxybenzyl)-N-(4-(N-(prop-2-yn-1-yl)sulfamoyl)phenethyl)thio-phene-3-carboxamide (19)

Compound 19 was prepared from 3-thiophene carboxylic acid and 36 following the procedure of example 5 in 48% yield as a white solid. 1H-NMR (400 MHz DMSO-d6): δ 0.86-0.99 (m, 3H), 1.63-1.74 (m, 2H), 2.91-3.02 (m, 3H), 3.59 (t, J=7.44 Hz, 2H), 3.65 (s, 2H), 3.91-3.98 (m, 2H), 4.47-4.64 (m, 2H), 7.03-7.33 (m, 5H), 7.42 (s, 1H), 7.59-7.71 (m, 4H), 8.07 (s, 1H). 13C NMR (100 MHz, DMSO-d6): δ 166.5, 155.2, 144.0, 138.4, 136.4, 129.3, 128.1, 127.5, 126.9, 126.8, 126.6, 124.0, 113.4, 79.3, 74.5, 69.6, 49.8, 47.8, 34.1, 31.9, 21.9, 10.4. HRMS (AP-ESI) m/z calcd for C26H27ClN2O4S2 [M+Na]+ 553.1000, found 553.1026.

N-(5-chloro-2-propoxybenzyl)-N-(4-(N-(prop-2-yn-1-yl)sulfamoyl)phenethyl)thiazole-4-carboxamide (20)

Compound 20 was prepared from 4-thiazole carboxylic acid and 36 following the procedure of example 5 in 44% yield as a white solid. 1H-NMR (400 MHz DMSO-d6): δ 0.85-1.02 (m, 3H), 1.58-1.79 (m, 2H), 2.93-3.04 (m, 3H), 3.58-3.67 (m, 3H), 3.81-3.90 (m, 2H), 4.01 (t, J=6.32 Hz, 1H), 4.66-4.81 (m, 2H), 6.98-7.31 (m, 4H), 7.42 (d, J=7.92 Hz, 1H), 7.67 (d, J=7.92 Hz, 1H), 7.74 (d, J=7.92 Hz, 1H), 8.04-8.21 (m, 2H), 9.13-9.24 (m, 1H). $^{13}$C NMR (100 MHz, DMSO-d6): δ 163.6, 155.3, 153.9, 150.9, 144.1, 138.3, 129.2, 128.2, 127.9, 127.7, 127.6, 126.8, 124.9, 123.9, 113.3, 79.4, 74.6, 69.6, 49.7, 47.0, 34.6, 31.9, 22.0, 10.5. HRMS (AP-ESI) m/z calcd for C25H26ClN3O4S2 [M+Na]+ 554.0951, found 554.0970.

N-(5-chloro-2-propoxybenzyl)-N-(4-(N-(prop-2-yn-1-yl)sulfamoyl)phenethyl)-1,2,5-thiadiazole-3-carboxamide (21)

Compound 21 was prepared from 3-1,2,5-thiadiazole carboxylic acid and 36 following the procedure of example 5 in 40% yield as a white solid. 1H-NMR (400 MHz DMSO-d6): δ 0.80-1.01 (m, 3H), 1.52-1.78 (m, 2H), 2.92-3.05 (m, 3H), 3.64-3.69 (m, 3H), 3.82-3.88 (m, 2H), 3.98-4.00 (m, 1H), 4.72-4.74 (m, 2H), 6.98-7.08 (m, 1H), 7.22-7.34 (m, 3H), 7.43 (d, J=8.24 Hz, 1H), 7.66 (d, J=8.32 Hz, 1H), 7.74 (d, J=8.20 Hz, 1H), 8.06-8.09 (m, 1H)), 8.82-9.10 (m, 1H). $^{13}$C NMR (100 MHz, DMSO-d6): δ 161.6, 157.0, 155.4, 152.5, 143.8, 138.5, 129.3, 128.6, 128.2, 126.9, 126.7, 123.9, 113.5, 79.4, 74.5, 69.7, 49.3, 47.1, 34.2, 31.9, 21.9, 10.5. HRMS (AP-ESI) m/z calcd for C24H25ClN4O4S2 [M+Na]+ 555.0904, found 555.0917.

N-(5-chloro-2-propoxybenzyl)-N-(4-(N-(prop-2-yn-1-yl)sulfamoyl)phenethyl)-1H-1,2,4-triazole-3-carboxamide (22)

Compound 22 was prepared from 3-1,2,4-triazole carboxylic acid and 36 following the procedure of example 5 in 36% yield as a white solid. 1H-NMR (400 MHz DMSO-d6): δ 0.85-1.01 (m, 3H), 1.58-1.77 (m, 2H), 2.89-3.04 (m, 3H), 3.58-3.67 (m, 3H), 3.89 (t, J=6.40 Hz, 1H), 3.97-4.17 (m, 2H), 4.65 (s, 2H), 6.98-7.06 (m, 1H), 7.21-7.41 (m, 4H), 7.69 (d, J=7.92 Hz, 1H), 7.74 (d, J=8.28 Hz, 1H), 8.03-8.08 (m, 1H), 8.65-8.72 (m, 1H), 14.42-14.89 (m, 1H). $^{13}$C NMR (100 MHz, DMSO-d6): δ 162.3, 155.3, 152.7, 143.8, 143.4, 138.4, 129.2, 128.2, 128.1, 127.3, 127.1, 126.8, 123.9, 113.4, 79.3, 74.5, 69.7, 49.5, 46.6, 34.6, 31.9, 21.9, 10.5. HRMS (AP-ESI) m/z calcd for C24H26ClN5O4S [M+Na]+ 538.1292, found 538.1315.

N-(5-chloro-2-propoxybenzyl)-N-(4-(N-(prop-2-yn-1-yl)sulfamoyl)phenethyl)pyrazine-2-carboxamide (23)

Compound 23 was prepared from 2-1,4-diazine carboxylic acid and 36 following the procedure of example 5 in 38% yield as a white solid. 1H-NMR (400 MHz DMSO-d6): δ 0.81-1.03 (m, 3H), 1.54-1.79 (m, 2H), 2.92-3.04 (m, 3H), 3.63-3.69 (m, 4H), 3.84-4.03 (m, 2H), 4.57-4.71 (m, 2H), 6.96-7.08 (m, 1H), 7.20-7.34 (m, 3H), 7.45 (d, J=8.24 Hz, 1H), 7.65 (d, J=8.28 Hz, 1H), 7.75 (d, J=8.24 Hz, 1H), 8.08 (t, J=5.92 Hz, 1H), 8.52-8.82 (m, 3H). $^{13}$C NMR (100 MHz, DMSO-d6): δ 166.5, 155.3, 149.4, 145.5, 144.4, 143.2, 142.8, 138.5, 129.3, 128.5, 128.1, 127.9, 127.1, 126.8, 126.7, 123.9, 113.5, 79.5, 74.6, 69.7, 49.5, 47.1, 34.1, 31.9, 22.0, 10.5. HRMS (AP-ESI) m/z calcd for C26H27ClN4O4S [M+Na]+ 549.1339, found 549.1340.

5-bromo-2-propoxybenzaldehyde (38a)

Compound 38a was synthetized from 1-Bromopropane (0.65 g, 5.5 mmol) and 5-bromo-2-hydroxy benzaldehyde (1.0 g, 5.0 mmol) following the procedure of example 3 in 93% yield. 1H-NMR (400 MHz DMSO-d6): δ 1.03 (t, J=7.40 Hz, 3H), 1.75-1.84 (m, 2H), 4.12 (t, J=6.40 Hz, 2H), 7.24 (d, J=8.92 Hz, 1H), 7.74 (d, J=2.68 Hz, 1H), 7.81 (dd, J1=2.72 Hz, J2=8.96 Hz, 1H), 10.31 (s, 1H).

4-(2-((5-bromo-2-propoxybenzyl)amino)ethyl)-N-(prop-2-yn-1-yl)benzenesulfonamide (39a)

Compound 39a was synthetized from 38a (0.48 g, 2.0 mmol) and 31 (0.51 g, 2.2 mmol) following the procedure of example 4 in 50% yield. 1H-NMR (400 MHz DMSO-d6): δ 0.97 (t, J=7.36 Hz, 3H), 1.66-1.71 (m, 2H), 2.77-2.82 (m, 4H), 3.04 (t, J=2.52 Hz, 1H), 3.66-3.68 (m, 4H), 3.91 (t, J=6.36 Hz, 2H), 6.91 (d, J=8.76 Hz, 1H), 7.35 (dd, J1=2.60 Hz, J2=8.68 Hz, 1H), 7.40-7.43 (m, 3H), 7.72 (d, J=8.32 Hz, 2H), 8.03 (s, 1H).

N-(5-bromo-2-propoxybenzyl)-N-(4-(N-(prop-2-yn-1-yl)sulfamoyl)phenethyl)-2-(thio-phen-3-yl)acetamide (24)

Compound 24 was synthetized from 39a (0.26 g, 0.55 mmol) and 3-thiopheneacetic acid (0.07 g, 0.5 mmol) following the procedure of example 5 in 47% yield. 1H-NMR (400 MHz DMSO-d6): δ 0.94-0.99 (m, 3H), 1.69-1.75 (m, 2H), 2.80 (t, J=7.72 Hz, 1H), 2.87 (t, J=7.48 Hz, 1H), 3.04 (q, J=2.60 Hz, 1H), 3.47 (t, J=7.72 Hz, 1H), 3.61 (t, J=7.48 Hz, 1H), 3.64-3.72 (m, 4H), 3.93-3.98 (m, 2H), 4.46 (d, J=7.64 Hz, 2H), 6.94-7.00 (m, 2H), 7.13 (dd, J1=2.56 Hz, J2=6.64 Hz, 1H), 7.18-7.25 (m, 1H), 7.32 (d, J=8.36 Hz, 1H), 7.36-7.50 (m, 3H), 7.69 (d, J=8.36 Hz, 1H), 7.75 (d, J=8.32 Hz, 1H), 8.05-8.11 (m, 1H). $^{13}$C NMR (100 MHz, DMSO-d6): δ 170.2, 155.7, 144.1, 138.5, 135.5, 131.3, 130.3, 129.5, 129.2, 128.6, 128.5, 127.6, 126.8, 125.9, 122.3, 113.9, 111.8, 79.3, 74.6, 69.6, 48.9, 46.6, 34.8, 34.4, 31.9, 21.9, 10.5. HRMS (AP-ESI) m/z calcd for C27H29BrN2O4S2 [M+Na]$^+$ 611.0649, found 611.0637.

5-Fluoro-2-propoxybenzaldehyde (38b)

Compound 38b was synthetized from 1-Bromopropane (0.65 g, 5.5 mmol) and 5-fluoro-2-hydroxy benzaldehyde (1.0 g, 5.0 mmol) following the procedure of example 3M 93% yield. 1H-NMR (400 MHz DMSO-d6): δ 1.03 (t, J=7.40 Hz, 3H), 1.75-1.83 (m, 2H), 4.10 (t, J=6.44 Hz, 2H), 7.29 (dd, J1=4.08 Hz, J2=9.20 Hz, 1H), 7.41 (dd, J1=3.40 Hz, J2=8.52 Hz, 1H), 7.49-7.54 (m, 1H), 10.35 (d, J=3.20 Hz, 1H).

4-(2-((5-fluoro-2-propoxybenzyl)amino)ethyl)-N-(prop-2-yn-1-yl)benzenesulfonamide (39b)

Compound 39b was synthetized from 38b (0.48 g, 2.0 mmol) and 31 (0.51 g, 2.2 mmol) following the procedure of example 4 in 43% yield. 1H-NMR (400 MHz DMSO-d6): δ 1.03 (t, J=7.32 Hz, 3H), 1.71-1.79 (m, 2H), 2.75-2.97 (m, 4H), 3.08 (t, J=2.52 Hz, 1H), 3.68-3.71 (m, 4H), 3.98 (t, J=6.48 Hz, 2H), 6.96-7.08 (m, 2H), 7.17-7.23 (m, 1H), 7.48 (d, J=8.36 Hz, 2H), 7.78 (d, J=8.32 Hz, 2H), 8.08 (s, 1H).

N-(5-fluoro-2-propoxybenzyl)-N-(4-(N-(prop-2-yn-1-yl)sulfamoyl)phenethyl)-2-(thio-phen-3-yl)acetamide (25)

Compound 25 was prepared from 3-thipheneacetic acid and 39b following the procedure of example 5 in 37% yield as a white solid. 1H-NMR (400 MHz DMSO-d6): δ 0.94-1.00 (m, 3H), 1.68-1.76 (m, 2H), 2.82 (t, J=7.08 Hz, 1H), 2.89 (t, J=7.52 Hz, 1H), 3.03 (q, J=2.60 Hz, 1H), 3.49 (t, J=6.60 Hz, 1H), 3.62 (t, J=7.28 Hz, 1H), 3.64-3.67 (m, 2H), 3.71 (d, J=3.76 Hz, 2H), 3.91-3.96 (m, 2H), 4.47 (d, J=13.52 Hz, 2H), 6.79-6.85 (m, 1H), 6.94-7.12 (m, 3H), 7.25 (dd, J1=1.72 Hz, J2=21.88 Hz, 1H), 7.33 (d, J=8.20 Hz, 1H), 7.44 (d, J=8.24 Hz, 1H), 7.46-7.49 (m, 1H), 7.69 (d, J=8.32 Hz, 1H), 7.75 (d, J=8.32 Hz, 1H), 8.04-8.10 (m, 1H). 13C NMR (100 MHz, DMSO-d6): δ 170.2, 155.0, 152.6, 144.2, 138.5, 135.6, 129.5, 129.2, 128.8, 128.5, 127.8, 126.8, 125.8, 122.4, 114.6, 113.9, 112.9, 79.3, 74.6, 69.8, 48.9, 46.7, 34.8, 34.2, 31.9, 22.1, 10.5. HRMS (AP-ESI) m/z calcd for C27H29FN2O4S2 [M+Na]$^+$ 551.1450, found 551.1433.

2-butoxy-5-chlorobenzaldehyde (40a)

Compound 40a was synthetized from bromobutane (0.6 g, 4.4 mmol) and 5-chloro-2-hydroxy benzaldehyde (0.6 g, 4 mmol) following the procedure of example 3 in 88% yield. 1H-NMR (400 MHz DMSO-d6): δ 0.97 (t, J=7.36 Hz, 3H), 1.43-1.52 (m, 2H), 1.73-1.79 (m, 2H), 4.17 (t, J=6.40 Hz, 2H), 7.30 (d, J=8.92 Hz, 1H), 7.62 (d, J=2.80 Hz, 1H), 7.69 (dd, J1=2.80 Hz, J2=8.92 Hz, 1H), 10.31 (s, 1H).

4-(2-((2-butoxy-5-chlorobenzyl)amino)ethyl)-N-(prop-2-yn-1-yl)benzenesulfonamide (41a)

Compound 41a was synthetized from 40a (0.42 g, 2 mmol) and 31 (0.51 g, 2.2 mmol) following the procedure of example 4 in 43% yield. 1H-NMR (400 MHz DMSO-d6): δ 0.94 (t, J=7.36 Hz, 3H), 1.37-1.46 (m, 2H), 1.63-1.69 (m, 2H), 2.76-2.82 (m, 4H), 3.04 (t, J=2.52 Hz, 1H), 3.66-3.69 (m, 4H), 3.96 (t, J=6.36 Hz, 2H), 6.97 (d, J=8.72 Hz, 1H), 7.23 (dd, J1=2.76 Hz, J2=8.68 Hz, 1H), 7.31 (d, J=2.72 Hz, 1H), 7.43 (d, J=6.36 Hz, 2H), 7.72 (d, J=8.36 Hz, 2H), 8.05 (s, 1H).

N-(2-butoxy-5-chlorobenzyl)-N-(4-(N-(prop-2-yn-1-yl)sulfamoyl)phenethyl)-2-(thio-phen-3-yl)acetamide (26)

Compound 26 was synthetized from 41a (0.26 g, 0.55 mmol) and 3-thiopheneacetic acid (0.07 g, 0.5 mmol) following the procedure of example 5 in 49% yield as a white solid. 1H-NMR (400 MHz DMSO-d6): δ 0.89-0.94 (m, 3H), 1.38-1.48 (m, 2H), 1.65-1.72 (m, 2H), 2.81 (t, J=7.56 Hz, 1H), 2.88 (t, J=7.56 Hz, 1H), 3.04 (q, J=2.52 Hz, 1H), 3.47 (t, J=7.44 Hz, 1H), 3.61 (t, J=7.48 Hz, 1H), 3.64-3.66 (m, 2H), 3.71 (d, J=7.22 Hz, 2H), 3.97-4.02 (m, 2H), 4.45 (d, J=6.84 Hz, 2H), 6.93-7.06 (m, 3H), 7.18-7.33 (m, 3H), 7.44 (d, J=8.36 Hz, 1H), 7.47-7.49 (m, 1H), 7.69 (d, J=8.36 Hz, 1H), 7.75 (d, J=8.32 Hz, 1H), 8.04-8.10 (m, 1H). $^{13}$C NMR (100 MHz, DMSO-d6): δ 170.2, 155.2, 144.1, 138.5, 135.5, 129.5, 129.2, 128.6, 128.5, 127.9, 127.6, 127.4, 126.8, 125.9, 124.1, 122.3, 113.4, 79.3, 74.6, 67.8, 48.9, 46.6, 34.8, 34.3, 31.9, 30.7, 18.7, 13.7. HRMS (AP-ESI) m/z calcd for C28H31ClN2O4S2 [M+Na]$^+$ 581.1311, found 581.1314.

5-chloro-2-(pentyloxy)benzaldehyde (40b)

Compound 40b was synthetized from 1-Bromopentane (0.83 g, 5.5 mmol) and 5-chloro-2-hydroxy benzaldehyde (0.78 g, 5.0 mmol) following the procedure of example 3 in 89% yield. 1H-NMR (400 MHz DMSO-d6): δ 0.92 (t, J=7.16 Hz, 3H), 1.31-1.47 (m, 4H), 1.75-1.82 (m, 2H), 4.16

(t, J=6.44 Hz, 2H), 7.29 (d, J=8.92 Hz, 1H), 7.62 (d, J=2.80 Hz, 1H), 7.69 (dd, J1=2.84 Hz, J2=8.92 Hz, 1H), 10.32 (s, 1H).

4-(2-((5-chloro-2-(pentyloxy)benzyl)amino)ethyl)-N-(prop-2-yn-1-yl)benzenesulfonamide (41b)

Compound 41b was synthetized from 40b (0.45 g, 2.0 mmol) and 31 (0.51 g, 2.2 mmol) following the procedure of example 4 in 51% yield. 1H-NMR (400 MHz DMSO-d6): δ 0.90 (t, J=7.32 Hz, 3H), 1.28-1.41 (m, 4H), 1.65-1.73 (m, 2H), 2.69-2.99 (m, 4H), 3.01-3.04 (m, 1H), 3.57-3.67 (m, 4H), 3.92-3.99 (m, 2H), 6.95 (d, J=6.52 Hz, 1H), 7.20 (dd, J1=2.76 Hz, J2=6.68 Hz, 1H), 7.32-7.35 (m, 1H), 7.46 (d, J=6.32 Hz, 2H), 7.76 (d, J=8.24 Hz, 2H), 8.08 (s, 1H).

2-(sec-butoxy)-5-chlorobenzaldehyde (40c)

Compound 40c was synthetized from 2-Bromobutane (0.75 g, 5.5 mmol) and 5-chloro-2-hydroxy benzaldehyde (0.78 g, 5.0 mmol) following the procedure of example 3M 82% yield. 1H-NMR (400 MHz DMSO-d6): δ 0.97 (t, J=7.44 Hz, 3H), 1.30 (d, J=6.08 Hz, 3H), 1.58-1.79 (m, 2H), 4.58-4.65 (m, 1H), 7.33 (d, J=8.96 Hz, 1H), 7.61 (d, J=2.84 Hz, 1H), 7.68 (dd, J1=2.88 Hz, J2=8.92 Hz, 1H), 10.31 (s, 1H).

4-(2-((2-(sec-butoxy)-5-chlorobenzyl)amino)ethyl)-N-(prop-2-yn-1-yl)benzenesulfonamide (41c)

Compound 41c was synthetized from 40c (0.42 g, 2.0 mmol) and 31 (0.51 g, 2.2 mmol) following the procedure of example 4 in 46% yield. 1H-NMR (400 MHz DMSO-d6): δ 0.97 (t, J=7.48 Hz, 3H), 1.27 (t, J=6.04 Hz, 3H), 1.58-1.72 (m, 2H), 2.74-2.98 (m, 4H), 3.07-3.09 (m, 1H), 3.62-3.72 (m, 4H), 4.40-4.47 (m, 1H), 7.03 (d, J=8.56 Hz, 1H), 7.25 (dd, J1=2.84 Hz, J2=8.56 Hz, 1H), 7.32-7.33 (m, 1H), 7.41 (d, J=6.56 Hz, 2H), 7.79 (d, J=8.32 Hz, 2H), 8.09 (s, 1H).

N-(5-chloro-2-(pentyloxy)benzyl)-N-(4-(N-(prop-2-yn-1-yl)sulfamoyl)phenethyl)-2-(thiophen-3-yl)acetamide (27)

Compound 27 was synthetized from 41b and 3-thiopheneacetic acid following the procedure of example 5 in 45% yield as a white solid. 1H-NMR (400 MHz DMSO-d6): δ 0.86-0.90 (m, 3H), 1.32-1.40 (m, 4H), 1.68-1.75 (m, 2H), 2.80 (t, J=7.68 Hz, 1H), 2.88 (t, J=7.56 Hz, 1H), 3.01-3.03 (m, 1H), 3.48 (t, J=7.52 Hz, 1H), 3.61 (t, J=7.56 Hz, 1H), 3.64-3.71 (m, 4H), 3.97-4.02 (m, 2H), 4.45-4.46 (m, 2H), 6.93-7.06 (m, 3H), 7.23-7.34 (m, 3H), 7.44 (d, J=8.32 Hz, 1H), 7.47-7.50 (m, 1H), 7.69 (d, J=8.28 Hz, 1H), 7.75 (d, J=8.32 Hz, 1H), 8.04-8.10 (m, 1H). 13C NMR (100 MHz, DMSO-d6): δ 170.2, 155.1, 144.1, 138.5, 135.5, 129.5, 129.2, 128.6, 128.4, 127.9, 127.6, 127.5, 126.8, 125.9, 124.0, 122.3, 113.4, 79.3, 74.6, 68.1, 48.9, 46.5, 34.8, 34.3, 31.9, 28.3, 27.7, 21.8, 13.9. HRMS (AP-ESI) m/z calcd for C29H33ClN2O4S2 [M+Na]+ 595.1468, found 595.1462.

N-(2-(sec-butoxy)-5-chlorobenzyl)-N-(4-(N-(prop-2-yn-1-yl)sulfamoyl)phenethyl)-2-(thiophen-3-yl)acetamide (28)

Compound 28 was synthetized from 41c and 3-thiopheneacetic acid following the procedure of example 5 in 52% yield as a white solid. 1H-NMR (400 MHz DMSO-d6): δ 0.88-0.93 (m, 3H), 1.20-1.22 (m, 3H), 1.54-1.67 (m, 2H), 2.80 (t, J=7.56 Hz, 1H), 2.89 (t, J=7.40 Hz, 1H), 3.01-3.03 (m, 1H), 3.46 (t, J=7.36 Hz, 1H), 3.60 (t, J=7.44 Hz, 1H), 3.64-3.72 (m, 4H), 4.40-4.42 (m, 2H), 6.93-7.08 (m, 3H), 7.18-7.32 (m, 3H), 7.44 (d, J=8.36 Hz, 1H), 7.47-7.49 (m, 1H), 7.69 (d, J=8.32 Hz, 1H), 7.75 (d, J=8.28 Hz, 1H), 8.04-8.10 (m, 1H). 13C NMR (100 MHz, DMSO-d6): δ 170.2, 154.3, 144.1, 138.5, 135.5, 129.5, 129.2, 128.7, 128.5, 127.9, 127.8, 127.6, 126.8, 125.9, 123.8, 122.3, 114.6, 79.3, 74.9, 74.6, 48.8, 46.7, 34.9, 34.3, 31.9, 28.5, 18.9, 9.5. HRMS (AP-ESI) m/z calcd for C28H31ClN2O4S2 [M+Na]+ 581.1311, found 581.1308.

Example 7. IL-1β Assays in J774A.1 Cells

J774A.1 cells were plated into a 96-well plate (1×105 cells/well) for 24 h in growth medium. Cells were primed with *Escherichia coli* 0111:B4 LPS (Sigma-Aldrich) (final concentration: 1 µg/mL) for 4.5 h. Next, test compounds were added for 30 min. ATP (5 mM) was added at the same time when compounds were added to induce NLRP3 inflammasome activation. After 30 min, the supernatants were collected and the level of IL-1β was measured with a mouse IL-1β ELISA kit following the manufacturer's instructions. Primary peritoneal macrophages were similarly treated as described with J774A.1 cell line followed by ELISA analysis for IL-β production.

Example 8. IL-1β Assays in Mouse Peritoneal Macrophages

C57BL/6 mice were injected with 1 mL of 3% thioglycolate into the peritoneal cavity. Peritoneal cells were collected 3 days after injection by flushing the peritoneal cavity with cold PBS. The peritoneal cells were plated in complete RPMI1640 media containing 10% FBS, 100 U/mL penicillin, 100 µg/mL streptomycin. Floating cells were removed after 2 h and adherent peritoneal macrophages were used for experiments as described above.

Example 9. Inhibition of NLRC4 and AIM2 Inflammasomes Assays

J774A.1 cells were plated into a 96-well plate. (1×105 cells/well) for 24 h in growth medium. Cells were treated with LPS (1 µg/mL) and test compounds for 1 h. Flagellin or poly-deoxyadenylic-deoxythymidylic acid sodium salt (Poly(dA:dT)) was used to induce the formation of the NLRC4 and the AIM2 inflammasomes. Flagellin (Enzo Life Sciences, Farmingdale, NY), isolated from *Salmonella typhimurium* strain 14028, was added in DMEM (Invitrogen) without fetal bovine serum (FBS) to the plate (1 µg/mL and allowed to incubate for 6 h. Flagellin cell-transfection was accomplished utilizing the Polyplus transfection kit (PULSin, New York, NY). For AIM2 activation, cells were incubated with Poly(dA:dT) (4 µg/ml) (InvivoGen, San Diego, CA) for 8 h. The supernatants were collected and levels of IL-1β were measured with a mouse IL-1β ELISA kit following the manufacturer's instructions.

Example 10. In Vitro BBB Assay hCMEC/D3 cells were used from passage 25 to 35. The in vitro model of BBB was built by seeding 150,000 cells/well on the apical surface of 12-well transwell plate with 3.0 micron pores. See Pate et al. (*Antimicrob. Agents Chemother.* 2017; 61: E01307-01317) for protocol. The cells were supplemented with growth medium for the initial 48 h period and then with maintenance medium for the next 72 h. Medium was replenished every day until the transport experiments were performed. The apical side of the transwell represents the blood side, while basolateral side represents the brain side. On the fifth day, vectorial transport (A-to-B, B-to-A) of 17 (20 μM, dissolved in DPBS with 0.01% DMSO) was determined by adding compound in one compartment and sampling the appearance of compound in the opposing compartment. Samples were collected at 5, 10, 15, 30, 45, and 60 min Compound 17 was quantified by HPLC. Apparent permeability (Papp) was then calculated.

Example 11. LPS Challenge In Vivo and Compound Treatment

C57BL/6 mice were injected intraperitoneally (i.p.) with 50 mg/kg LPS (Sigma-Aldrich) or PBS one hour after compound (10 mg/kg) or vehicle treatment. For nlrp3−/− mice, 25 mg/kg of LPS was injected by i.p. Serum levels of IL-1β and TNF-α were measured by ELISA 2.5 h after LPS injection.

Example 12. In Vivo BBB Penetration and PK Studies

C57BL/6 mice (n=3 for each time point) were given compound 17 by PO administration (20 mg/kg) or vehicle treatment. Plasma samples (200-500 μL) and brain tissues (after saline perfusion) were collected at 0.5, 1, and 4 h time points and stored in −80° C. freezer for later analysis. Sprague-Dawley rats (200-250 g, n=3) were given compound 17 by IV and PO administration (20 mg/kg). Plasma samples (~500 μL) were collected at 0.08, 0.17, 0.25, 0.5, 0.75, 1.0, 2.0, 4.0, 8.0, 12.0, and 24.0 h time points through orbital vein and were stored in −80° C. freezer for later analysis.

Example 13. LC-MS/MS Analysis

Plasma samples were thawed and centrifuged at 3000 rpm (2095 g). 40 μL of each sample was added to a 1.5 mL microcentrifuge tube and 25 μL of internal standard (100 ng/mL glipizide) was added. Samples were mixed by vortexing for 30 seconds. In order to precipitate the proteins, 250 μL of 1% ammonium formate in methanol was added to each sample and mixed by vortex for 2 minutes. Samples were centrifuged at 14000 rpm (10,956 g) for 5 minutes, and the supernatant was transferred to a 1.5 mL microcentrifuge tube with a microfilter tube (0.45 μm) filter insert (Pall Corporation, New York, USA). The remaining supernatant was evaporated under a nitrogen stream at 55° C. The dry residue was reconstituted with 90:10 methanol:water. Samples were transferred to 96-well plate for analysis by LC-MS/MS. For tissue samples, brain samples were thawed and centrifuged at 3000 rpm (2095 g). To each tissue sample, 100 μL of PBS, 25 μL of internal standard (100 ng/mL glipizide), and 250 μL of 1% ammonium formate in methanol was added. The tissue was homogenized at a gradually increasing speed for 30 seconds using a beadbug mixer (Benchmark Scientific, Atkinson, NH, USA) with 6 cycles, then centrifuged at 14000 rpm (10,956 g) for 5 min. The supernatant was transferred to 1.5 mL microtube with a microfilter tube (0.45 μm) filter insert (Pall Corporation, New York, USA). The remaining supernatant was evaporated under a nitrogen stream at 55° C. The dry residue was reconstituted with 90:10 methanol:water. Samples were transferred to 96-well plate for analysis by LC-MS/MS. Chromatographic separation was achieved using a Waters Acquity HPLC with a Phenomenex Gemini 2.1×30 mm 5-micron column (Phenomenex, Torrance, CA, USA) and a gradient mobile phase (1% formic acid, Mobile Phase A, and acetonitrile, Mobile Phase B). Flow was a constant 0.40 μL/min, with 95% A from 0 to 1.0 minutes. From 1.0 to 3.25 minutes, the composition changed to 95% mobile phase B, and held until 4.25 min. From 4.5 minutes to 5.0 min initial conditions were re-established with 95% 1% formic acid in water. The LC-MS/MS method employed was positive electrospray ionization and the following MRM transitions used were as follows: Compound 17 546.400>155.1 and glipizide 446.2>321.200. Results were processed using Analyst 1.5.2, on an AB Sciex 4000 QTrap hybrid linear ion trap tandem mass spectrometer. The linear range for the method was 1-5000 ng/mL, with a linear, 1/x regression method.

Example 14. Design of a New Chemical Scaffold as NLRP3 Inhibitors

Previous SAR studies of a small molecule compound identified as JC124 suggested that only limited modifications can be tolerated on the phenyl ring of the benzamide moiety. (See: Fulp et al. Structural Insights of Benzenesulfonamide Analogues as Nlrp3 Inflammasome Inhibitors: Design, Synthesis, and Biological Characterization. *J. Med. Chem.* 2018, 61, 5412-5423, incorporated herein by reference).

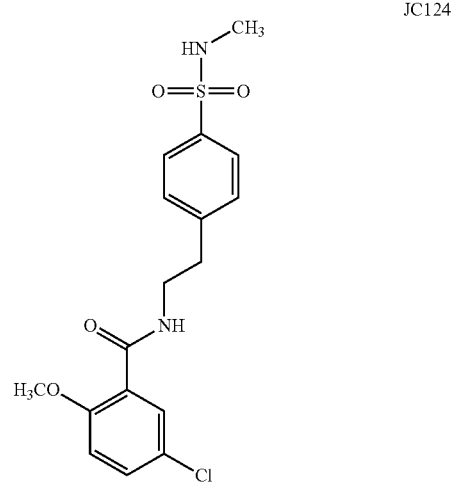

JC124

HL16

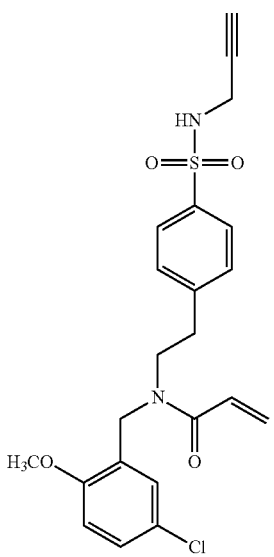

To expand the scope for structural variations and optimization of this lead structure, we designed a new chemical scaffold identified herein as Formula I. Two of the small molecule compound products of the Formula I base scaffold are HL16/Formula III and Formula IV. In the chemical structure HL16/Formula III, we changed the amide functional group to an appendix position of the chemical structure and this allows introduction of a variety of substituents to explore the SAR and to optimize the biological activity. Specifically, we incorporated a propargyl substituent on the sulfonamide moiety and an acrylamide moiety based on the results of our chemical probe studies.

Figure 1B:
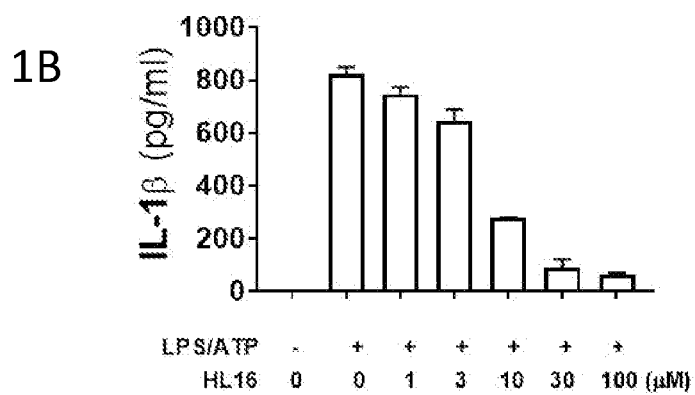
Figure 1C:
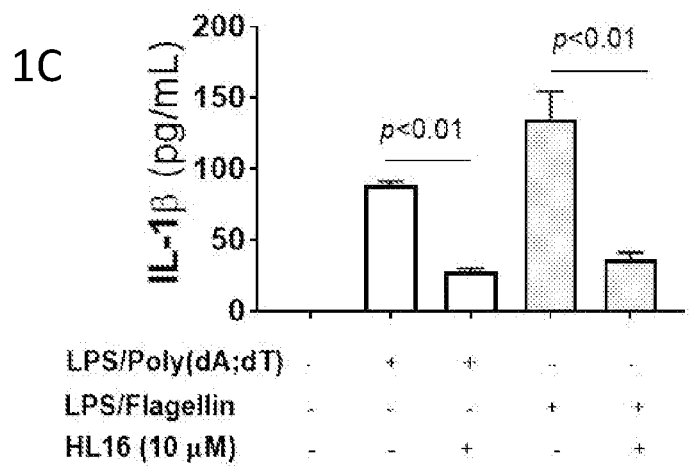

In vitro studies were conducted to compare the effects of JC124 and HL16/Formula III. Biological characterization from murine macrophage J774A.1 cells that release IL-1β upon the activation of NLRP3 inflammasome by lipopolysaccharide (LPS) and adenosine triphosphate (ATP) established an IC50 of 1.30±0.23 μM for HL16/Formula III (FIG. 1A), 2.5-fold increase compared that of JC124. See Marchetti et al. (*J Cardiovasc Pharmacol.* 2014, 63:316-322). The inhibitory activity of HL16/Formula III was also confirmed in mouse peritoneal macrophages (FIG. 1B). However, when the selectivity was examined (J774A.1 cells were stimulated with LPS/poly(dA:dT) or LPS/flagellin to activate the NLRC4 and AIM2 inflammasome, (respectively) (FIG. 1C). HL16/Formula III also significantly inhibited NLRC4 and AIM2 inflammasomes at 10 μM concentration. Further testing in mice challenged with LPS also demonstrated that treatment with HL16/Formula III (10 mg/kg) let to significant suppression of both IL-1β and TNF-α, while MCC950 (10 mg/kg), a known NLRP3 inhibitor used as a positive control, only inhibited IL-1β, suggesting that the action of HL16/Formula III is nonspecific.

Example 15. Structural Exploration of HL16/Formula III by SAR Studies

Figure 2:
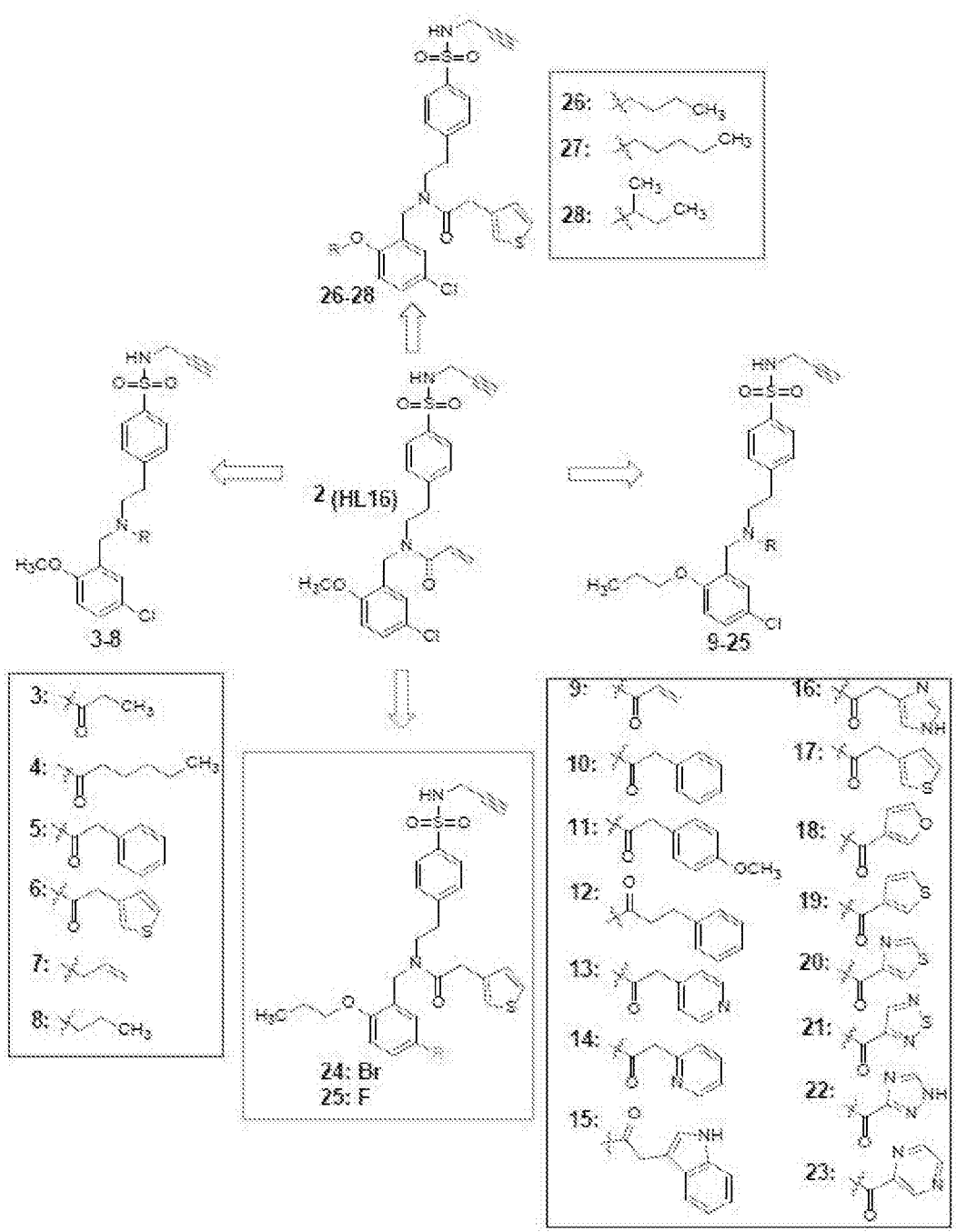
FIG. 2 illustrates the design and synthesis of chemical structures of analogues of HL16, which are small molecule inhibitors targeting the NLRP3 inflammasome pathway.

To explore whether structural modifications of HL16/Formula III will improve inhibitory potency and selectivity to NLRP3 inflammasome, a series of analogs were designed and synthesized. As shown in FIG. 2, structural modifications were mainly focused on two positions of HL16/Formula III: the appendix amide and the methoxy group on the benzyl moiety. To evaluate the role of the chlorine substitution, we also designed analogs with a fluorine or bromine at this position. In total, twenty-six analogs were designed and synthesized.

The chemical syntheses were achieved by the conditions outlined in Schemes 1 and 2. Briefly, reaction of sulfonyl chloride 29 with propargylamine gave 30, followed by de-protection using methylhydrazine in benzene to provide the amine 31. Aldehyde 32 was reacted with iodomethane or 1-bromopropane to obtain compound 33 or 35, respectively. Reductive amination of 33 with 31 in the presence of NaBH3CN yielded 34, which on coupling reaction with various carboxylic acids in the presence of 1-(3-Dimethylaminopropyl)-3-ethylcarbodiimide hydrochloride (EDCI) and 1-hydroxybenzotriazole (HOBt) gave the target compounds 2-6. Alkylation of 34 with allyl bromide or 1-bromopropane afforded 7 and 8, respectively. Similarly, compound 9-25 were synthetized following the conditions outlined in schemes 1 and 2 with 35, 37 or 40 as the starting material.

Scheme 1

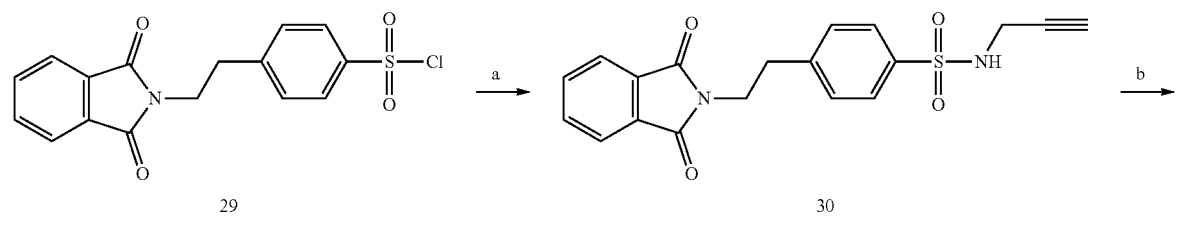

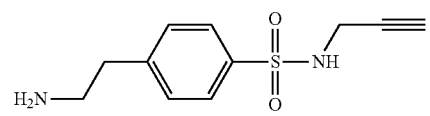

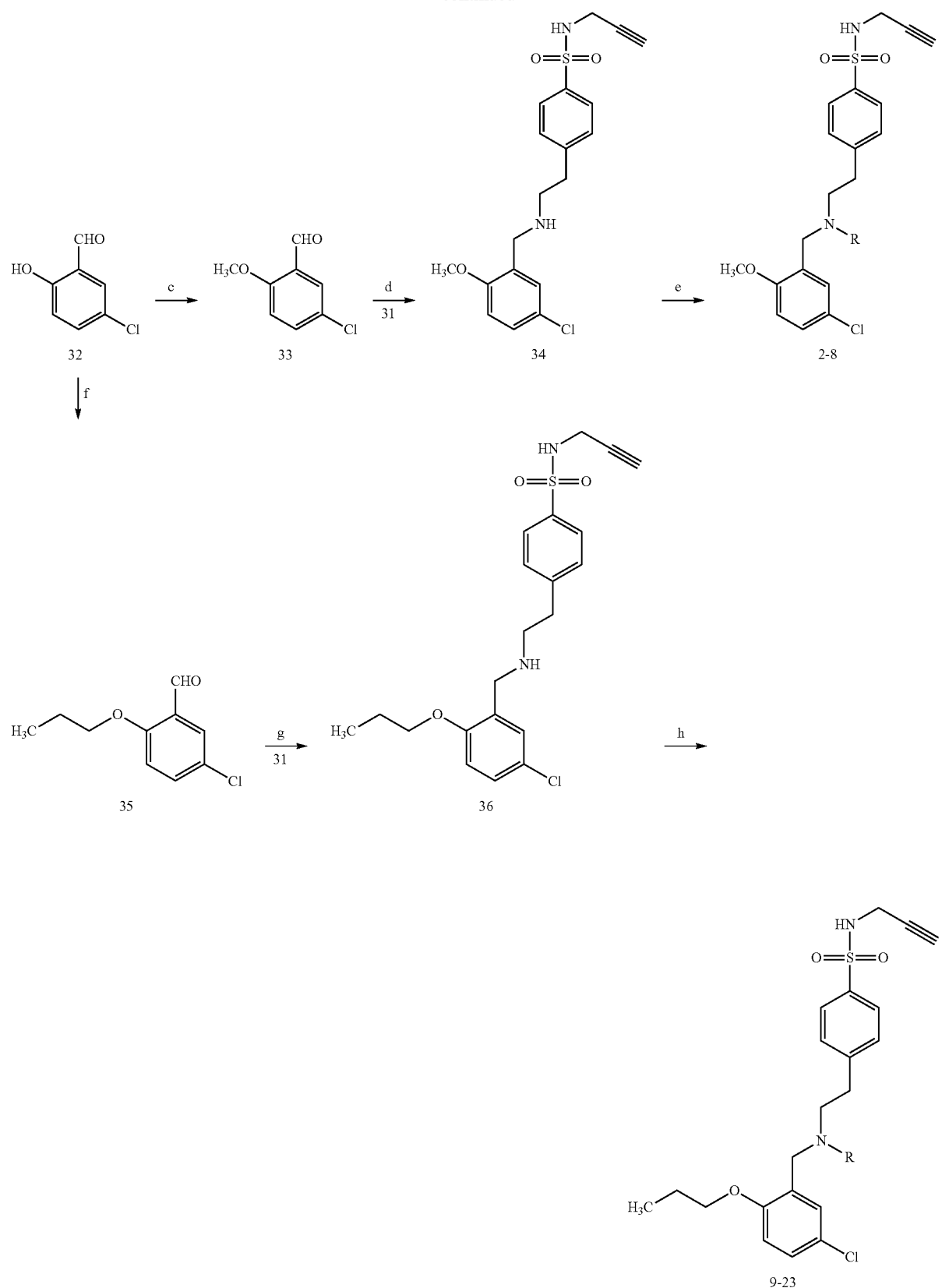

-continued
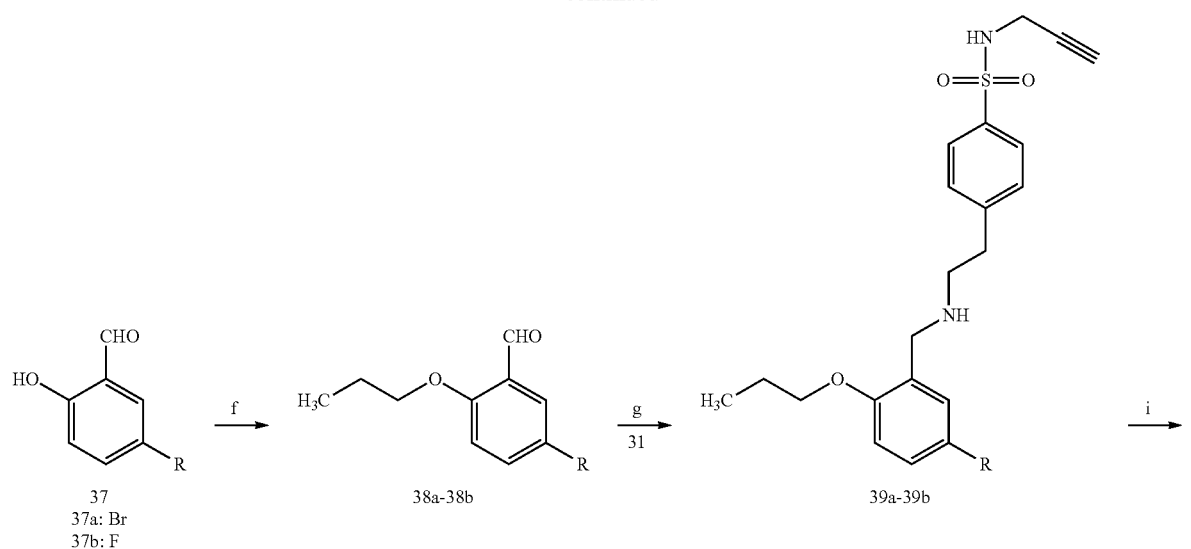
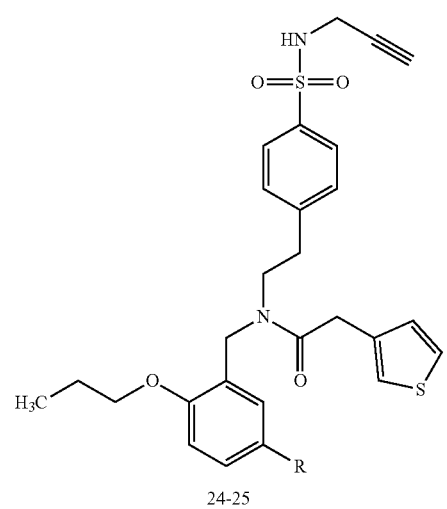
Reagents and conditions: (a) Propargylamine, TEA, DCM; (b) Methylhydrazine, benzene; (c) Iodomethane, K2CO3, DMF; (d) TEA, Acetic acid, NaCNBH3; (e) various acids, EDCI, HOBt, TEA, DCM; For 7 and 8: K2CO3, DMF; (f) 1-Bromopropane, K2CO3, DMF; (g) TEA, Acetic acid, NaCNBH3; (h) various acids, EDCI, HOBt, TEA, DCM. (i) 3-Thiopheneacetic acid, EDCI, HOBt, TEA, DCM.

Scheme 2

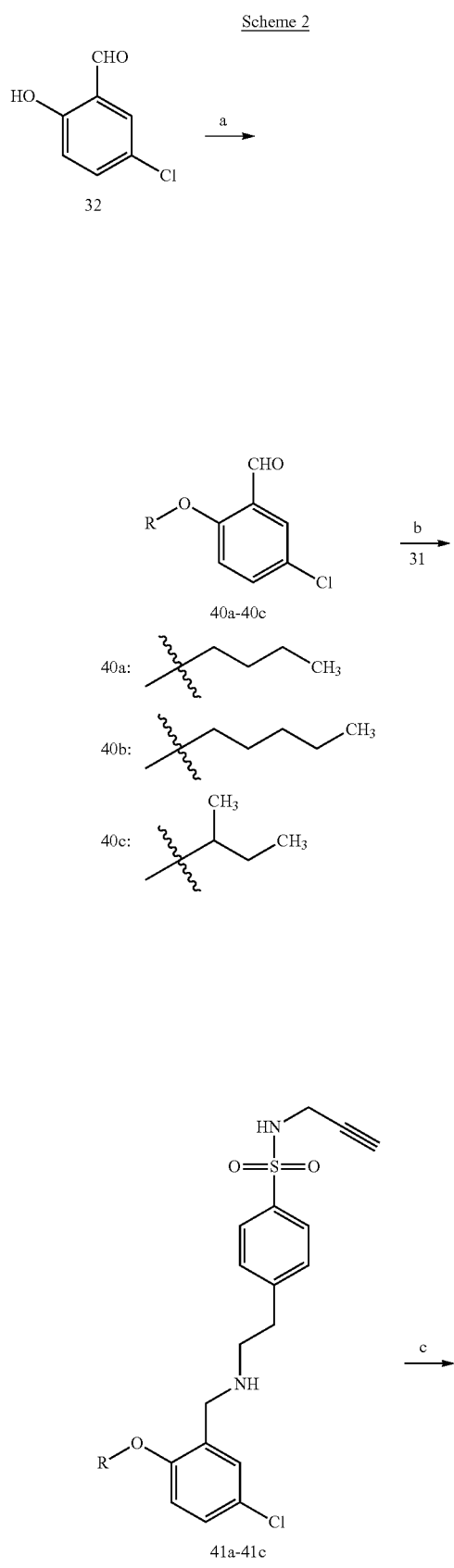

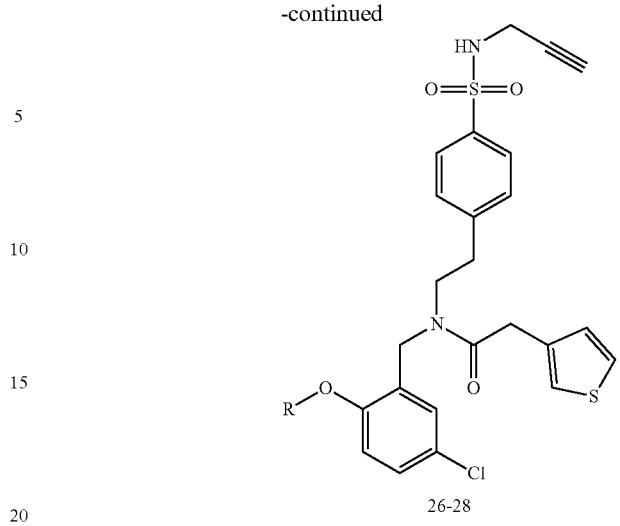

Reagents and conditions: (a) K2CO3, DMF (b) TEA, Acetic acid, NaCNBH3; (c) 3-Thiopheneacetic acid, EDCI, HOBt, TEA, DCM.

After synthesis, the analogs were tested using the J774A.1 cell model upon challenge with LPS/ATP to measure their inhibitory potencies on the release of IL-1β by an enzyme-linked immunosorbent assay (ELISA). As shown in Table 1, saturation of the acrylamide to a propenamide, as represented by compound 3, retained the inhibitory potency. This suggests that a covalent interaction with the acrylamide is not a contributing factor to the observed inhibitory activity of HL16. Chain extension to a hexanamide as in 4 did not lead to improved inhibitory potency. Notably, replacement with a 2-phenylacetamide lead to ~2-fold increase of inhibitory potency as evidenced by compound 5. Bioisoteric replacement of the phenyl ring of 5 with a thiophene (6) retained its inhibitory potency. To evaluate whether the appendix amide is essential to the biological activity, compounds 7 and 8 were designed and tested. The results of these two analogs suggest that a tertiary amine can still maintain the inhibitory potency. Replacement of the methoxy substituent in the structure of HL16/Formula III with a propoxyl one as illustrated by compound 9 led to improvement of inhibitory potency. Therefore, in the following analogs, we kept this propoxyl substituent and varied the appendix amide to evaluate their effects on the inhibitory potency. Surprisingly, the combination of a 2-phenylacetamide and a propoxyl substituent in compound 10 did not result in increased inhibitory potency compared to compound 5 or compound 9. Introduction of a para-methoxy on the phenyl ring of compound 10 led to reduction of inhibitory potency as seen by compound 11. However, structural extension to a 3-phenylpropanamide in compound 12 retained the inhibitory potency. Bioisosteric replacement of the phenyl ring of the 2-phenylacetamide with a 2- (compound 13) or 3-pyridine (compound 14), or 3-indole (compound 15) retained the inhibitory potency while replacement with an imidazole-4-yl moiety (compound 16) led to a ~2-fold reduction of inhibitory potency. Notably, replacement of the phenyl ring of the 2-phenylacetamide with a 3-thiophene (compound 17) further increased the inhibitory potency by 2-fold. Change of the 2-phenylacetamide of compound 10 to a furan-3-carboxamide (compound 18), thiophene-3-carboxamide (compound 19), 1,3-thiazole-4-carboxamide (compound 20), or (2,5-diaza-1-thiazole)-3-carboxamide (compound 21) all slightly increased the inhibitory potency while replacement with (1,2,4-traizole)-3-carboxamide (compound 22) and pyrazine-2-carboxamide (compound 23) led to slight reduction of inhibitory potency. Based on these observations, we further replaced the Cl of compound 17 with a Br (compound 24) or F (compound 25) and this led to reduction of inhibitory potency. We also evaluated how the propoxyl substituent of compound 17 can be further modified in compound analogs 26-28. The results demonstrated that increase of chain length or steric hindrance did not improve the inhibitory potency.

TABLE 1

Inhibitory potency of analogs on the production of IL-1β by J774A.1 cells upon stimulation with LPS/ATP. (Unless otherwise indicated, + is an $IC_{50}$ > 30 μM; ++ is an $IC_{50}$ 10-30 μM; +++ is an $IC_{50}$ 1-10 μM; and ++++ is an $IC_{50}$ < 1 μM)

| Compound Number and $IC_{50}$ | Chemical Structure |
| --- | --- |
| SZ-N3I-12<br>++++ | |
| SZ-N3I-13<br>Compound 5<br>++++ | |

TABLE 1-continued
Inhibitory potency of analogs on the production of IL-1β by J774A.1 cells upon stimulation with LPS/ATP. (Unless otherwise indicated, + is an $IC_{50} > 30$ μM; ++ is an $IC_{50}$ 10-30 μM; +++ is an $IC_{50}$ 1-10 μM; and ++++ is an $IC_{50} < 1$ μM)
| Compound Number and $IC_{50}$ | Chemical Structure |
| --- | --- |
| SZ-N3I-14<br>+++ | 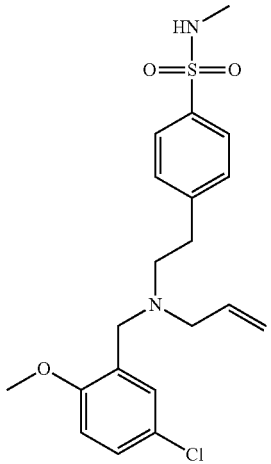 [SMILES: C=CCN(CCc1ccc(S(=O)(=O)NC)cc1)Cc1cc(Cl)ccc1OC] |
| SZ-N3I-15<br>Compound 7<br>+++ | 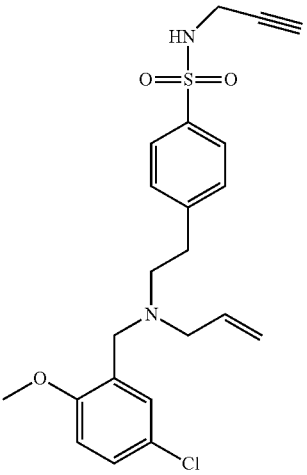 [SMILES: C#CCNS(=O)(=O)c1ccc(CCN(CC=C)Cc2cc(Cl)ccc2OC)cc1] |
| SZ-N3I-16<br>+++ | 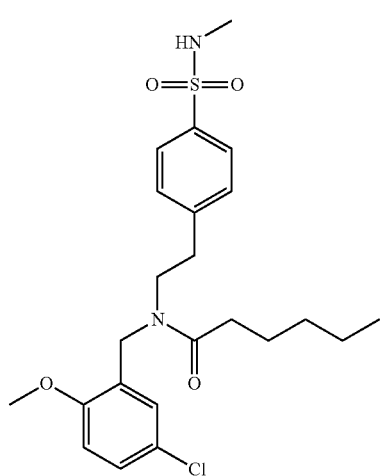 [SMILES: CCCCCC(=O)N(CCc1ccc(S(=O)(=O)NC)cc1)Cc1cc(Cl)ccc1OC] |

TABLE 1-continued

Inhibitory potency of analogs on the production of IL-1β by J774A.1 cells upon stimulation with LPS/ATP. (Unless otherwise indicated, + is an IC$_{50}$ > 30 μM; ++ is an IC$_{50}$ 10-30 μM; +++ is an IC$_{50}$ 1-10 μM; and ++++ is an IC$_{50}$ < 1 μM)

| Compound Number and IC$_{50}$ | Chemical Structure |
|---|---|
| SZ-N3I-17 Compound 4 +++ | 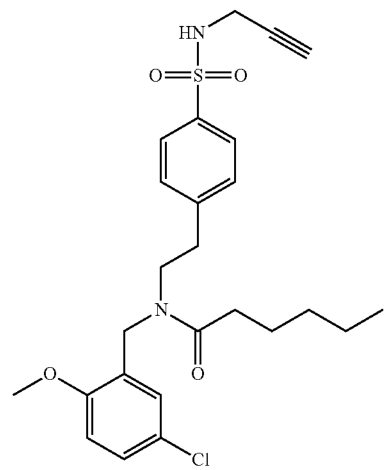 [SMILES: C#CCNS(=O)(=O)c1ccc(CCN(Cc2cc(Cl)ccc2OC)C(=O)CCCCC)cc1] |
| SZ-N3I-18 +++ | 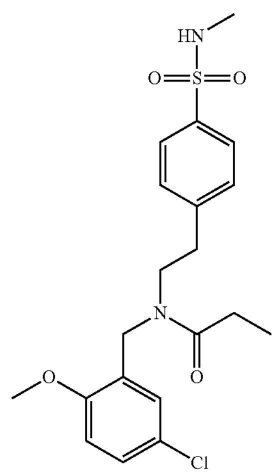 [SMILES: CCC(=O)N(CCc1ccc(S(=O)(=O)NC)cc1)Cc1cc(Cl)ccc1OC] |
| SZ-N3I-19 Compound 3 +++ | 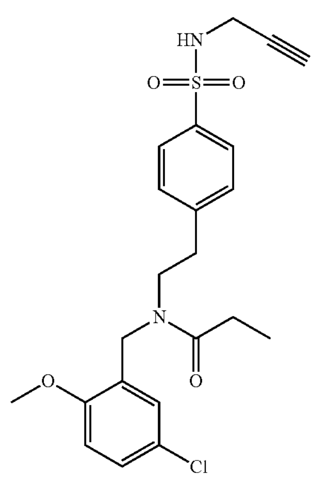 [SMILES: C#CCNS(=O)(=O)c1ccc(CCN(Cc2cc(Cl)ccc2OC)C(=O)CC)cc1] |

TABLE 1-continued

Inhibitory potency of analogs on the production of IL-1β by J774A.1 cells upon stimulation with LPS/ATP. (Unless otherwise indicated, + is an $IC_{50} > 30$ μM; ++ is an $IC_{50}$ 10-30 μM; +++ is an $IC_{50}$ 1-10 μM; and ++++ is an $IC_{50} < 1$ μM)

| Compound Number and $IC_{50}$ | Chemical Structure |
| --- | --- |
| SZ-N3I-20<br>+++ | |
| SZ-N3I-21<br>Compound 8<br>+++ | |

TABLE 1-continued
Inhibitory potency of analogs on the production of IL-1β by J774A.1 cells upon stimulation with LPS/ATP. (Unless otherwise indicated, + is an $IC_{50}$ > 30 μM; ++ is an $IC_{50}$ 10-30 μM; +++ is an $IC_{50}$ 1-10 μM; and ++++ is an $IC_{50}$ < 1 μM)
| Compound Number and $IC_{50}$ | Chemical Structure |
| --- | --- |
| SZ-N3I-22<br>++++ | 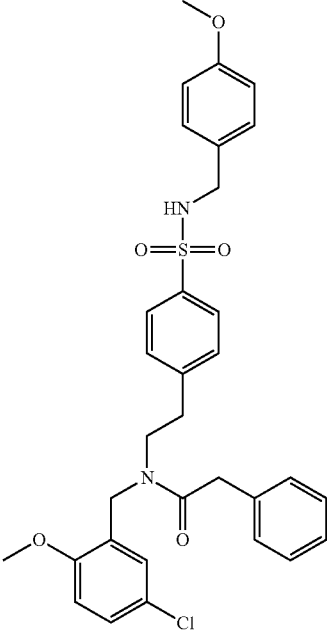 [SMILES: COc1ccc(CNS(=O)(=O)c2ccc(CCN(Cc3cc(Cl)ccc3OC)C(=O)Cc3ccccc3)cc2)cc1] |
| SZ-N3I-23<br>+++ | 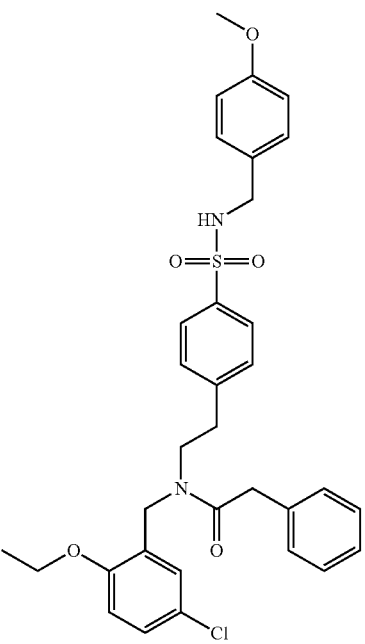 [SMILES: CCOc1ccc(Cl)cc1CN(CCc1ccc(S(=O)(=O)NCc2ccc(OC)cc2)cc1)C(=O)Cc1ccccc1] |

TABLE 1-continued

Inhibitory potency of analogs on the production of IL-1β by J774A.1 cells upon stimulation with LPS/ATP. (Unless otherwise indicated, + is an IC$_{50}$ > 30 μM; ++ is an IC$_{50}$ 10-30 μM; +++ is an IC$_{50}$ 1-10 μM; and ++++ is an IC$_{50}$ < 1 μM)

| Compound Number and IC$_{50}$ | Chemical Structure |
| --- | --- |
| SZ-N3I-24<br>++++ | |
| SZ-N3I-25<br>+++ | |

TABLE 1-continued

Inhibitory potency of analogs on the production of IL-1β by J774A.1 cells upon stimulation with LPS/ATP. (Unless otherwise indicated, + is an $IC_{50} > 30$ μM; ++ is an $IC_{50}$ 10-30 μM; +++ is an $IC_{50}$ 1-10 μM; and ++++ is an $IC_{50} < 1$ μM)

| Compound Number and $IC_{50}$ | Chemical Structure |
| --- | --- |
| SZ-N3I-26 ++++ | 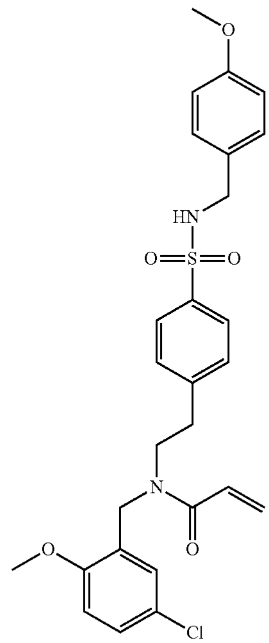 [SMILES: C=CC(=O)N(CCc1ccc(S(=O)(=O)NCc2ccc(OC)cc2)cc1)Cc1cc(Cl)ccc1OC] |
| SZ-N3I-27 ++++ | 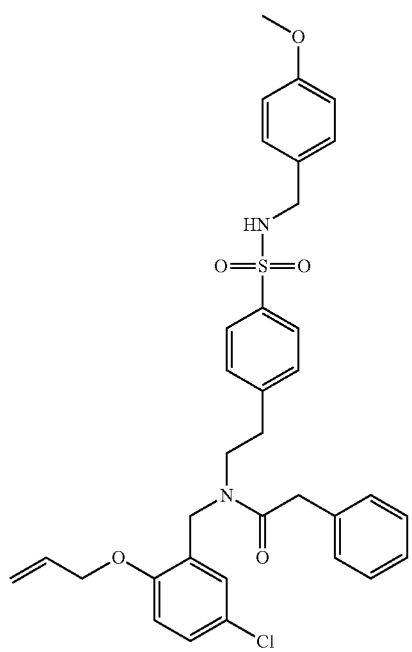 [SMILES: C=CCOc1ccc(Cl)cc1CN(CCc1ccc(S(=O)(=O)NCc2ccc(OC)cc2)cc1)C(=O)Cc1ccccc1] |

TABLE 1-continued
Inhibitory potency of analogs on the production of IL-1β by J774A.1 cells upon stimulation with LPS/ATP. (Unless otherwise indicated, + is an $IC_{50} > 30$ μM; ++ is an $IC_{50}$ 10-30 μM; +++ is an $IC_{50}$ 1-10 μM; and ++++ is an $IC_{50} < 1$ μM)
| Compound Number and $IC_{50}$ | Chemical Structure |
|---|---|
| SZ-N3I-28 +++ | 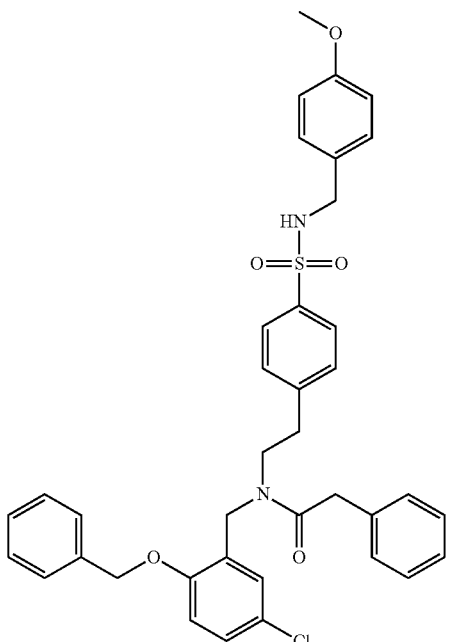 [SMILES: COc1ccc(CNS(=O)(=O)c2ccc(CCN(Cc3cc(Cl)ccc3OCc3ccccc3)C(=O)Cc3ccccc3)cc2)cc1] |
| SZ-N3I-29 + | 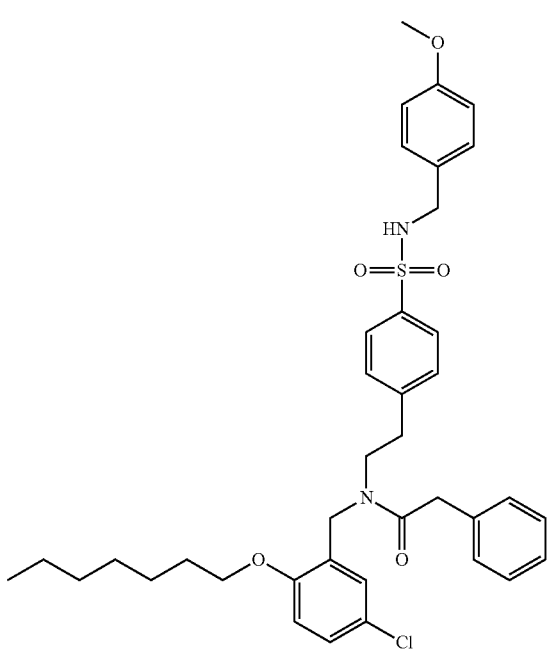 [SMILES: CCCCCCCOc1ccc(Cl)cc1CN(CCc1ccc(S(=O)(=O)NCc2ccc(OC)cc2)cc1)C(=O)Cc1ccccc1] |

TABLE 1-continued

Inhibitory potency of analogs on the production of IL-1β by J774A.1 cells upon stimulation with LPS/ATP. (Unless otherwise indicated, + is an IC$_{50}$ > 30 μM; ++ is an IC$_{50}$ 10-30 μM; +++ is an IC$_{50}$ 1-10 μM; and ++++ is an IC$_{50}$ < 1 μM)

| Compound Number and IC$_{50}$ | Chemical Structure |
| --- | --- |
| SZ-N3I-30<br>+++ | |
| SZ-N3I-31<br>+ | |

TABLE 1-continued
Inhibitory potency of analogs on the production of IL-1β by J774A.1 cells upon stimulation with LPS/ATP. (Unless otherwise indicated, + is an IC$_{50}$ > 30 μM; ++ is an IC$_{50}$ 10-30 μM; +++ is an IC$_{50}$ 1-10 μM; and ++++ is an IC$_{50}$ < 1 μM)
| Compound Number and IC$_{50}$ | Chemical Structure |
|---|---|
| SZ-N3I-32<br>+++ | 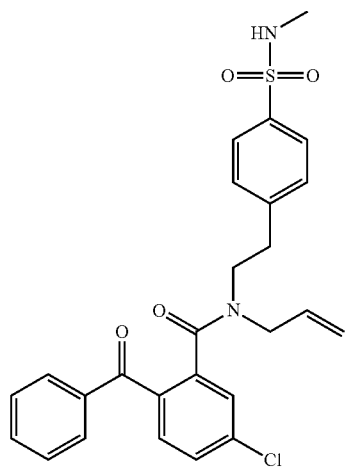 [SMILES: C=CCN(CCc1ccc(S(=O)(=O)NC)cc1)C(=O)c1cc(Cl)ccc1C(=O)c1ccccc1] |
| SZ-N3I-33<br>+++ | 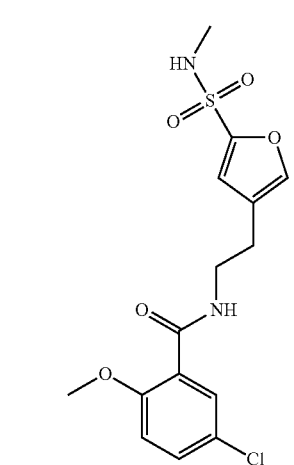 [SMILES: CNS(=O)(=O)c1cc(CCNC(=O)c2cc(Cl)ccc2OC)co1] |
| SZ-N3I-34<br>Compound 9<br>++++ | 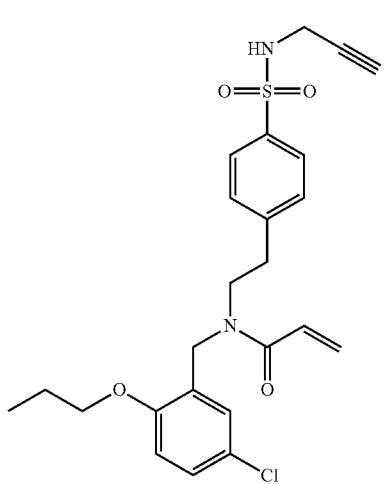 [SMILES: C#CCNS(=O)(=O)c1ccc(CCN(Cc2cc(Cl)ccc2OCCC)C(=O)C=C)cc1] |

TABLE 1-continued

Inhibitory potency of analogs on the production of IL-1β by J774A.1 cells upon stimulation with LPS/ATP. (Unless otherwise indicated, + is an $IC_{50} > 30$ μM; ++ is an $IC_{50}$ 10-30 μM; +++ is an $IC_{50}$ 1-10 μM; and ++++ is an $IC_{50} < 1$ μM)

| Compound Number and $IC_{50}$ | Chemical Structure |
|---|---|
| SZ-N3I-34 ++++ | 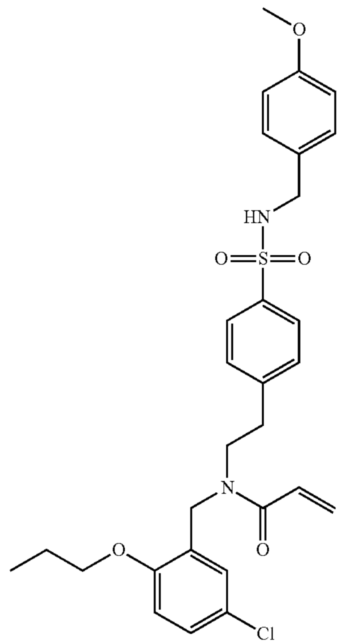 [SMILES: C=CC(=O)N(CCc1ccc(S(=O)(=O)NCc2ccc(OC)cc2)cc1)Cc1cc(Cl)ccc1OCCC] |
| SZ-N3I-35 ++++ | 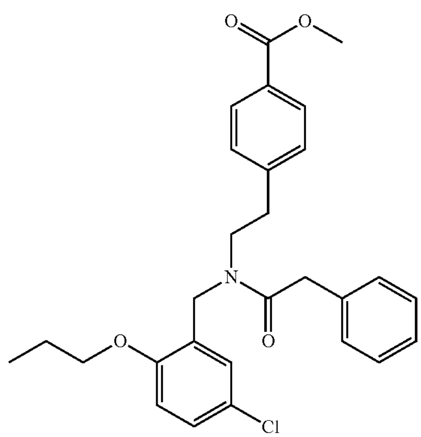 [SMILES: CCCOc1ccc(Cl)cc1CN(CCc1ccc(C(=O)OC)cc1)C(=O)Cc1ccccc1] |
| SZ-N3I-36 +++ | 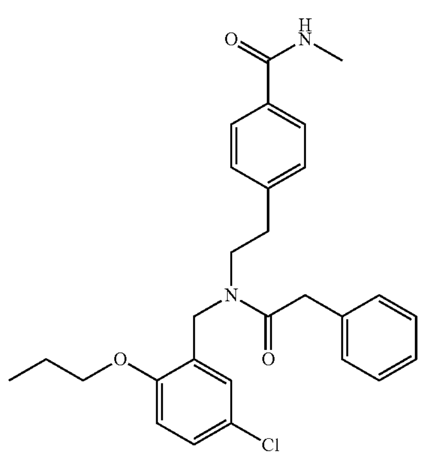 [SMILES: CCCOc1ccc(Cl)cc1CN(CCc1ccc(C(=O)NC)cc1)C(=O)Cc1ccccc1] |

TABLE 1-continued

Inhibitory potency of analogs on the production of IL-1β by J774A.1 cells upon stimulation with LPS/ATP. (Unless otherwise indicated, + is an IC$_{50}$ > 30 μM; ++ is an IC$_{50}$ 10-30 μM; +++ is an IC$_{50}$ 1-10 μM; and ++++ is an IC$_{50}$ < 1 μM)

| Compound Number and IC$_{50}$ | Chemical Structure |
|---|---|
| SZ-N3I-37<br>++++ | 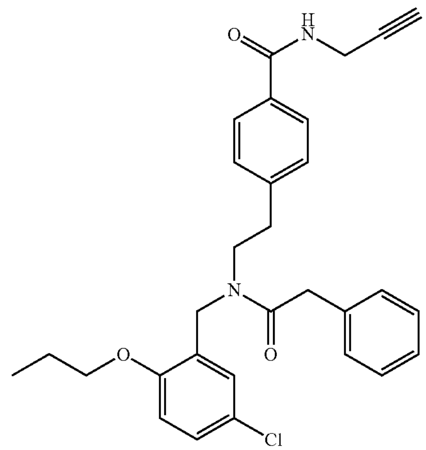 [SMILES: C#CCNC(=O)c1ccc(CCN(Cc2cc(Cl)ccc2OCCC)C(=O)Cc2ccccc2)cc1] |
| SZ-N3I-38<br>++++ | 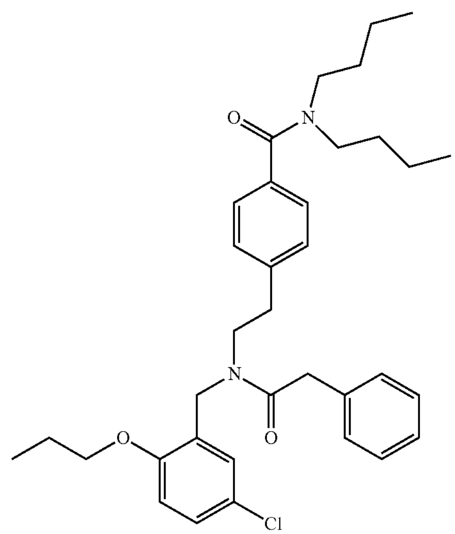 [SMILES: CCCCN(CCCC)C(=O)c1ccc(CCN(Cc2cc(Cl)ccc2OCCC)C(=O)Cc2ccccc2)cc1] |
| SZ-N3I-39<br>++++ | 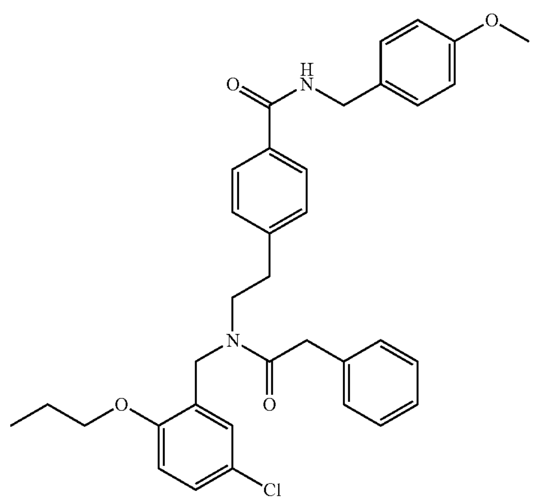 [SMILES: CCCOc1ccc(Cl)cc1CN(CCc1ccc(C(=O)NCc2ccc(OC)cc2)cc1)C(=O)Cc1ccccc1] |

TABLE 1-continued

Inhibitory potency of analogs on the production of IL-1β by J774A.1 cells upon stimulation with LPS/ATP. (Unless otherwise indicated, + is an IC$_{50}$ > 30 μM; ++ is an IC$_{50}$ 10-30 μM; +++ is an IC$_{50}$ 1-10 μM; and ++++ is an IC$_{50}$ < 1 μM)

| Compound Number and IC$_{50}$ | Chemical Structure |
| --- | --- |
| SZ-N3I-40 Compound 10 ++++ | 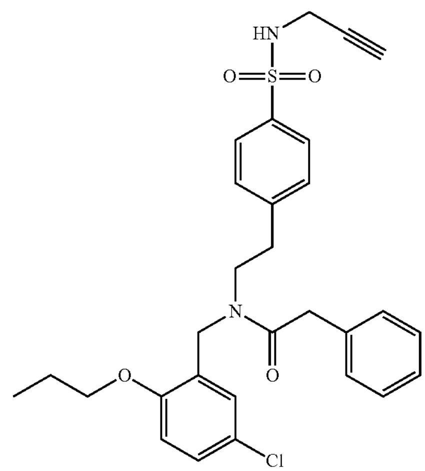 [SMILES: C#CCNS(=O)(=O)c1ccc(CCN(Cc2cc(Cl)ccc2OCCC)C(=O)Cc2ccccc2)cc1] |
| SZ-N3I-41 Compound 11 +++ | 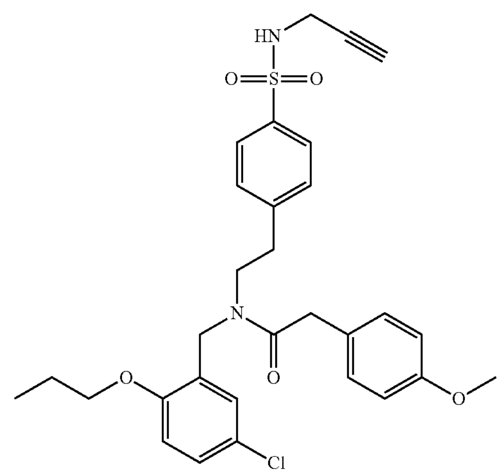 [SMILES: C#CCNS(=O)(=O)c1ccc(CCN(Cc2cc(Cl)ccc2OCCC)C(=O)Cc2ccc(OC)cc2)cc1] |
| SZ-N3I-42 Compound 12 ++++ | 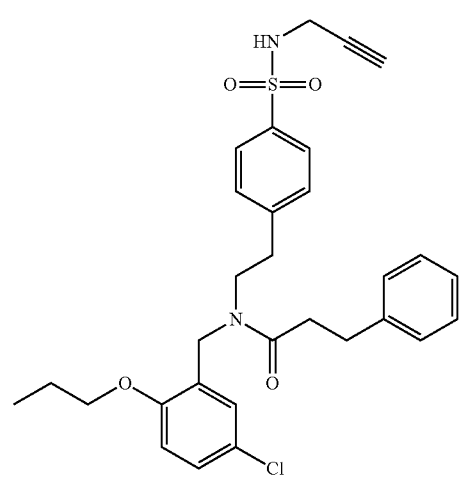 [SMILES: C#CCNS(=O)(=O)c1ccc(CCN(Cc2cc(Cl)ccc2OCCC)C(=O)CCc2ccccc2)cc1] |

TABLE 1-continued

Inhibitory potency of analogs on the production of IL-1β by J774A.1 cells upon stimulation with LPS/ATP. (Unless otherwise indicated, + is an IC$_{50}$ > 30 μM; ++ is an IC$_{50}$ 10-30 μM; +++ is an IC$_{50}$ 1-10 μM; and ++++ is an IC$_{50}$ < 1 μM)

| Compound Number and IC$_{50}$ | Chemical Structure |
| --- | --- |
| SZ-N3I-43 Compound 18 ++++ | 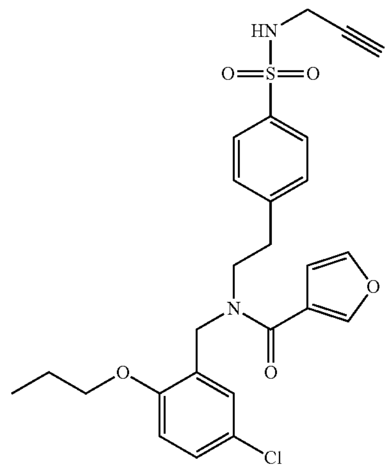 [SMILES: C#CCNS(=O)(=O)c1ccc(CCN(Cc2cc(Cl)ccc2OCCC)C(=O)c2ccoc2)cc1] |
| SZ-N3I-44 Compound 6 ++++ | 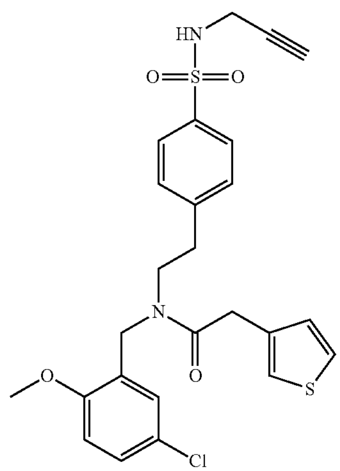 [SMILES: C#CCNS(=O)(=O)c1ccc(CCN(Cc2cc(Cl)ccc2OC)C(=O)Cc2ccsc2)cc1] |
| SZ-N3I-45 Compound 17, Formula IV ++++ | 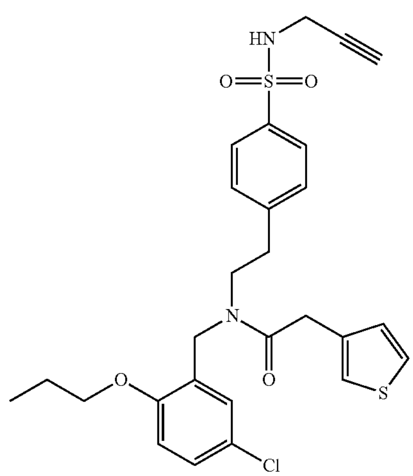 [SMILES: C#CCNS(=O)(=O)c1ccc(CCN(Cc2cc(Cl)ccc2OCCC)C(=O)Cc2ccsc2)cc1] |

TABLE 1-continued

Inhibitory potency of analogs on the production of IL-1β by J774A.1 cells upon stimulation with LPS/ATP. (Unless otherwise indicated, + is an $IC_{50} > 30$ μM; ++ is an $IC_{50}$ 10-30 μM; +++ is an $IC_{50}$ 1-10 μM; and ++++ is an $IC_{50} < 1$ μM)

| Compound Number and $IC_{50}$ | Chemical Structure |
| --- | --- |
| SZ-N3I-46 Compound 13 ++++ | 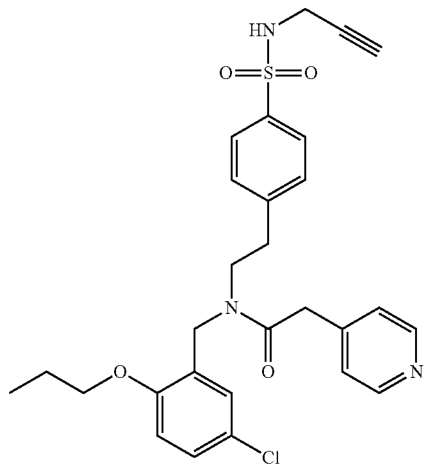 [SMILES: C#CCNS(=O)(=O)c1ccc(CCN(Cc2cc(Cl)ccc2OCCC)C(=O)Cc2ccncc2)cc1] |
| SZ-N3I-47 Compound 23 ++++ | 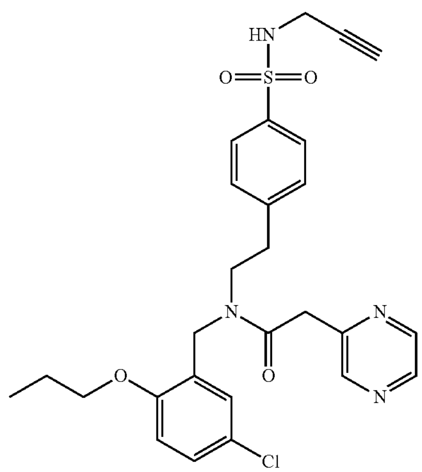 [SMILES: C#CCNS(=O)(=O)c1ccc(CCN(Cc2cc(Cl)ccc2OCCC)C(=O)Cc2cnccn2)cc1] |
| SZ-N3I-48 Compound 14 ++++ | 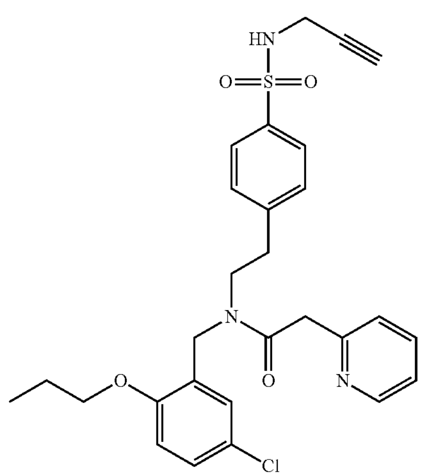 [SMILES: C#CCNS(=O)(=O)c1ccc(CCN(Cc2cc(Cl)ccc2OCCC)C(=O)Cc2ccccn2)cc1] |

TABLE 1-continued

Inhibitory potency of analogs on the production of IL-1β by J774A.1 cells upon stimulation with LPS/ATP. (Unless otherwise indicated, + is an IC$_{50}$ > 30 μM; ++ is an IC$_{50}$ 10-30 μM; +++ is an IC$_{50}$ 1-10 μM; and ++++ is an IC$_{50}$ < 1 μM)

| Compound Number and IC$_{50}$ | Chemical Structure |
|---|---|
| SZ-N3I-49 Compound 15 ++++ | 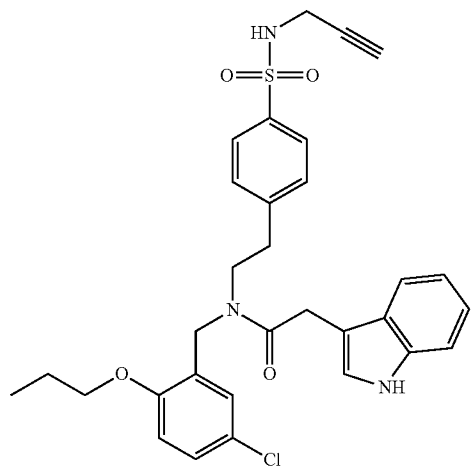 [SMILES: C#CCNS(=O)(=O)c1ccc(CCN(Cc2cc(Cl)ccc2OCCC)C(=O)Cc2c[nH]c3ccccc23)cc1] |
| SZ-N3I-50 Compound 19 ++++ | 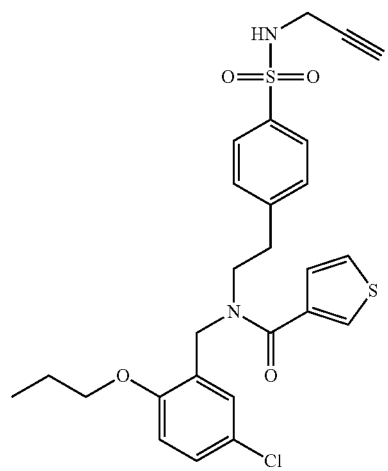 |
| SZ-N3I-51 Compound 20 ++++ | 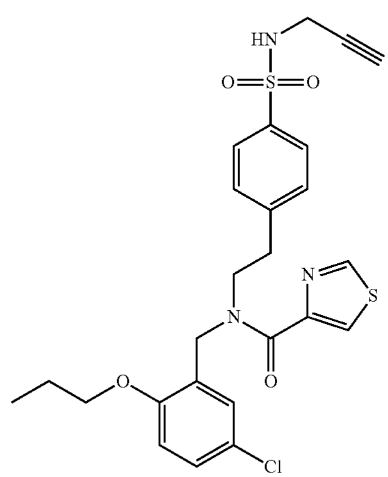 [SMILES: C#CCNS(=O)(=O)c1ccc(CCN(Cc2cc(Cl)ccc2OCCC)C(=O)c2cscn2)cc1] |

TABLE 1-continued

Inhibitory potency of analogs on the production of IL-1β by J774A.1 cells upon stimulation with LPS/ATP. (Unless otherwise indicated, + is an $IC_{50} > 30$ μM; ++ is an $IC_{50}$ 10-30 μM; +++ is an $IC_{50}$ 1-10 μM; and ++++ is an $IC_{50} < 1$ μM)

| Compound Number and $IC_{50}$ | Chemical Structure |
|---|---|
| SZ-N3I-52 Compound 16 +++ | 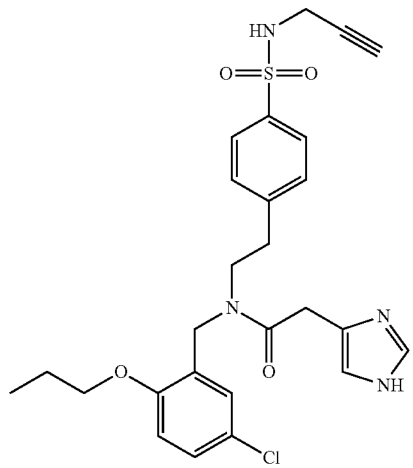 [SMILES: C#CCNS(=O)(=O)c1ccc(CCN(Cc2cc(Cl)ccc2OCCC)C(=O)Cc2c[nH]cn2)cc1] |
| SZ-N3I-53 Compound 21 ++++ | 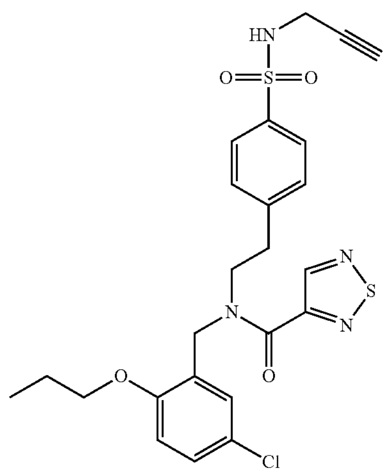 [SMILES: C#CCNS(=O)(=O)c1ccc(CCN(Cc2cc(Cl)ccc2OCCC)C(=O)c2cnsn2)cc1] |
| SZ-N3I-54 Compound 22 +++ | 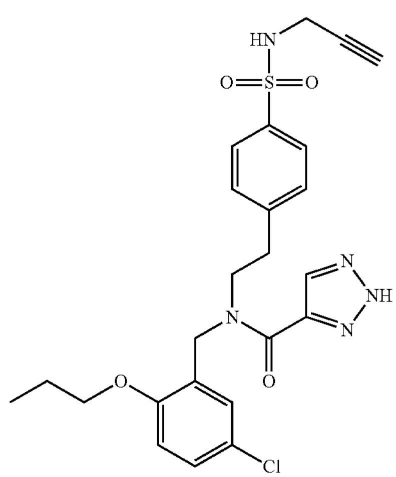 [SMILES: C#CCNS(=O)(=O)c1ccc(CCN(Cc2cc(Cl)ccc2OCCC)C(=O)c2cn[nH]n2)cc1] |

TABLE 1-continued
Inhibitory potency of analogs on the production of IL-1β by J774A.1 cells upon stimulation with LPS/ATP. (Unless otherwise indicated, + is an IC$_{50}$ > 30 μM; ++ is an IC$_{50}$ 10-30 μM; +++ is an IC$_{50}$ 1-10 μM; and ++++ is an IC$_{50}$ < 1 μM)
| Compound Number and IC$_{50}$ | Chemical Structure |
|---|---|
| SZ-N3I-55 Compound 27 ++++ | 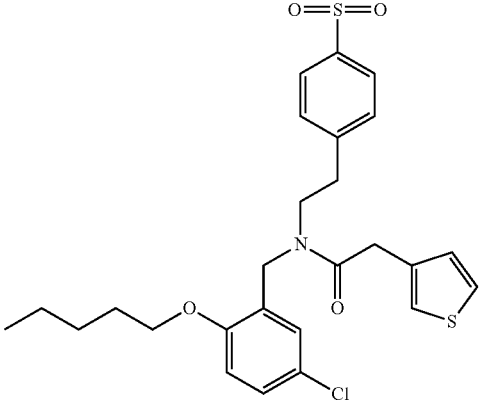 |
| SZ-N3I-56 Compound 28 ++++ | 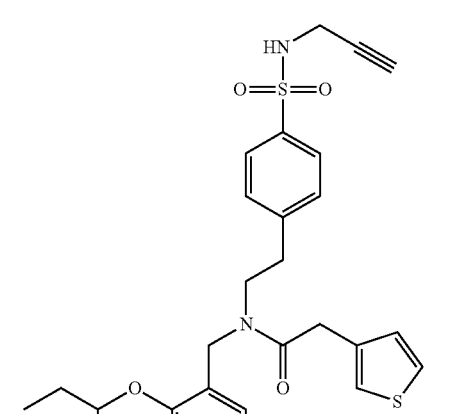 |
| SZ-N3I-57 Compound 26 ++++ | 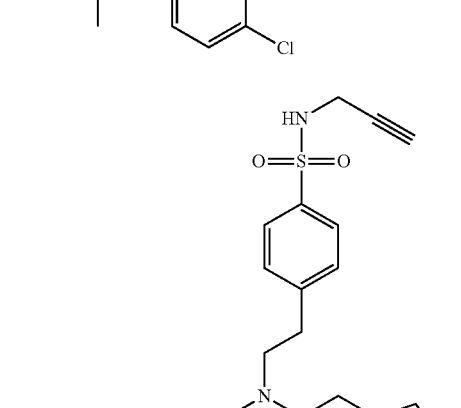 |

TABLE 1-continued

Inhibitory potency of analogs on the production of IL-1β by J774A.1 cells upon stimulation with LPS/ATP. (Unless otherwise indicated, + is an $IC_{50}$ > 30 μM; ++ is an $IC_{50}$ 10-30 μM; +++ is an $IC_{50}$ 1-10 μM; and ++++ is an $IC_{50}$ < 1 μM)

| Compound Number and $IC_{50}$ | Chemical Structure |
| --- | --- |
| SZ-N3I-58 Compound 24 ++++ | 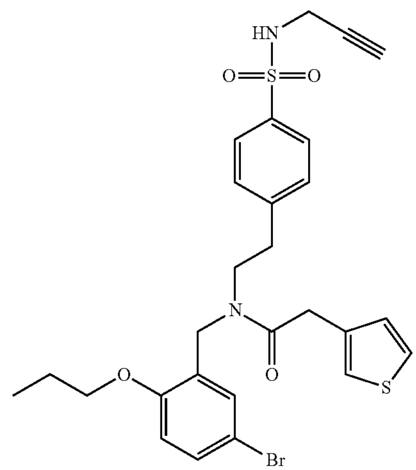 [SMILES: C#CCNS(=O)(=O)c1ccc(CCN(Cc2cc(Br)ccc2OCCC)C(=O)Cc2ccsc2)cc1] |
| SZ-N3I-59 Compound 25 ++++ | 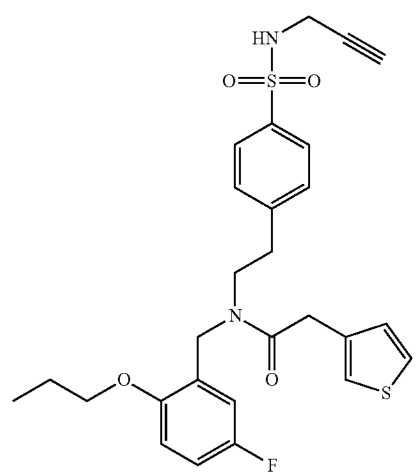 [SMILES: C#CCNS(=O)(=O)c1ccc(CCN(Cc2cc(F)ccc2OCCC)C(=O)Cc2ccsc2)cc1] |
| SZ-N3I-60 +++ | 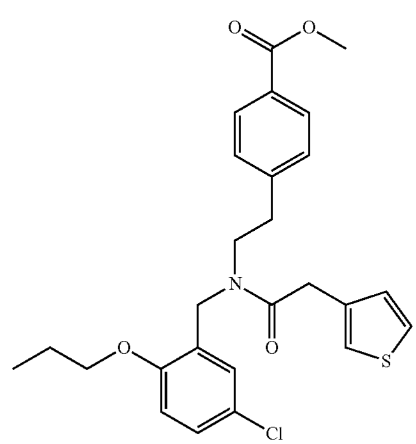 [SMILES: CCCOc1ccc(Cl)cc1CN(CCc1ccc(C(=O)OC)cc1)C(=O)Cc1ccsc1] |

TABLE 1-continued

Inhibitory potency of analogs on the production of IL-1β by J774A.1 cells upon stimulation with LPS/ATP. (Unless otherwise indicated, + is an $IC_{50} > 30$ μM; ++ is an $IC_{50}$ 10-30 μM; +++ is an $IC_{50}$ 1-10 μM; and ++++ is an $IC_{50} < 1$ μM)

| Compound Number and $IC_{50}$ | Chemical Structure |
|---|---|
| SZ-N3I-61<br>++++ | |
| SZ-N3I-62<br>+++ | |
| SZ-N3I-63<br>++++ | |

TABLE 1-continued

Inhibitory potency of analogs on the production of IL-1β by J774A.1 cells upon stimulation with LPS/ATP. (Unless otherwise indicated, + is an $IC_{50} > 30$ μM; ++ is an $IC_{50}$ 10-30 μM; +++ is an $IC_{50}$ 1-10 μM; and ++++ is an $IC_{50} < 1$ μM)

| Compound Number and $IC_{50}$ | Chemical Structure |
| --- | --- |
| SZ-N3I-64<br>+++ | |
| SZ-N3I-65<br>+++ | |
| SZ-N3I-66<br>+++ | |

TABLE 1-continued
Inhibitory potency of analogs on the production of IL-1β by J774A.1 cells upon stimulation with LPS/ATP. (Unless otherwise indicated, + is an $IC_{50} > 30$ μM; ++ is an $IC_{50}$ 10-30 μM; +++ is an $IC_{50}$ 1-10 μM; and ++++ is an $IC_{50} < 1$ μM)
| Compound Number and $IC_{50}$ | Chemical Structure |
|---|---|
| SZ-N3I-67 +++ | 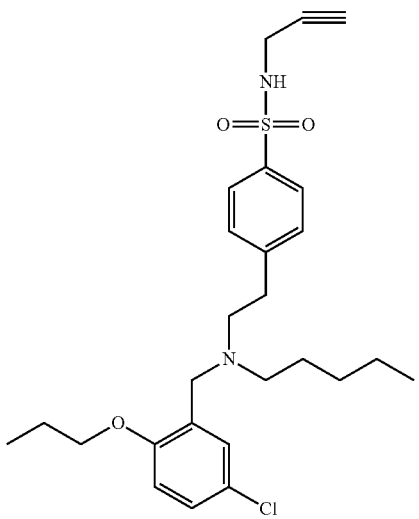 [SMILES: C#CCNS(=O)(=O)c1ccc(CCN(CCCCC)Cc2cc(Cl)ccc2OCCC)cc1] |
| SZ-N3I-68 +++ | 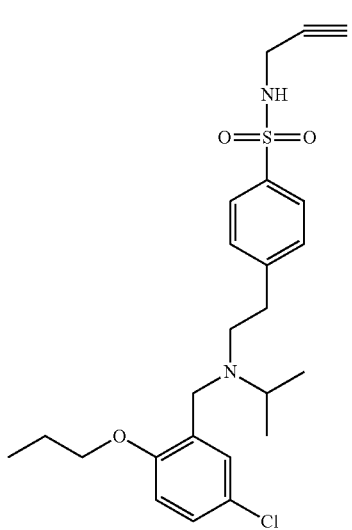 [SMILES: C#CCNS(=O)(=O)c1ccc(CCN(Cc2cc(Cl)ccc2OCCC)C(C)C)cc1] |

TABLE 1-continued
Inhibitory potency of analogs on the production of IL-1β by J774A.1 cells upon stimulation with LPS/ATP. (Unless otherwise indicated, + is an IC$_{50}$ > 30 μM; ++ is an IC$_{50}$ 10-30 μM; +++ is an IC$_{50}$ 1-10 μM; and ++++ is an IC$_{50}$ < 1 μM)
| Compound Number and IC$_{50}$ | Chemical Structure |
|---|---|
| SZ-N3I-69<br>+++ | 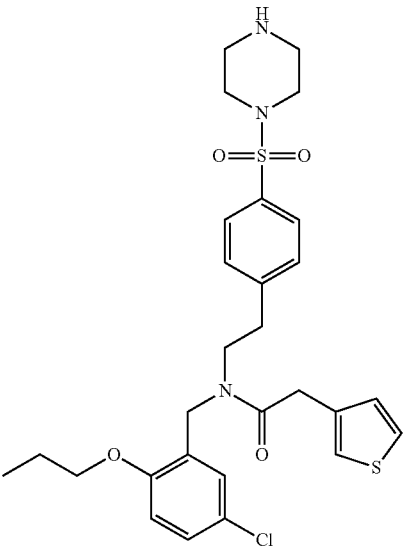 [SMILES: CCCOc1ccc(Cl)cc1CN(CCc1ccc(S(=O)(=O)N2CCNCC2)cc1)C(=O)Cc1ccsc1] |
| SZ-N3I-70<br>+++ | 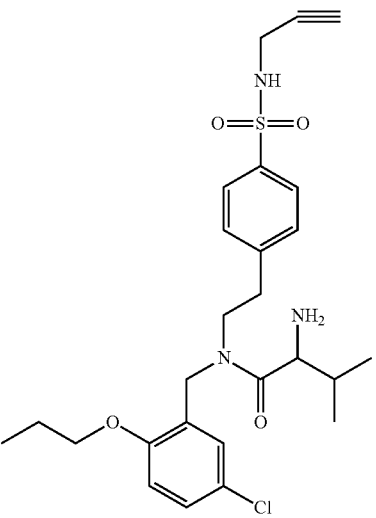 [SMILES: C#CCNS(=O)(=O)c1ccc(CCN(Cc2cc(Cl)ccc2OCCC)C(=O)C(N)C(C)C)cc1] |

TABLE 1-continued

Inhibitory potency of analogs on the production of IL-1β by J774A.1 cells upon stimulation with LPS/ATP. (Unless otherwise indicated, + is an IC$_{50}$ > 30 μM; ++ is an IC$_{50}$ 10-30 μM; +++ is an IC$_{50}$ 1-10 μM; and ++++ is an IC$_{50}$ < 1 μM)

| Compound Number and IC$_{50}$ | Chemical Structure |
|---|---|
| SZ-N3I-71 +++ | 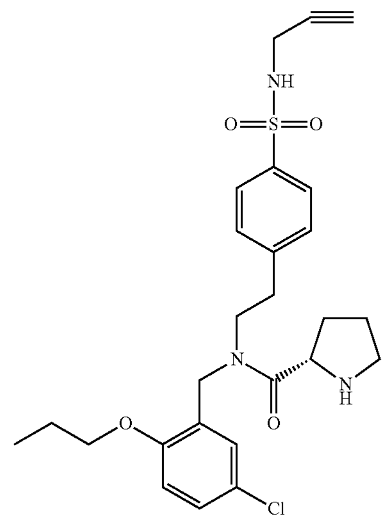 [SMILES: C#CCNS(=O)(=O)c1ccc(CCN(Cc2cc(Cl)ccc2OCCC)C(=O)[C@@H]2CCCN2)cc1] |
| SZ-N3I-72 +++ | 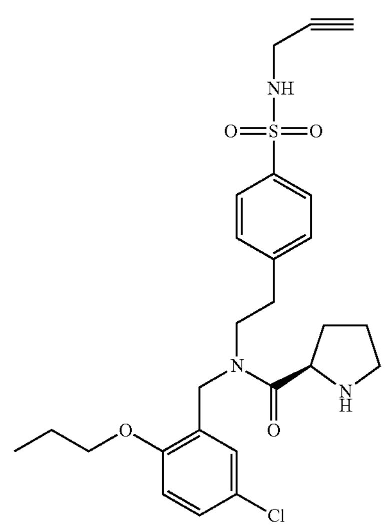 [SMILES: C#CCNS(=O)(=O)c1ccc(CCN(Cc2cc(Cl)ccc2OCCC)C(=O)[C@H]2CCCN2)cc1] |

TABLE 1-continued
Inhibitory potency of analogs on the production of IL-1β by J774A.1 cells upon stimulation with LPS/ATP. (Unless otherwise indicated, + is an $IC_{50} > 30$ μM; ++ is an $IC_{50}$ 10-30 μM; +++ is an $IC_{50}$ 1-10 μM; and ++++ is an $IC_{50} < 1$ μM)
| Compound Number and $IC_{50}$ | Chemical Structure |
|---|---|
| SZ-N3I-73 +++ | 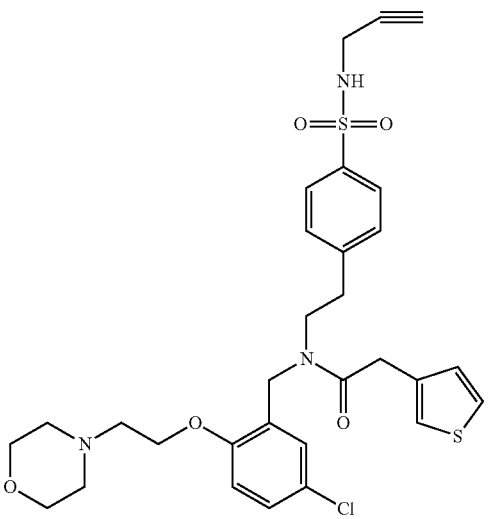 [SMILES: C#CCNS(=O)(=O)c1ccc(CCN(Cc2cc(Cl)ccc2OCCN2CCOCC2)C(=O)Cc2ccsc2)cc1] |
| SZ-N3I-74 +++ | 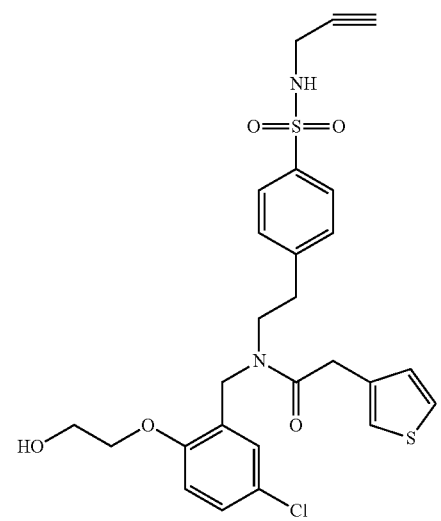 [SMILES: C#CCNS(=O)(=O)c1ccc(CCN(Cc2cc(Cl)ccc2OCCO)C(=O)Cc2ccsc2)cc1] |

TABLE 1-continued
Inhibitory potency of analogs on the production of IL-1β by J774A.1 cells upon stimulation with LPS/ATP. (Unless otherwise indicated, + is an IC$_{50}$ > 30 μM; ++ is an IC$_{50}$ 10-30 μM; +++ is an IC$_{50}$ 1-10 μM; and ++++ is an IC$_{50}$ < 1 μM)
| Compound Number and IC$_{50}$ | Chemical Structure |
| --- | --- |
| SZ-N3I-75<br>+++ | 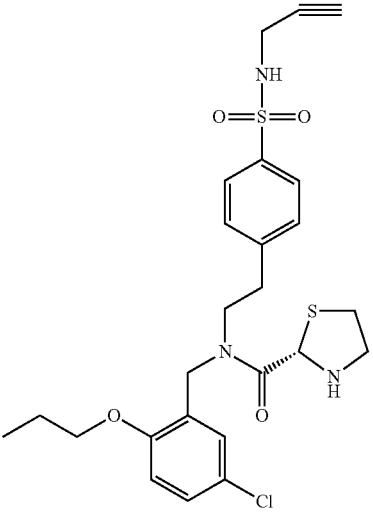 |
| SZ-N3I-76<br>+++ | 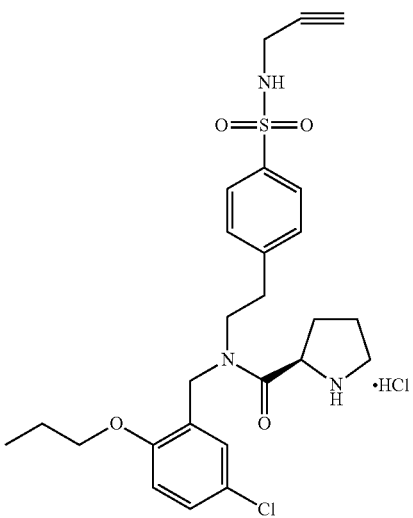 [SMILES: C#CCNS(=O)(=O)c1ccc(CCN(Cc2cc(Cl)ccc2OCCC)C(=O)[C@H]2CCCN2)cc1 ; Cl] |

TABLE 1-continued
Inhibitory potency of analogs on the production of IL-1β by J774A.1 cells upon stimulation with LPS/ATP. (Unless otherwise indicated, + is an $IC_{50}$ > 30 μM; ++ is an $IC_{50}$ 10-30 μM; +++ is an $IC_{50}$ 1-10 μM; and ++++ is an $IC_{50}$ < 1 μM)
| Compound Number and $IC_{50}$ | Chemical Structure |
|---|---|
| SZ-N3I-77<br>+++ | 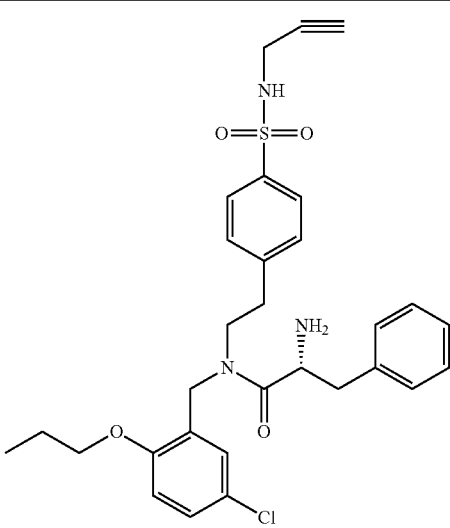 |
| SZ-N3I-78<br>++++ | 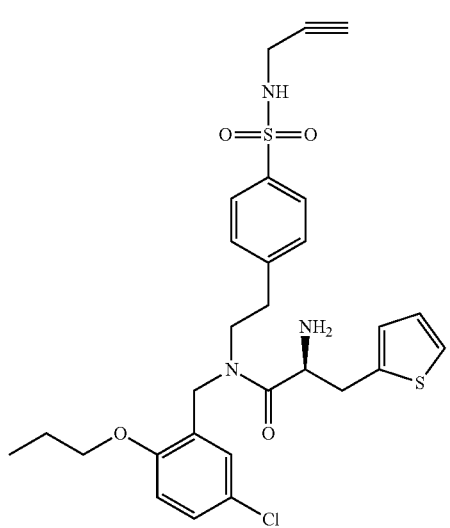 [SMILES: C#CCNS(=O)(=O)c1ccc(CCN(Cc2cc(Cl)ccc2OCCC)C(=O)[C@@H](N)Cc2cccs2)cc1] |

TABLE 1-continued
Inhibitory potency of analogs on the production of IL-1β by J774A.1 cells upon stimulation with LPS/ATP. (Unless otherwise indicated, + is an IC$_{50}$ > 30 μM; ++ is an IC$_{50}$ 10-30 μM; +++ is an IC$_{50}$ 1-10 μM; and ++++ is an IC$_{50}$ < 1 μM)
| Compound Number and IC$_{50}$ | Chemical Structure |
|---|---|
| SZ-N3I-79<br>++++ | 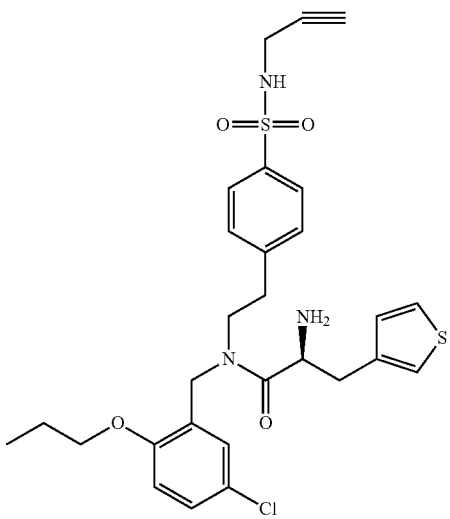 [SMILES: C#CCNS(=O)(=O)c1ccc(CCN(Cc2cc(Cl)ccc2OCCC)C(=O)[C@@H](N)Cc2ccsc2)cc1] |
| SZ-N3I-80<br>++++ | 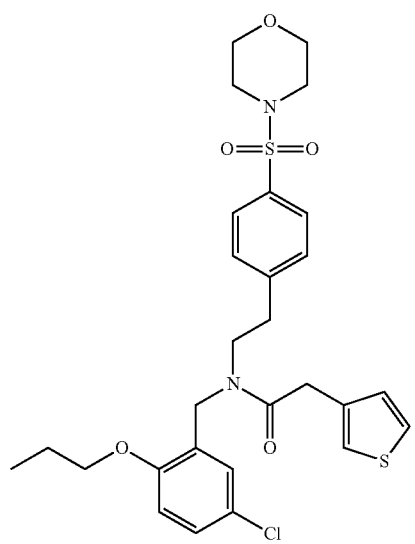 [SMILES: CCCOc1ccc(Cl)cc1CN(CCc1ccc(S(=O)(=O)N2CCOCC2)cc1)C(=O)Cc1ccsc1] |

TABLE 1-continued
Inhibitory potency of analogs on the production of IL-1β by J774A.1 cells upon stimulation with LPS/ATP. (Unless otherwise indicated, + is an $IC_{50} > 30$ μM; ++ is an $IC_{50}$ 10-30 μM; +++ is an $IC_{50}$ 1-10 μM; and ++++ is an $IC_{50} < 1$ μM)
| Compound Number and $IC_{50}$ | Chemical Structure |
| --- | --- |
| SZ-N3I-81 ++++ | 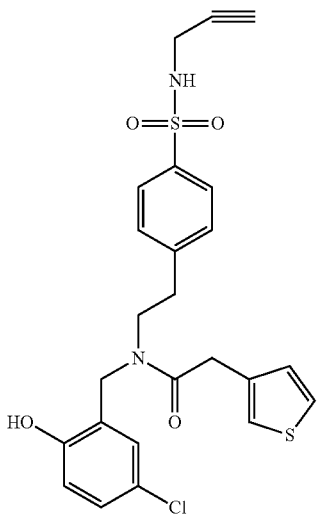 [SMILES: C#CCNS(=O)(=O)c1ccc(CCN(Cc2cc(Cl)ccc2O)C(=O)Cc2ccsc2)cc1] |
| SZ-N3I-82 ++++ | 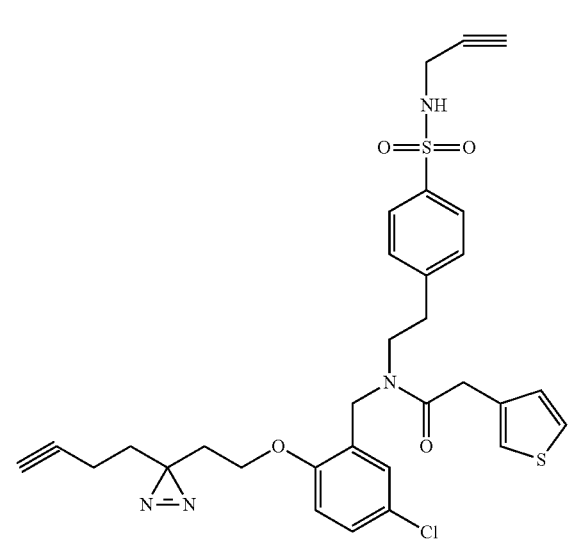 [SMILES: C#CCCC1(CCOc2ccc(Cl)cc2CN(CCc2ccc(S(=O)(=O)NCC#C)cc2)C(=O)Cc2ccsc2)N=N1] |

TABLE 1-continued
Inhibitory potency of analogs on the production of IL-1β by J774A.1 cells upon stimulation with LPS/ATP. (Unless otherwise indicated, + is an $IC_{50} > 30$ μM; ++ is an $IC_{50}$ 10-30 μM; +++ is an $IC_{50}$ 1-10 μM; and ++++ is an $IC_{50} < 1$ μM)
| Compound Number and $IC_{50}$ | Chemical Structure |
|---|---|
| SZ-N3I-83 ++++ | 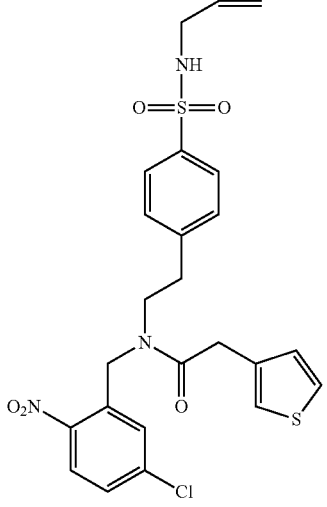 |
| SZ-N3I-84 +++ | 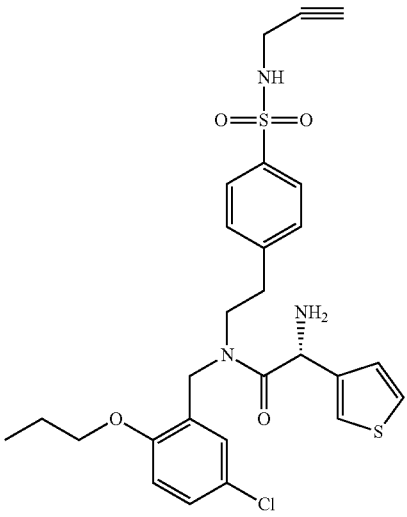 [SMILES: C#CCNS(=O)(=O)c1ccc(CCN(Cc2cc(Cl)ccc2OCCC)C(=O)[C@H](N)c2ccsc2)cc1] |

TABLE 1-continued

Inhibitory potency of analogs on the production of IL-1β by J774A.1 cells upon stimulation with LPS/ATP. (Unless otherwise indicated, + is an $IC_{50}$ > 30 μM; ++ is an $IC_{50}$ 10-30 μM; +++ is an $IC_{50}$ 1-10 μM; and ++++ is an $IC_{50}$ < 1 μM)

| Compound Number and $IC_{50}$ | Chemical Structure |
|---|---|
| SZ-N3I-85 ++++ | 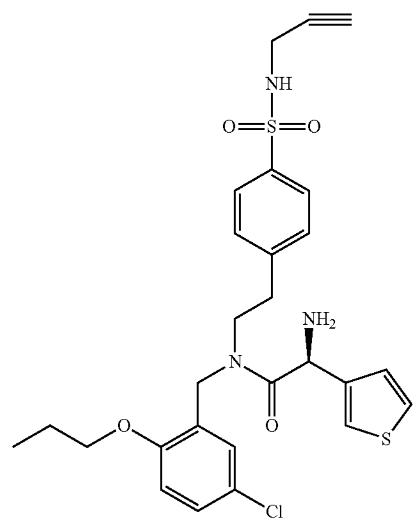 [SMILES: C#CCNS(=O)(=O)c1ccc(CCN(Cc2cc(Cl)ccc2OCCC)C(=O)[C@@H](N)c2ccsc2)cc1] |
| SZ-N3I-86 +++ | 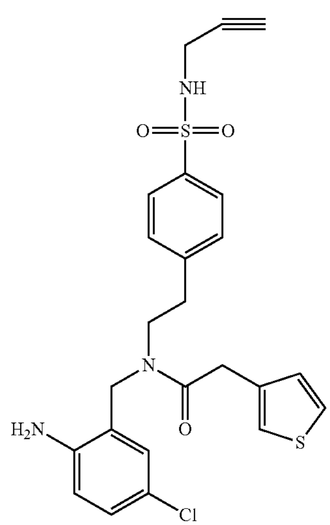 |

TABLE 1-continued

Inhibitory potency of analogs on the production of IL-1β by J774A.1 cells upon stimulation with LPS/ATP. (Unless otherwise indicated, + is an IC$_{50}$ > 30 μM; ++ is an IC$_{50}$ 10-30 μM; +++ is an IC$_{50}$ 1-10 μM; and ++++ is an IC$_{50}$ < 1 μM)

| Compound Number and IC$_{50}$ | Chemical Structure |
| --- | --- |
| SZ-N3I-87<br>++++ | |
| SZ-N3I-88<br>(Formula V)<br>++++ | |

TABLE 1-continued

Inhibitory potency of analogs on the production of IL-1β by J774A.1 cells upon stimulation with LPS/ATP. (Unless otherwise indicated, + is an $IC_{50}$ > 30 μM; ++ is an $IC_{50}$ 10-30 μM; +++ is an $IC_{50}$ 1-10 μM; and ++++ is an $IC_{50}$ < 1 μM)

| Compound Number and $IC_{50}$ | Chemical Structure |
| --- | --- |
| SZ-N3I-89 (Formula VI) ++++ | 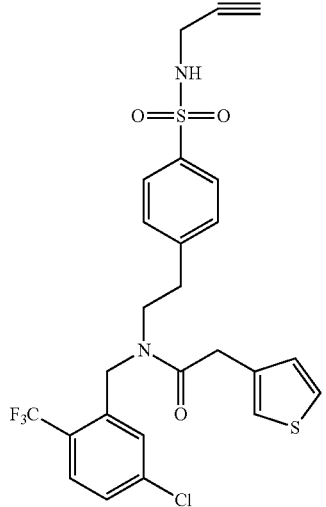 [SMILES: C#CCNS(=O)(=O)c1ccc(CCN(Cc2cc(Cl)ccc2C(F)(F)F)C(=O)Cc2ccsc2)cc1] |

Figure 3A:
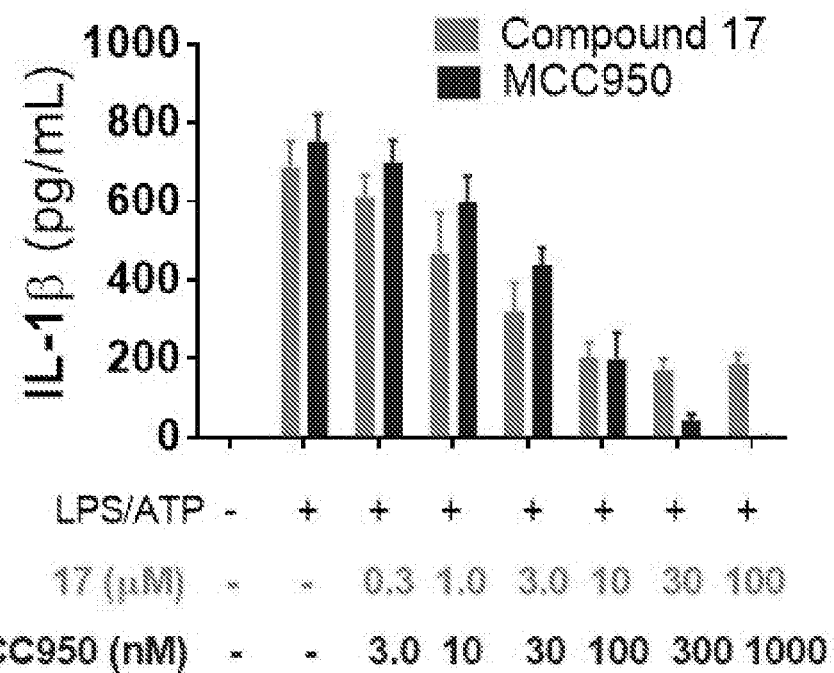
FIGS. 3A-3E show that compound 17 (Formula IV) selectively inhibits the NLRP3 inflammasome.

Example 16. Compound 17/Formula IV is a Selective Inhibitor of NLRP3 Inflammasome After the establishment of inhibitory potency on IL-1l3 release in J774A.1 cells for the designed analogs, we selected compound 17/Formula IV (YQ128), the most potent analog among this series, for further characterization. Before moving to test its selectivity, we confirmed its inhibitory activity in primary mouse peritoneal macrophages. MCC950 is a known NLRP3 inhibitor that is used as a positive control. As shown in FIG. 3A, both compound 17 and MCC950 dose-dependently suppressed the release of IL-1β from peritoneal macrophages upon LPS/ATP challenge with an IC50 of 1.59±0.60 and 0.04±0.0008 μM, respectively. Compound 17 is ~5 times less potent in peritoneal macrophages than in J774A.1 cells to inhibit the release of IL-1β. This may suggest that J774A.1 are more sensitive to compound 17 under the current experimental conditions.

Figure 3B:
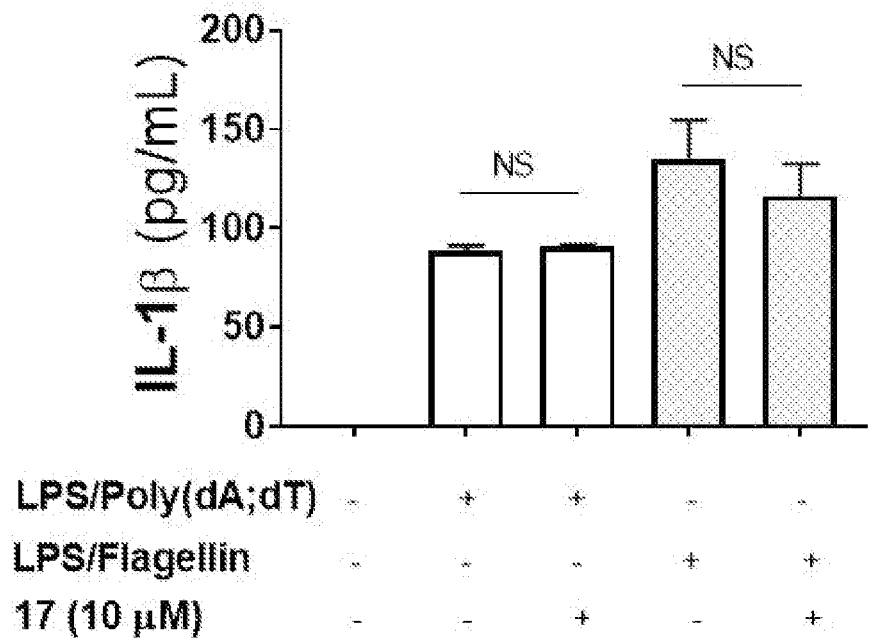

We next examined the effects of compound 17 on NLRC4 and AIM2 inflammasomes. As shown in FIG. 3B, treatment of J774A.1 cells with compound 17 under these experimental conditions did not significantly interfere with the production of IL-1β by NLRC4 or AIM2 inflammasome (by student t-test analysis), thus suggesting the specific inhibition of NLRP3 inflammasome by compound 17.

Figure 3C:
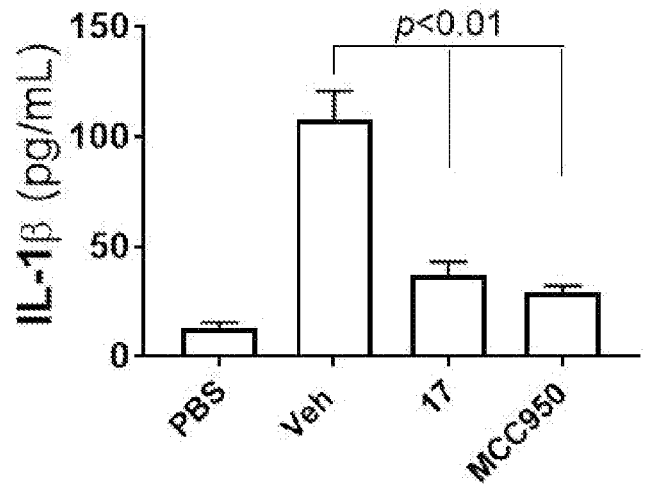
Figure 3D:
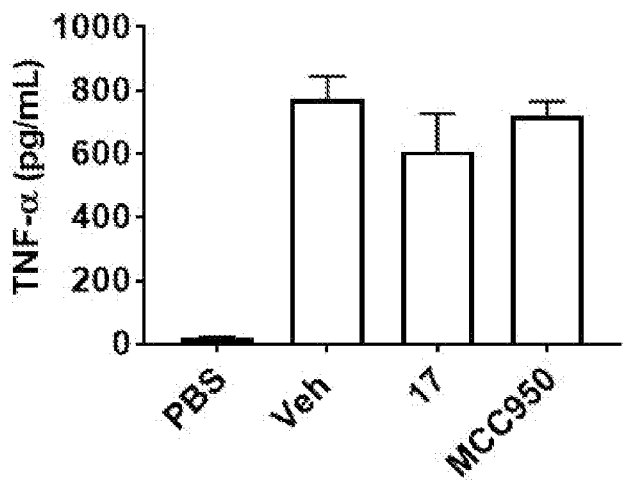
Figure 3E:
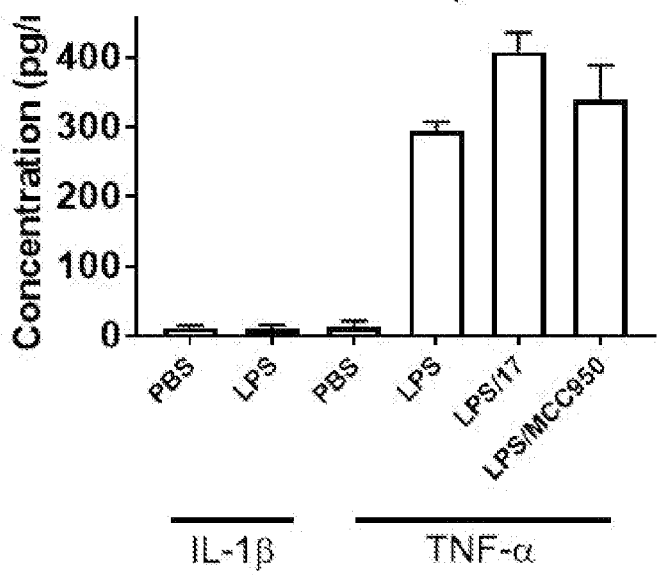

We then tested the in vivo engagement of and selectivity to the NLRP3 inflammasome by compound 17. C57BL/6 mice (n=3 per group) were pretreated with compound 17 or MCC950 (positive control) at 10 mg/kg before intraperitoneal injection of LPS, which has been shown to trigger IL-1β production in a NLRP3-dependent manner See He et al. (J Immunol 2013, 190:334-339). As shown in FIG. 3C, serum level of IL-1β was significantly reduced. In contrast, FIG. 3D shows that no significant inhibition in the TNF-α level was observed by the treatment of both compounds at the tested dose, thus strongly suggesting the selective in vivo engagement of NLRP3 inflammasome in the observed effects by compound 17 and MCC950. Lastly, we confirmed the selective inhibition on NLRP3 inflammasome by compound 17 in nlrp3–/– mice (n=3 per group). As expected, upon stimulation with LPS, nlrp3 deficiency abolished the production of IL-1β while the production of TNF-α is normal (FIG. 3E). Treatment of nlrp3–/– mice with compound 17 (10 mg/kg) did not produce inhibition on the level of TNF-α and this again confirmed the selective inhibition on the NLRP3 inflammasome by our compound 17. The results from the selectivity studies serve as an indirect evidence to support the MOA that analogs derived from this chemical scaffold interfere with the NLRP3 inflammasome complex, instead of the upstream priming step by the LPS, which is consistent with our previously reported results (see Guo et al. (ACS Chem Neurosci. 2017; 8:2194-2201).

Example 17. Compound 17/Formula IV is a Blood-Brain Barrier Penetrant but Shows Poor Oral Pharmacokinetic Properties Since one objective of the invention is to develop small molecule inhibitors of the NLRP3 inflammasome as potential therapeutics for neurodegenerative disorders, especially for AD, effective drug candidates need to cross the blood-brain barrier (BBB) and reach the brain tissue and preferably be suitable for chronic once-daily oral administration. To test whether compound 17 is a brain penetrant, we first determined its permeability and transport directionality using immortalized human cerebral microvascular endothelial cells hCMEC/D3 as the human BBB model (See Weksler et al. Fluids Barriers CAN. 2013; 10:16-26). This model expresses functional efflux transporters such as P-glycoprotein which are also expressed at the BBB; it has been widely used as a surrogate for human BBB. Apparent permeability (Papp) was calculated using Papp=(dX/dT·Vr)/ (A·Co), where dX/dT is the mass of transported compound (X) over time (T), Vr is the volume in the receiver compartment, A is the surface area of the membrane insert, and Co is the initial concentration in the donor compartment (See Hauser et al. *Antimicrob Agents Chemother.* 2017; 61:e01307-01317).

Figure 4A:
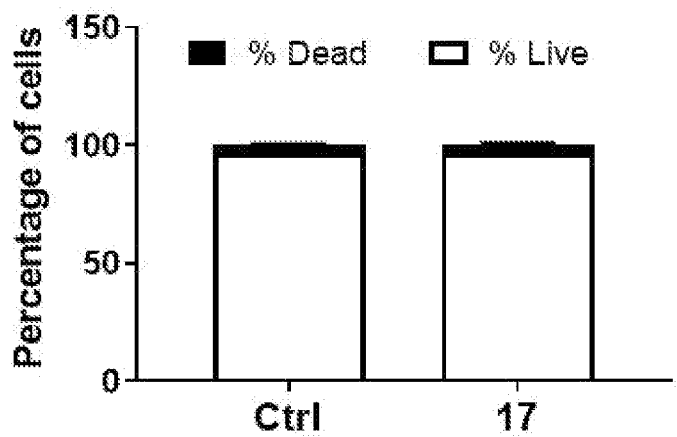
FIGS. 4A-4C show permeability of compound 17 (Formula IV) in hCMEC/D3 cells and PK properties in rats.
Figure 4B:
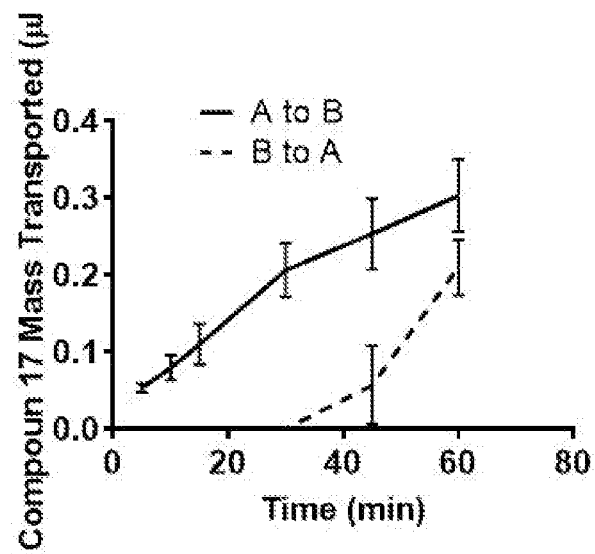
Figure 4C:
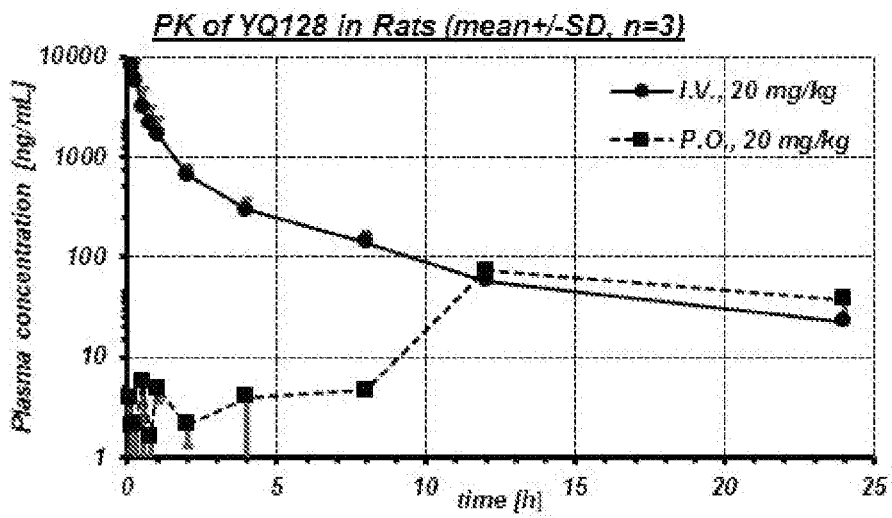

We first examined the potential cytotoxicity of compound 17 on hCMEC/D3 cells to rule out any potential interference with results interpretation, and the results demonstrated that 17 at 20 μM did not show significant toxic effects on these cells (FIG. 4A). The apical-to-basolateral (A to B) and basolateral-to-apical (B to A) Papp of compound 17 was 5.21±0.56×10-6 and 1.11±0.12×10-6 cm/sec, respectively (FIG. 4B). Thus, compound 17/exhibits an efflux ratio of 0.22, suggesting that compound 17 is not likely subject to active efflux. We next confirmed the in vivo BBB penetration of compound 17 in C57BL/6 mice (n=3 per time point) by oral (PO) administration (20 mg/kg, single dose). To accurately quantify the amount of compound 17 delivered to the brain, we perfused mouse brains to wash out the vascular blood completely prior to collecting and homogenizing brain tissues. Plasma and brain homogenate samples were analyzed by liquid chromatography tandem mass spectrometry (LC-MS/MS). As shown in Table 2, compound 17 appears in plasma with the highest concentration at as early as 30 min after PO administration. Brain concentrations of compound 17 after 0.5, 1, and 4 h were 21.3, 20.5, and 6.6 ng/g, respectively, indicating that compound 17 penetrated into the CNS after oral administration at the tested dose. Furthermore, the brain-to-plasma concertation ratio increases with time. However, after approximate conversion, the brain concentration of compound 17 was around 12 nM after 4 h of oral ingestion, 2.5-fold less than its in vitro IC50 value.

TABLE 2

BBB penetration of compound 17 (PO, 20 mg/kg) in mice (n = 3, mean ± SD) at various time points.

|  | 0.5 hours | 1 hour | 4 hours |
| --- | --- | --- | --- |
| brain (ng/g) | 21.25 ± 16.90 | 20.48 ± 4.19 | 6.58 ± 11.39 |
| plasma (ng/mL) | 277.33 ± 182.15 | 57.60 ± 55.65 | 8.00 ± 10.51 |
| brain:plasma ratio | 0.077 | 0.36 | 0.82 |

We next evaluated the basic pharmacokinetic properties of compound 17 in Sprague-Dawley rats (n=3 and 11 serial plasma samples over a period of 24 h; plasma concentrations were quantified by LC-MS/MS) after a dose of 20 mg/kg via intravenous (IV) and PO administration. The results showed that after IV administration, compound 17 exhibits extensive extravascular distribution with a large steady-state volume of distribution (Vdss) of 8.5 L/kg and rapid total clearance (CLtot) of 41 mL/min/kg, approaching hepatic (and renal) blood flow with the possibility of extrahepatic clearance mechanisms. This resulted in an intermediate terminal plasma half-life (t½) of 6.6 h after IV administration. After oral administration of an ad-hoc formulation, this compound shows delayed gastrointestinal absorption with a tmax and cmax of 12 h and 73 ng/mL, respectively (FIG. 4C); oral bioavailability (Foral) was estimated as 10%. This suggests the possibility of poor GI solubility/permeability and/or high first-pass effects at the tested dose of 20 mg/kg PO.

In continuing efforts to develop small molecule inhibitors of the NLRP3 inflammasome, a new chemical scaffold represented by compound HL16 (Formula I) was designed to allow more scope for structural modifications. This was done because, although HL16 exhibited improved inhibitory potency on IL-1β production from J774A.1 cells compared to our previously reported inhibitor, it suffered the loss of selectivity to the NLRP3 inflammasome. Further SAR studies of HL16 established that the 2-OCH3 can be modified to improve inhibitory potency. The acrylamide domain of HL16 can tolerate structural modifications and a heteroaromatic acetamide tend to provide analogs with improved potency. As a result of the SAR study disclosed above, one new lead compound (compound 17) was identified with a more than 4-fold increased inhibitory potency compared to HL16. Biological characterization in murine peritoneal macrophages and J774A.1 cells confirmed its inhibitory potency and selectivity to the NLRP3 inflammasome. More importantly, studies in LPS-challenged mice, a mouse model in which the release of IL-1β is NLRP3 inflammasome dependent, demonstrated that compound 17, after a single dose of 10 mg/kg, significantly and selectively suppressed the production of IL-1β, but not TNF-α, thus supporting its in vivo engagement of NLRP3 inflammasome. In addition, results from studies in nlrp3−/− mice echoed its selective engagement of NLRP3 inflammasome since no inhibitory activity on the production of TNF-α was observed. Studies from both in vitro and in vivo models supported the concept that compound 17 can cross the BBB to reach the CNS and is not likely subject to efflux transport. However, while PK studies in rats suggested adequate systemic characteristics with a plasma t½ of 6.6 hours, oral bioavailability was quite low (10%), likely due to poor GI solubility and possibly high first-pass effects. For example, Formula V and Formula VI are identified as likely to have potency that is comparable to Formula IV, along with better GI absorption and permeability. Collectively, these findings strongly encouraged further development of new small molecule compounds and analogs based on the chemical scaffold of Formula I, with improved PK properties as inhibitors of the NLRP3 inflammasome and therapeutic applications.

Example 18. HL-16/Formula I Inhibits EAE Development in Mice

Figure 5:
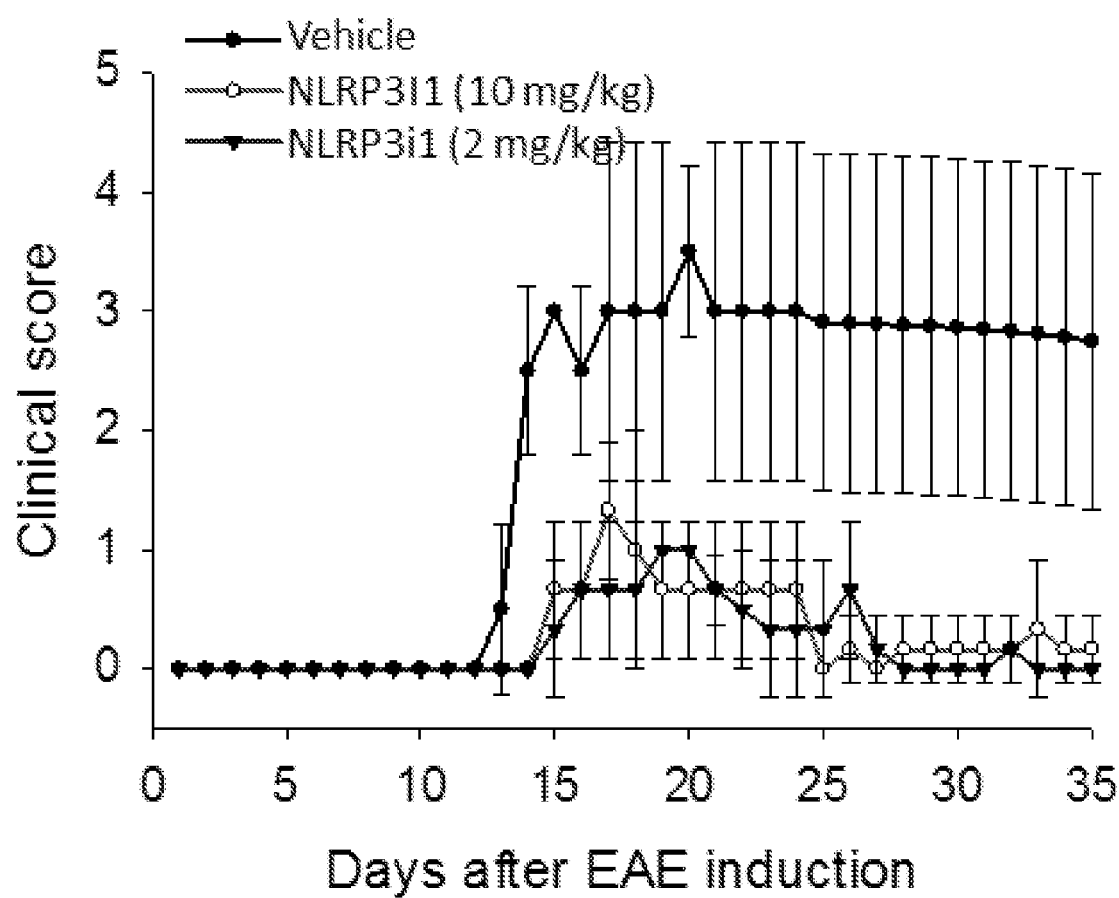
FIG. 5 shows that C57BL/6 mice were immunized with MOG peptide (200 μg) emulsified in CFA. NLRP3 inflammasome inhibitor, HL-16 (Formula III), treatments were started when the first sign of EAE appeared (decreased tail tone) at the indicated dose every other day. EAE development in mice was followed, and clinical scores were recorded.

C57BL/6 mice (n=10) were immunized subcutaneously in the dorsal flanks with MOG35-55 peptide emulsified in CFA on day 0. The mice received 200 ng pertussis toxin i.p. on days 0 and 2. Different doses of HL-16 (2 and 10 mg/kg) were administered i.p. to mice upon induction of the disease. To assess the therapeutic effect in clinically relevant setting, treatment was started on disease onset (reduced tail tone, clinical score=1). Control mice received DMSO. FIG. 5 shows that HL-16 at 10 mg/kg and 2 mg/kg substantially blocked induction of EAE, which occurred after day 12 in all mice treated with vehicle alone. Blockage of the induction was maintained for duration of the experiment, which was terminated at day 35. While mice showed a trend towards induction at about day 15, the differences between vehicle-treated mice and HL-16-treated mice was statistically significant for the duration of the experiment. There was no statistically significant difference between the 10 mg/kg and 2 ml/kg HL-16-treated groups.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:
1. A compound having the chemical structure of
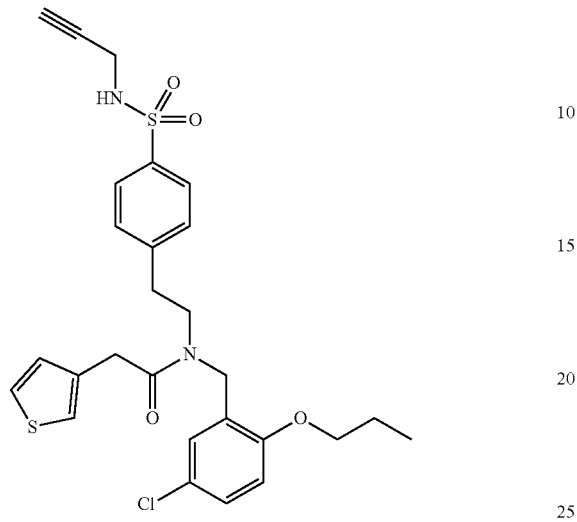
Formula IV
and pharmaceutically acceptable salts, solvates, or hydrates thereof.
* * * * *